(12) United States Patent
Hakonarson et al.

(10) Patent No.: US 10,100,362 B2
(45) Date of Patent: Oct. 16, 2018

(54) SCHIZOPHRENIA-ASSOCIATED GENETIC LOCI IDENTIFIED IN GENOME WIDE ASSOCIATION STUDIES AND METHODS OF USE THEREOF

(71) Applicant: THE CHILDREN'S HOSPITAL OF PHILADELPHIA, Philadelphia, PA (US)

(72) Inventors: Hakon Hakonarson, Malvern, PA (US); Patrick Sleiman, Philadelphia, PA (US); Xiao Chang, Drexel Hill, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 0 days.

(21) Appl. No.: 14/853,987

(22) Filed: Sep. 14, 2015

(65) Prior Publication Data

US 2016/0032390 A1   Feb. 4, 2016

Related U.S. Application Data

(63) Continuation-in-part of application No. PCT/US2014/028429, filed on Mar. 14, 2014.

(60) Provisional application No. 61/785,464, filed on Mar. 14, 2013, provisional application No. 61/788,509, filed on Mar. 15, 2013.

(51) Int. Cl.
| | |
|---|---|
| *C12Q 1/68* | (2018.01) |
| *G01N 33/68* | (2006.01) |
| *C12Q 1/6883* | (2018.01) |
| *G01N 33/50* | (2006.01) |

(52) U.S. Cl.
CPC ....... *C12Q 1/6883* (2013.01); *G01N 33/5008* (2013.01); *G01N 33/6803* (2013.01); *C12Q 2600/106* (2013.01); *C12Q 2600/156* (2013.01); *G01N 2500/04* (2013.01); *G01N 2500/10* (2013.01); *G01N 2800/30* (2013.01); *G01N 2800/302* (2013.01); *G01N 2800/304* (2013.01)

(58) Field of Classification Search
CPC ............ C12Q 1/6883; C12Q 2600/156; C12Q 2600/106; G01N 2800/302; G01N 2500/10; G01N 2800/304; G01N 33/6896; G01N 2333/705; G01N 33/5041; G01N 2333/726; G01N 2800/28; G01N 2800/30
See application file for complete search history.

(56) References Cited

U.S. PATENT DOCUMENTS

2015/0356243 A1* 12/2015 Andreassen ............ G06F 19/18
  702/20

OTHER PUBLICATIONS

Glessner et al. Strong synaptic transmission impact by copy number variations in schizophrenia. Proc Natl Acad Sci U S A. 2010;107(23):10584-9.
Ripke et al. Genome-wide association study identifies five new schizophrenia loci. Nature genetics. 2011;43(10):969-76.
Smith et al. A living fossil in the genome of a living fossil: Harbinger transposons in the coelacanth genome. Mol Biol Evol. 2012;29(3):985-93.
Tzimos et al. Safety and tolerability of oral paliperidone extended-release tablets in elderly patients with schizophrenia: a double-blind, placebo-controlled study with six-month open-label extension. Am J Geriatr Psychiatry. 2008;16(1):31-43.
Kramer et al. Paliperidone extended-release tablets for prevention of symptom recurrence in patients with schizophrenia: a randomized, double-blind, placebo-controlled study. J Clin Psychopharmacol. 2007;27(1):6-14.
Kane et al. Treatment of schizophrenia with paliperidone extended-release tablets: a 6-week placebo-controlled trial. Schizophr Res. 2007;90(1-3):147-61.
Marder et al. Efficacy and safety of paliperidone extended-release tablets: results of a 6-week, randomized, placebo-controlled study. Biol Psychiatry. 2007;62(12):1363-70.
Davidson et al. Efficacy, safety and early response of paliperidone extended-release tablets (paliperidone ER): results of a 6-week, randomized, placebo-controlled study. Schizophr Res. 2007;93(1-3):117-30.
Meltzer et al. Efficacy and tolerability of oral paliperidone extended-release tablets in the treatment of acute schizophrenia: pooled data from three 6-week, placebo-controlled studies. J Clin Psychiatry. 2008;69(5):817-29.
Canuso et al. Randomized, double-blind, placebo-controlled study of paliperidone extended-release and quetiapine in inpatients with recently exacerbated schizophrenia. Am J Psychiatry. 2009;166(6):691-701.
Berwaerts et al. Evaluation of the efficacy and safety of paliperidone extended-release in the treatment of acute mania: a randomized, double-blind, dose-response study. J Affect Disord. 2012;136(1-2):e51-60.
Vieta et al. A randomized, placebo- and active-controlled study of paliperidone extended release for the treatment of acute manic and mixed episodes of bipolar I disorder. Bipolar Disord. 2010;12(3):230-43.
Hough et al. Paliperidone palmitate maintenance treatment in delaying the time-to-relapse in patients with schizophrenia: a randomized, double-blind, placebo-controlled study. Schizophr Res. 2010;116(2-3):107-17.
Kozma et al. Changes in schizophrenia-related hospitalization and ER use among patients receiving paliperidone palmitate: results from a clinical trial with a 52-week open-label extension (OLE). Curr Med Res Opin. 2011;27(8)1603-11.
Fleischhacker et al. A randomized trial of paliperidone palmitate and risperidone long-acting injectable in schizophrenia. Int J Neuropsychopharmacol.1-12.

(Continued)

*Primary Examiner* — Gregory S Emch
(74) *Attorney, Agent, or Firm* — Kathleen D. Rigaut; Dann, Dorfman, Herrell & Skillman

(57) ABSTRACT

Compositions and methods for the identification of agents useful for the treatment of neurological disorders, including schizophrenia, are provided.

3 Claims, 53 Drawing Sheets

(56) References Cited

OTHER PUBLICATIONS

Gopal et al. Efficacy and safety of paliperidone palmitate in adult patients with acutely symptomatic schizophrenia: a randomized, double-blind, placebo-controlled, dose-response study. Int Clin Psychopharmacol. 2010;25(5):247-56.
Nasrallah et al. A controlled, evidence-based trial of paliperidone palmitate, a long-acting injectable antipsychotic, in schizophrenia. Neuropsychopharmacology. 2010;35(10):2072-82.
Hough et al. Safety and tolerability of deltoid and gluteal injections of paliperidone palmitate in schizophrenia. Prog Neuropsychopharmacol Biol Psychiatry. 2009;33(6):1022-31.
Pandina et al. A randomized, placebo-controlled study to assess the efficacy and safety of 3 doses of paliperidone palmitate in adults with acutely exacerbated schizophrenia. J Clin Psychopharmacol. 2010;30(3):235-44.
Bossie et al. Onset of efficacy and tolerability following the initiation dosing of long-acting paliperidone palmitate: post-hoc analyses of a randomized, double-blind clinical trial. BMC Psychiatry. 2011;11:79.

\* cited by examiner

1. *GRIN2A*

4. *DLG1*

5. *DLG4*

6. *ATP2B2*

7. *NOS1*

8. *ERBB4*

9. *ANSK1B*

10. *CHUK*

11. *CNTN2*

12. *CNTNAP2*

14. *CREB1*

15. *CREB5*

17. *GABBR2*

18. *GNA13*

19. *NCOR2*

21. *NTRK3* (remove rs146797905)

22. *PAK2*

24. *PTK2B*

26. *PTPRF*

SCHIZOPHRENIA-ASSOCIATED GENETIC LOCI IDENTIFIED IN GENOME WIDE ASSOCIATION STUDIES AND METHODS OF USE THEREOF

This application is a Continuation in Part application of PCT/US2014/028429 filed 14 Mar. 2014 which in turn claims priority to U.S. Provisional application Nos. 61/785,464 and 61/788,509 filed Mar. 14, 2013 and Mar. 15, 2013, respectively. The entire contents of each of the aforementioned applications being incorporated herein by reference as though set forth in full.

FIELD OF THE INVENTION

This invention relates to the fields of genetics and the diagnosis and treatment of schizophrenia, bi-polar disorder and autism. More specifically, the invention provides newly identified genetic loci containing gene targets strongly associated with these devastating neurological disorders for use in screening assays to identify therapeutic agents useful for the treatment of the same.

BACKGROUND OF THE INVENTION

Several publications and patent documents are cited throughout the specification in order to describe the state of the art to which this invention pertains. Each of these citations is incorporated herein by reference as though set forth in full.

Schizophrenia is a chronic, severe, and disabling brain disorder that affects about 1.1 percent of the U.S. population. People with schizophrenia sometimes hear voices others don't hear, believe that others are broadcasting their thoughts to the world, or become convinced that others are plotting to harm them. These experiences can make them fearful and withdrawn and cause difficulties when they try to have relationships with others.

People with schizophrenia may not make sense when they talk, may sit for hours without moving or talking much, or may seem perfectly fine until they talk about what they are really thinking. Because many people with schizophrenia have difficulty holding a job or caring for themselves, the burden on their families and society is significant as well.

Available treatments can relieve many of the disorder's symptoms, but most people who have schizophrenia must cope with some residual symptoms as long as they live. Clearly, a need exists for improved compositions and methods for the diagnosis and treatment of this devastating neuronal disorder.

SUMMARY OF THE INVENTION

In accordance with the present invention, using genome wide association studies (GWAS), we have identified 7 genome-wide significant loci, two of which are novel (chr15q25.2 containing neuromedin B, and chr8q24.3, TSNARE1, containing SNARE domain containing protein) and a third (chr1 q43 SDCCAG8), which has been reported to be associated with schizophrenia, bipolar disease and autism. The identification of these loci provide the means to screen agents which impact the activity of the proteins encoded by the genetic loci, thereby providing new therapeutics for the treatment of these neurological disorders. Such screening assays can be performed in vitro or in vivo.

Accordingly, in one aspect of the invention, a method for identifying agents which bind a protein encoded by a target sequence associated with neurological disease is provided. An exemplary method entails incubating the protein in the presence and absence of said agent, one of the protein or agent being detectably labeled; and determining whether said agent forms a complex with said protein, thereby identifying agents which bind proteins encoded by target sequences associated with neurological disease. In certain embodiments of the invention, the neurological disease is selected from the group consisting of schizophrenia, bi-polar disorder and autism. Proteins to be assessed using the methods of the invention include, for example, at least one of neuromedin B, TSNARE1, MAD1L1, CACNA1D, NT5DC2, ITH1, NEK4 NIMA, GNL3, PB1, GLT8D1, FTSJ2, NUDT1, SNX8, SEC11A, SCAND2, ZSCAN2, ALPK3, PDE8A, targets listed in FIG. 11 and Table 4. Such proteins can also include GRIN2A, GRIN2B, DLG2, DLG1, DLG4, ATP2B2, NOS1, ERBB4, ANSK1B, CHUK, CNTN2, CNTNAP2, CUL3, CREB1, CREB5, EP300, GABBR2, GNA13, NCOR2, NTRK3, PAK2, PTK2, PTK2B, PTN, PTPRF, STK4, SEMA4C, PTPRG, MAPK8IP1, TIAM1, IRS1, YWHAZ and TCF4. In an alternative embodiment of the method described above, the screening method is performed in cells expressing one, two, three or more of the proteins listed above.

In another embodiment of the invention, a method of treating schizophrenia (SCZ) or bi-polar (BP) disorder in a human subject is provided. An exemplary method comprises obtaining genotype sequence information from nucleic acids obtained from said subject, detecting in said information the presence of at least one SCZ or BP associated genetic alteration in at least one gene selected from neuromedin B, TSNARE1, MAD1L1, CACNA1D, NT5DC2, ITH1, NEK4 NIMA, GNL3, PB1, GLT8D1, FTSJ2, NUDT1, SNX8, SEC11A, SCAND2, ZSCAN2, ALPK3, PDE8A, GRIN2A, GRIN2B, DLG2, DLG1, DLG4, ATP2B2, NOS1, ERBB4, ANSK1B, CHUK, CNTN2, CNTNAP2, CUL3, CREB1, CREB5, EP300, GABBR2, GNA13, NCOR2, NTRK3, PAK2, PTK2, PTK2B, PTN, PTPRF, STK4, SEMA4C, PTPRG, MAPK8IP1, TIAM1, IRS1, YWHAZ and TCF4, correlating the presence of said SCZ or BP associated genetic alteration with a diagnosis of SCZ or BP; and administering to said human subject a therapeutically effective amount of at least one pharmaceutical agent useful for the treatment of SCZ or BP symptoms.

The present inventors have described several different groups of protein protein interactions, disruption of which being associated with an increased risk for schizophrenia. The invention also includes methods for assessing whether the agents screened above also alter protein protein interactions between protein networks listed in FIG. 16.

Agents to be administered to subject having genetic alterations in SCZ associated genes include, without limitation, Serdolect, ABT126, ABT127, ABT925, Zoleptil, ABT354, Rexapin, Haloperidol lactate, Nuplazid, AM831, ACP104, Quetros, Aristab, Risperidone ACIS, Paxiprid, Loxapine succinate, Aripiprazole, Zolafren, DA/5HT Modulator ADAMED, Kwetaplex, ADX63365, ADX50938, ADX71149, ATx11004, CimicoxibAffectis, FazaClo, GlyT-1 inhibitor, Joykem, Alkepin, Ilopt, InvegaSustenna, Asenapine maleate AMNEAL, AG0098, APN1125, AVL3288, Apexidone, Clozapex, Ziprasidone Hydrochloride, Haloperidol decanoate, Apo-Clozapine, Apo-Pimozide, Fasoracetam, Ziprasidone Hydrochloride, Olanzapine ODF LABTEC, Dogmil, Zyprexa, Rispa, Amipride, Seronia, Seroquel, Huntexil, Zyprobiox, Fasoracetam, Risbiodal, Biopiprazole, Aripiprazole, Miradol, Fluphenazinedecanoate and Prochlorperazineedisylate.

Another embodiment of the invention entails detection of genetic alterations in NTRK3 and when present, diagnosing the patient with SCZ and administering an agent selected from ARRY470, ARRY872, AZ23, AZD6918, CE245677, DS6051, KT6587, LOXO101, PLX7486, RXDX101, RXDX102 to subjects harboring such alterations.

Finally kits for practicing the methods disclosed above are also disclosed.

BRIEF DESCRIPTION OF THE DRAWINGS

FIG. 14C: Manhattan plot of SNP level associations (upper panel) and gene level associations (lower panel). Red dash line denotes the genome-wide significant line ($5\times10^{-8}$ for SNP level and $2.8\times10^{-6}$ for gene level). Blue dash line denotes the nominal significant line ($10^{-5}$ for SNP level and 0.05 for gene level).

FIG. 15E: Schematic overview of the network analysis in this study.

FIG. 16A. PPI network visualization of the most significant gene module derived from the network analysis. Gene-level P values (<0.05) are colored from green to red. Genes harboring DNMs and CNVs are shown as circles and triangles respectively. Genes harboring both DNMs and CNVs are diamond shaped. Edges width reflects the gene co-expression correlation between two connected nodes. Solid and dash line denote positive and negative correlations respectively. Top three significant modules identified when gene-level significance was set at $P_{node}<0.01$. FIG. 16B. Module 1 (seed: ATPB2_DLG1); FIG. 16C. Module 2 (seed: DLG1_SEMA4C). FIG. 16D. Module 3 (seed: DLG4_PTPRG). Top three significant modules identified when gene-level significance was set at $P_{node}<0.05$. FIG. 16E. Module 1 (seed: MAPK8IP1_TIAM1); FIG. 16F. Module 2 (seed: IRS1_YWHAZ); FIG. 16G Module 3 (seed: AKT1_NCF1).

FIG. 17A. GRIN2A; FIG. 17B. GRIN2B; FIG. 17AA. STK4; FIG. 17BB. TCF4.

DETAILED DESCRIPTION OF THE INVENTION

Figure 1:
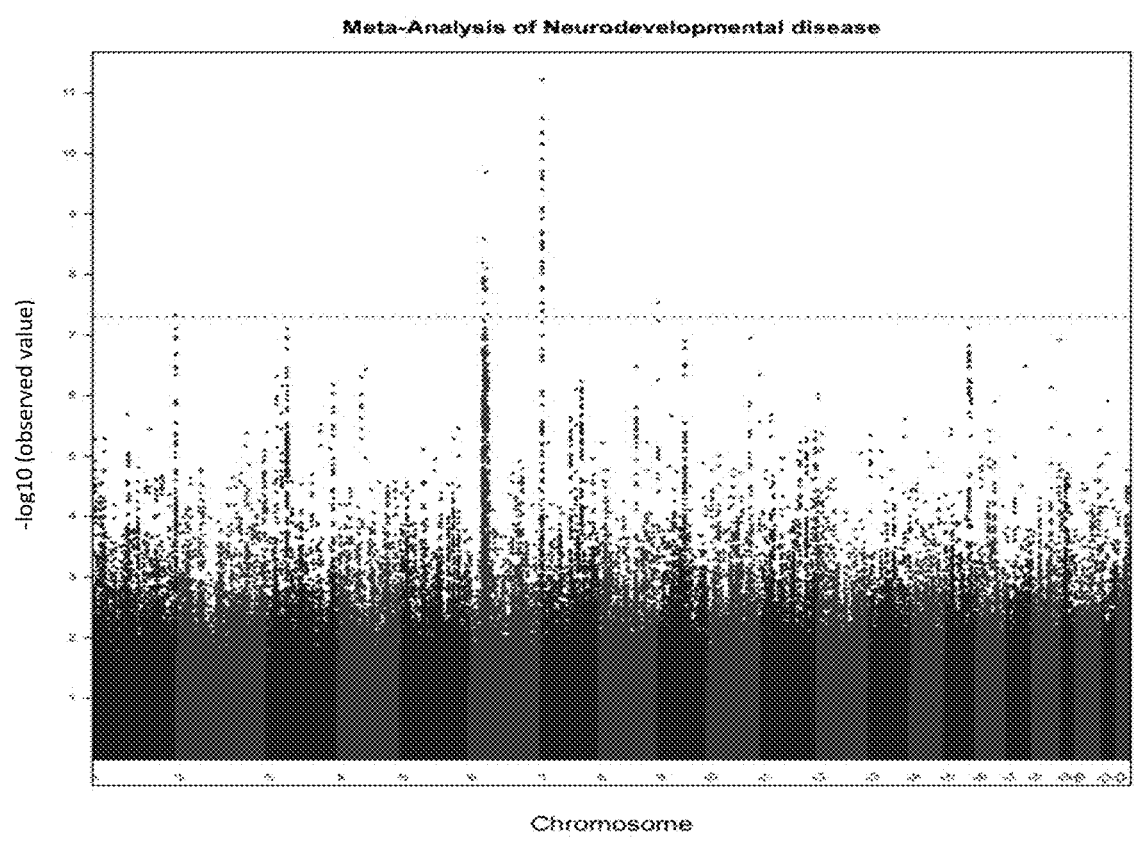
FIG. 1 shows Manhattan plot of SCZ-BP-ASD datasets meta-analysed.

Schizophrenia is a devastating mental disorder characterized by reality distortion. Common features are positive symptoms of hallucinations, delusions, disorganized speech and abnormal thought process, negative symptoms of social deficit, lack of motivation, anhedonia and impaired emotion processing, and cognitive deficits with occupational dysfunction. Onset of symptoms typically occurs in late adolescence or early adulthood, with approximately 1.5% of the population affected.

Hundreds of genomic loci have been identified with the recent advances of schizophrenia research in genome-wide association studies (GWAS) and sequencing studies. However, the functional interactions among those genes remain largely unknown. We developed a network-based approach to integrate multiple genetic risk factors, which lead to the discovery of new susceptibility genes and casual sub-networks or pathways in schizophrenia. We identified significantly and consistently over-represented pathways in two large-scale GWA studies, which are highly relevant to synaptic plasticity, neural development and signaling transduction, such as long-term potentiation, neurotrophin signaling pathway and the ERBB signaling pathway. We also demonstrated that genes targeted by common SNPs are more likely to interact with genes harboring de novo mutations (DNMs) in the protein-protein interaction (PPI) network, suggesting a mutual interplay of both common and rare genetic variants in schizophrenia. We further developed an edge-based search algorithm to identify the top-ranked gene modules associated with schizophrenia risk. Our results suggest that the N-methyl-D-aspartate receptor (NMDAR) interactome may play a leading role in the pathology of schizophrenia, as it is highly targeted by multiple types of genetic risk factors. Besides the genome-wide significant gene GRIN2A, multiple genes involved in the NMDAR interactome exhibited strong association with schizophrenia risk, such as DLG2 (rs12294291, $P=4.90 \times 10^{-7}$), GRIN2B (rs11757887, $P=8.81 \times 10^{-7}$), ATP2B2 (rs9879311, $P=2.77 \times 10^{-6}$) and NOS1 (rs2293052, $P=1.24 \times 10^{-6}$).

The present invention provides several newly identified genetic loci which contain genes strongly associated with the presence of a neurological disorder including schizophrenia, bi-polar disease and autism. The provision of these new gene targets facilitates the development of screening assays for identifying agents which modulate the activities of the encoded proteins. Such agents should have therapeutic efficacy for the treatment of neurological diseases.

The term "genetic alteration" refers to a change from the wild-type or reference sequence of one or more nucleic acid molecules. Genetic alterations include without limitation, base pair substitutions, duplications, additions and deletions of at least one nucleotide from a nucleic acid molecule of known sequence.

The term "solid matrix" as used herein refers to any format, such as beads, microparticles, a microarray, the surface of a microtitration well or a test tube, a dipstick or a filter. The material of the matrix may be polystyrene, cellulose, latex, nitrocellulose, nylon, polyacrylamide, dextran or agarose.

The phrase "consisting essentially of" when referring to a particular nucleotide or amino acid means a sequence having the properties of a given SEQ ID NO:. For example, when used in reference to an amino acid sequence, the phrase includes the sequence per se and molecular modifications that would not affect the functional and novel characteristics of the sequence.

"Target nucleic acid" as used herein refers to a previously defined region of a nucleic acid present in a complex nucleic acid mixture wherein the defined wild-type region contains at least one known nucleotide variation which may or may not be associated with schizophrenia. The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism from which it was derived. For example, the "isolated nucleic acid" may comprise a DNA molecule inserted into a vector, such as a plasmid or virus vector, or integrated into the genomic DNA of a prokaryote or eukaryote. An "isolated nucleic acid molecule" may also comprise a cDNA molecule. An isolated nucleic acid molecule inserted into a vector is also sometimes referred to herein as a recombinant nucleic acid molecule.

With respect to RNA molecules, the term "isolated nucleic acid" primarily refers to an RNA molecule encoded by an isolated DNA molecule as defined above. Alternatively, the term may refer to an RNA molecule that has been sufficiently separated from RNA molecules with which it would be associated in its natural state (i.e., in cells or tissues), such that it exists in a "substantially pure" form.

By the use of the term "enriched" in reference to nucleic acid it is meant that the specific DNA or RNA sequence constitutes a significantly higher fraction (2-5 fold) of the total DNA or RNA present in the cells or solution of interest than in normal cells or in the cells from which the sequence was taken. This could be caused by a person by preferential reduction in the amount of other DNA or RNA present, or by a preferential increase in the amount of the specific DNA or RNA sequence, or by a combination of the two. However, it should be noted that "enriched" does not imply that there are no other DNA or RNA sequences present, just that the relative amount of the sequence of interest has been significantly increased.

It is also advantageous for some purposes that a nucleotide sequence be in purified form. The term "purified" in reference to nucleic acid does not require absolute purity (such as a homogeneous preparation); instead, it represents an indication that the sequence is relatively purer than in the natural environment (compared to the natural level, this level should be at least 2-5 fold greater, e.g., in terms of mg/ml). Individual clones isolated from a cDNA library may be purified to electrophoretic homogeneity. The claimed DNA molecules obtained from these clones can be obtained directly from total DNA or from total RNA. The cDNA clones are not naturally occurring, but rather are preferably obtained via manipulation of a partially purified naturally occurring substance (messenger RNA). The construction of a cDNA library from mRNA involves the creation of a synthetic substance (cDNA) and pure individual cDNA clones can be isolated from the synthetic library by clonal selection of the cells carrying the cDNA library. Thus, the process which includes the construction of a cDNA library from mRNA and isolation of distinct cDNA clones yields an approximately $10^6$-fold purification of the native message. Thus, purification of at least one order of magnitude, preferably two or three orders, and more preferably four or five orders of magnitude is expressly contemplated.

The term "substantially pure" refers to a preparation comprising at least 50-60% by weight the compound of interest (e.g., nucleic acid, oligonucleotide, etc.). More preferably, the preparation comprises at least 75% by weight, and most preferably 90-99% by weight, the compound of interest. Purity is measured by methods appropriate for the compound of interest. The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. For example, specific hybridization can refer to a sequence which hybridizes to any schizophrenia specific marker gene or nucleic acid, but does not hybridize to other nucleotides. Also polynucleotide which "specifically hybridizes" may hybridize only to a neurospecific specific marker, such an schizophrenia-specific marker shown in the Tables contained herein. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989):

$$Tm=81.5"C+16.6 \text{ Log } [Na+]+0.41(\% \text{ G+C})-0.63(\% \text{ formamide})-600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid. Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 µg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 µg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 µg/ml denatured salmon sperm DNA at 42° C., and washed in 0.1×SSC and 0.5% SDS at 65° C. for 15 minutes.

The term "oligonucleotide," as used herein is defined as a nucleic acid molecule comprised of two or more ribo or deoxyribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single stranded or double stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non complementary nucleotide fragment may be attached to the 5' or 3' end of the probe, with the remainder of the probe sequence being complementary to the target strand. Alternatively, non complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single stranded or double stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non complementary nucleotide sequence may be attached to the 5' end of an otherwise complementary primer. Alternatively, non complementary bases may be interspersed within the oligonucleotide primer sequence, provided that the primer sequence has sufficient complementarity with the sequence of the desired template strand to functionally provide a template primer complex for the synthesis of the extension product.

Polymerase chain reaction (PCR) has been described in U.S. Pat. Nos. 4,683,195, 4,800,195, and 4,965,188, the entire disclosures of which are incorporated by reference herein. The term "vector" relates to a single or double stranded circular nucleic acid molecule that can be infected, transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art, and include any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5' end of the schizophrenia specific marker nucleic acid molecule such that the latter is transcribed into mRNA. Host cell machinery then translates mRNA into a polypeptide. Those skilled in the art will recognize that a nucleic acid vector can contain nucleic acid elements other than the promoter element and the schizophrenia specific marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, localization signals, or signals useful for polypeptide purification.

A "replicon" is any genetic element, for example, a plasmid, cosmid, bacmid, plastid, phage or virus, that is capable of replication largely under its own control. A replicon may be either RNA or DNA and may be single or double stranded.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism. As used herein, the terms "reporter," "reporter system", "reporter gene," or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector. When cloning a deletion or duplication containing nucleic acid into an expression vector, the skilled artisan appreciates that cloning a deletion for example, entails selection for flanking regions of the affected region having sufficient length to facilitate insertion into an expression vector. Such flanking regions can be 50, 100, 500, 1000, or more nucleotides in length. Such expression vectors enable further analysis of the affected genetic region, e.g., in cellular transformation assays.

The terms "recombinant organism," or "transgenic organism" refer to organisms which have a new combination of genes or nucleic acid molecules. A new combination of genes or nucleic acid molecules can be introduced into an organism using a wide array of nucleic acid manipulation techniques available to those skilled in the art. The term "organism" relates to any living being comprised of a least one cell. An organism can be as simple as one eukaryotic cell or as complex as a mammal. Therefore, the phrase "a recombinant organism" encompasses a recombinant cell, as well as eukaryotic and prokaryotic organism.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

"Sample" or "patient sample" or "biological sample" generally refers to a sample which may be tested for a particular molecule, preferably a schizophrenia specific marker molecule, such as a marker shown in the tables provided below. Samples may include but are not limited to cells, body fluids, including blood, serum, plasma, urine, saliva, tears, pleural fluid and the like.

The terms "agent" and "test compound" are used interchangeably herein and denote a chemical compound, a mixture of chemical compounds, a biological macromolecule, or an extract made from biological materials such as bacteria, plants, fungi, or animal (particularly mammalian) cells or tissues. Biological macromolecules include siRNA, shRNA, antisense oligonucleotides, peptides, peptide/DNA complexes, and any nucleic acid based molecule which exhibits the capacity to modulate the activity of the CNV containing nucleic acids described herein or their encoded proteins. Agents are evaluated for potential biological activity by inclusion in screening assays described hereinbelow.

Methods of Using Neurological Disease-Associated Genetic Loci for Development of Therapeutic Agents Since the genetic loci identified herein have been associated with the etiology of schizophrenia, bi-polar disease and autism, methods for identifying agents that modulate the activity of the genes and their encoded products should result in the generation of efficacious therapeutic agents for the treatment of this condition.

As can be seen from the data provided herein, several chromosomes contain regions which provide suitable targets for the rational design of therapeutic agents which modulate their activity. Specific organic molecules can thus be identified with capacity to bind to the active site of the proteins encoded by the identified nucleic acids based on conformation or key amino acid residues required for function. A combinatorial chemistry approach will be used to identify molecules with greatest activity and then iterations of these molecules will be developed for further cycles of screening. In certain embodiments, candidate agents can be screening from large libraries of synthetic or natural compounds. Such compound libraries are commercially available from a number of companies, including but not limited to Maybridge Chemical Co., (Trevillet, Cornwall, UK), Comgenex (Princeton, N.J.), Microsour (New Milford, Conn.) Aldrich (Milwaukee, Wis.) Akos Consulting and Solutions GmbH (Basel, Switzerland), Ambinter (Paris, France), Asinex (Moscow, Russia) Aurora (Graz, Austria), BioFocus DPI (Switzerland), Bionet (Camelford, UK), Chembridge (San Diego, Calif.), ChemDiv (San Diego, Calif.). The skilled person is aware of other sources and can readily purchase the same. Once therapeutically efficacious compounds are identified in the screening assays described herein, they can be formulated in to pharmaceutical compositions and utilized for the treatment of schizophrenia.

The polypeptides or fragments employed in drug screening assays may either be free in solution, affixed to a solid support or within a cell. One method of drug screening utilizes eukaryotic or prokaryotic host cells which are stably transformed with recombinant polynucleotides expressing the polypeptide or fragment, preferably in competitive binding assays. Such cells, either in viable or fixed form, can be used for standard binding assays. One may determine, for example, formation of complexes between the polypeptide or fragment and the agent being tested, or examine the degree to which the formation of a complex between the polypeptide or fragment and a known substrate is interfered with by the agent being tested.

Another technique for drug screening provides high throughput screening for compounds having suitable binding affinity for the encoded polypeptides and is described in detail in Geysen, PCT published application WO 84/03564, published on Sep. 13, 1984. Briefly stated, large numbers of different, small peptide test compounds, such as those described above, are synthesized on a solid substrate, such as plastic pins or some other surface. The peptide test compounds are reacted with the target polypeptide and washed. Bound polypeptide is then detected by methods well known in the art.

A further technique for drug screening involves the use of host eukaryotic cell lines or cells (such as described above) which have a nonfunctional or altered schizophrenia associated gene. These host cell lines or cells are defective at the polypeptide level. The host cell lines or cells are grown in the presence of drug compound. The rate of cellular metabolism of the host cells is measured to determine if the compound is capable of regulating the cellular metabolism in the defective cells. Host cells contemplated for use in the present invention include but are not limited to bacterial cells, fungal cells, insect cells, mammalian cells, and plant cells. The schizophrenia-associated DNA molecules may be introduced singly into such host cells or in combination to assess the phenotype of cells conferred by such expression. Methods for introducing DNA molecules are also well known to those of ordinary skill in the art. Such methods are set forth in Ausubel et al. eds., Current Protocols in Molecular Biology, John Wiley & Sons, NY, N.Y. 1995, the disclosure of which is incorporated by reference herein.

A wide variety of expression vectors are available that can be modified to express the novel DNA sequences of this invention. The specific vectors exemplified herein are merely illustrative, and are not intended to limit the scope of the invention. Expression methods are described by Sambrook et al. Molecular Cloning: A Laboratory Manual or Current Protocols in Molecular Biology 16.3-17.44 (1989). Expression methods in *Saccharomyces* are also described in Current Protocols in Molecular Biology (1989).

Suitable vectors for use in practicing the invention include prokaryotic vectors such as the pNH vectors (Stratagene Inc., 11099 N. Torrey Pines Rd., La Jolla, Calif. 92037), pET vectors (Novogen Inc., 565 Science Dr., Madison, Wis. 53711) and the pGEX vectors (Pharmacia LKB Biotechnology Inc., Piscataway, N.J. 08854). Examples of eukaryotic vectors useful in practicing the present invention include the vectors pRc/CMV, pRc/RSV, and pREP (Invitrogen, 11588 Sorrento Valley Rd., San Diego, Calif. 92121); pcDNA3.1/V5&His (Invitrogen); baculovirus vectors such as pVL1392, pVL1393, or pAC360 (Invitrogen); and yeast vectors such as YRP17, YIPS, and YEP24 (New England Biolabs, Beverly, Mass.), as well as pRS403 and pRS413 Stratagene Inc.); Picchia vectors such as pHIL-D1 (Phillips Petroleum Co., Bartlesville, Okla. 74004); retroviral vectors such as PLNCX and pLPCX (Clontech); and adenoviral and adeno-associated viral vectors.

Promoters for use in expression vectors of this invention include promoters that are operable in prokaryotic or eukaryotic cells. Promoters that are operable in prokaryotic cells include lactose (lac) control elements, bacteriophage lambda (pL) control elements, arabinose control elements, tryptophan (trp) control elements, bacteriophage T7 control elements, and hybrids thereof. Promoters that are operable in eukaryotic cells include Epstein Barr virus promoters, adenovirus promoters, SV40 promoters, Rous Sarcoma Virus promoters, cytomegalovirus (CMV) promoters, baculovirus promoters such as AcMNPV polyhedrin promoter, Picchia promoters such as the alcohol oxidase promoter, and Saccharomyces promoters such as the gal4 inducible promoter and the PGK constitutive promoter, as well as neuronal-specific platelet-derived growth factor promoter (PDGF), the Thy-1 promoter, the hamster and mouse Prion promoter (MoPrP), and the Glial fibrillar acidic protein (GFAP) for the expression of transgenes in glial cells.

In addition, a vector of this invention may contain any one of a number of various markers facilitating the selection of a transformed host cell. Such markers include genes associated with temperature sensitivity, drug resistance, or enzymes associated with phenotypic characteristics of the host organisms.

Host cells expressing the schizophrenia-associated nucleic acids of the present invention or functional fragments thereof provide a system in which to screen potential compounds or agents for the ability to modulate the development of neurological disease. Thus, in one embodiment, the nucleic acid molecules of the invention may be used to create recombinant cell lines for use in assays to identify agents which modulate aspects of cellular metabolism associated with neuronal signaling and neuronal cell communication and structure. Also provided herein are methods to screen for compounds capable of modulating the function of proteins encoded by the nucleic acids identified herein.

Another approach entails the use of phage display libraries engineered to express fragment of the polypeptides encoded by the nucleic acids of the invention on the phage surface. Such libraries are then contacted with a combinatorial chemical library under conditions wherein binding affinity between the expressed peptide and the components of the chemical library may be detected. U.S. Pat. Nos. 6,057,098 and 5,965,456 provide methods and apparatus for performing such assays.

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, (1991) Bio/Technology 9:19-21. In one approach, discussed above, the three-dimensional structure of a protein of interest or, for example, of the protein-substrate complex, is solved by x-ray crystallography, by nuclear magnetic resonance, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., (1990) Science 249:527-533). In addition, peptides may be analyzed by an alanine scan (Wells, (1991) Meth. Enzym. 202:390-411). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based.

One can bypass protein crystallography altogether by generating anti-idiotypic antibodies (anti-ids) to a functional, pharmacologically active antibody. As a mirror image of a mirror image, the binding site of the anti-ids would be expected to be an analog of the original molecule. The anti-id could then be used to identify and isolate peptides from banks of chemically or biologically produced banks of peptides. Selected peptides would then act as the pharmacore.

Thus, one may design drugs which have, e.g., improved polypeptide activity or stability or which act as inhibitors, agonists, antagonists, etc. of polypeptide activity. By virtue of the availability of schizophrenia associated nucleic acid sequences described herein, sufficient amounts of the encoded polypeptide may be made available to perform such analytical studies as x-ray crystallography. In addition, the knowledge of the protein sequence provided herein will guide those employing computer modeling techniques in place of, or in addition to x-ray crystallography.

In another embodiment, the availability of schizophrenia-associated nucleic acids enables the production of strains of laboratory mice carrying the schizophrenia-associated genes of the invention. Transgenic mice expressing the schizophrenia-associated nucleic acids of the invention provide a model system in which to examine the role of the protein encoded by the nucleic acid in the development and progression towards schizophrenia. Methods of introducing transgenes in laboratory mice are known to those of skill in the art. Three common methods include: 1. integration of retroviral vectors encoding the foreign gene of interest into an early embryo; 2. injection of DNA into the pronucleus of a newly fertilized egg; and 3. the incorporation of genetically manipulated embryonic stem cells into an early embryo. Production of the transgenic mice described above will facilitate the molecular elucidation of the role that a target protein plays in various cellular metabolic, neuronal and cognitive processes. Such mice provide an in vivo screening tool to study putative therapeutic drugs in a whole animal model and are encompassed by the present invention.

The term "animal" is used herein to include all vertebrate animals, except humans. It also includes an individual animal in all stages of development, including embryonic and fetal stages. A "transgenic animal" is any animal containing one or more cells bearing genetic information altered or received, directly or indirectly, by deliberate genetic manipulation at the subcellular level, such as by targeted recombination or microinjection or infection with recombinant virus. The term "transgenic animal" is not meant to encompass classical cross-breeding or in vitro fertilization, but rather is meant to encompass animals in which one or more cells are altered by or receive a recombinant DNA molecule. This molecule may be specifically targeted to a defined genetic locus, be randomly integrated within a chromosome, or it may be extrachromosomally replicating DNA. The term "germ cell line transgenic animal" refers to a transgenic animal in which the genetic alteration or genetic information was introduced into a germ line cell, thereby conferring the ability to transfer the genetic information to offspring. If such offspring, in fact, possess some or all of that alteration or genetic information, then they, too, are transgenic animals.

The alteration of genetic information may be foreign to the species of animal to which the recipient belongs, or foreign only to the particular individual recipient, or may be genetic information already possessed by the recipient. In the last case, the altered or introduced gene may be expressed differently than the native gene. Such altered or foreign genetic information would encompass the introduction of schizophrenia-associated nucleotide sequences.

The DNA used for altering a target gene may be obtained by a wide variety of techniques that include, but are not limited to, isolation from genomic sources, preparation of cDNAs from isolated mRNA templates, direct synthesis, or a combination thereof.

A preferred type of target cell for transgene introduction is the embryonal stem cell (ES). ES cells may be obtained from pre-implantation embryos cultured in vitro (Evans et al., (1981) Nature 292:154-156; Bradley et al., (1984) Nature 309:255-258; Gossler et al., (1986) Proc. Natl. Acad. Sci. 83:9065-9069). Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

One approach to the problem of determining the contributions of individual genes and their expression products is to use isolated schizophrenia-associated genes as insertional cassettes to selectively inactivate a wild-type gene in totipotent ES cells (such as those described above) and then generate transgenic mice. The use of gene-targeted ES cells in the generation of gene-targeted transgenic mice was described, and is reviewed elsewhere (Frohman et al., (1989) Cell 56:145-147; Bradley et al., (1992) Bio/Technology 10:534-539).

Techniques are available to inactivate or alter any genetic region to a mutation desired by using targeted homologous recombination to insert specific changes into chromosomal alleles. However, in comparison with homologous extrachromosomal recombination, which occurs at a frequency approaching 100%, homologous plasmid-chromosome recombination was originally reported to only be detected at frequencies between $10^{-6}$ and $10^{-3}$. Nonhomologous plasmid-chromosome interactions are more frequent occurring at levels $10^5$-fold to $10^2$ fold greater than comparable homologous insertion.

To overcome this low proportion of targeted recombination in murine ES cells, various strategies have been developed to detect or select rare homologous recombinants. One approach for detecting homologous alteration events uses the polymerase chain reaction (PCR) to screen pools of transformant cells for homologous insertion, followed by screening of individual clones. Alternatively, a positive genetic selection approach has been developed in which a marker gene is constructed which will only be active if homologous insertion occurs, allowing these recombinants to be selected directly. One of the most powerful approaches developed for selecting homologous recombinants is the positive-negative selection (PNS) method developed for genes for which no direct selection of the alteration exists. The PNS method is more efficient for targeting genes which are not expressed at high levels because the marker gene has its own promoter. Non-homologous recombinants are selected against by using the Herpes Simplex virus thymidine kinase (HSV-TK) gene and selecting against its non-homologous insertion with effective herpes drugs such as gancyclovir (GANC) or (1-(2-deoxy-2-fluoro-B-D arabinofluranosyl)-5-iodou-racil, (FIAU). By this counter selection, the number of homologous recombinants in the surviving transformants can be increased. Utilizing schizophrenia-associated nucleic acid as a targeted insertional cassette provides means to detect a successful insertion as visualized, for example, by acquisition of immunoreactivity to an antibody immunologically specific for the polypeptide encoded by schizophrenia-associated nucleic acid and, therefore, facilitates screening/selection of ES cells with the desired genotype.

As used herein, a knock-in animal is one in which the endogenous murine gene, for example, has been replaced with human schizophrenia-associated gene of the invention. Such knock-in animals provide an ideal model system for studying the development of schizophrenia.

As used herein, the expression of a schizophrenia-associated nucleic acid, fragment thereof, or an schizophrenia-associated fusion protein can be targeted in a "tissue specific manner" or "cell type specific manner" using a vector in which nucleic acid sequences encoding all or a portion of schizophrenia-associated nucleic acid are operably linked to regulatory sequences (e.g., promoters and/or enhancers) that direct expression of the encoded protein in a particular tissue or cell type. Such regulatory elements may be used to advantage for both in vitro and in vivo applications. Promoters for directing tissue specific proteins are well known in the art and described herein.

The nucleic acid sequence encoding the schizophrenia-associated genes of the invention may be operably linked to a variety of different promoter sequences for expression in transgenic animals. Such promoters include, but are not limited to a prion gene promoter such as hamster and mouse Prion promoter (MoPrP), described in U.S. Pat. No. 5,877,399 and in Borchelt et al., Genet. Anal. 13(6) (1996) pages 159-163; a rat neuronal specific enolase promoter, described in U.S. Pat. Nos. 5,612,486, and 5,387,742; a platelet-derived growth factor B gene promoter, described in U.S. Pat. No. 5,811,633; a brain specific dystrophin promoter, described in U.S. Pat. No. 5,849,999; a Thy-1 promoter; a PGK promoter; a CMV promoter; a neuronal-specific platelet-derived growth factor B gene promoter; and Glial fibrillar acidic protein (GFAP) promoter for the expression of transgenes in glial cells.

Methods of use for the transgenic mice of the invention are also provided herein. Transgenic mice into which a nucleic acid containing the schizophrenia-associated gene or its encoded protein have been introduced are useful, for example, to develop screening methods to screen therapeutic agents to identify those capable of modulating the development of schizophrenia.

Pharmaceuticals and Peptide Therapies

The elucidation of the role played by the schizophrenia associated genes described herein in neuronal signaling and brain structure facilitates the development of pharmaceutical compositions useful for treatment and diagnosis of schizophrenia. These compositions may comprise, in addition to one of the above substances, a pharmaceutically acceptable excipient, carrier, buffer, stabilizer or other materials well known to those skilled in the art. Such materials should be non-toxic and should not interfere with the efficacy of the active ingredient. The precise nature of the carrier or other material may depend on the route of administration, e.g.

oral, intravenous, cutaneous or subcutaneous, nasal, intramuscular, intraperitoneal routes.

Whether it is a polypeptide, antibody, peptide, nucleic acid molecule, small molecule or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual.

Kits and Articles of Manufacture

Any of the aforementioned products can be incorporated into a kit which may contain a schizophrenia or BP-associated CNV/SNP specific marker polynucleotide or one or more such markers immobilized on a Gene Chip, an oligonucleotide, a polypeptide, a peptide, an antibody, a label, marker, or reporter, a pharmaceutically acceptable carrier, a physiologically acceptable carrier, instructions for use, a container, a vessel for administration, an assay substrate, or any combination thereof.

The following examples are provided to illustrate certain embodiments of the invention. They are not intended to limit the invention in any way.

EXAMPLE I

Schizophrenia is a neuropsychiatric disorder with worldwide prevalence of 1%, causing a huge social/economic burden. While the etiology of schizophrenia remains unknown, genetic factors play a key role as the disease is highly heritable. Here, we used genome-wide association (GWAS) approach to uncover variants that associate with schizophrenia, uncovering novel biological pathways that may lead to new treatments.

Figure 2:
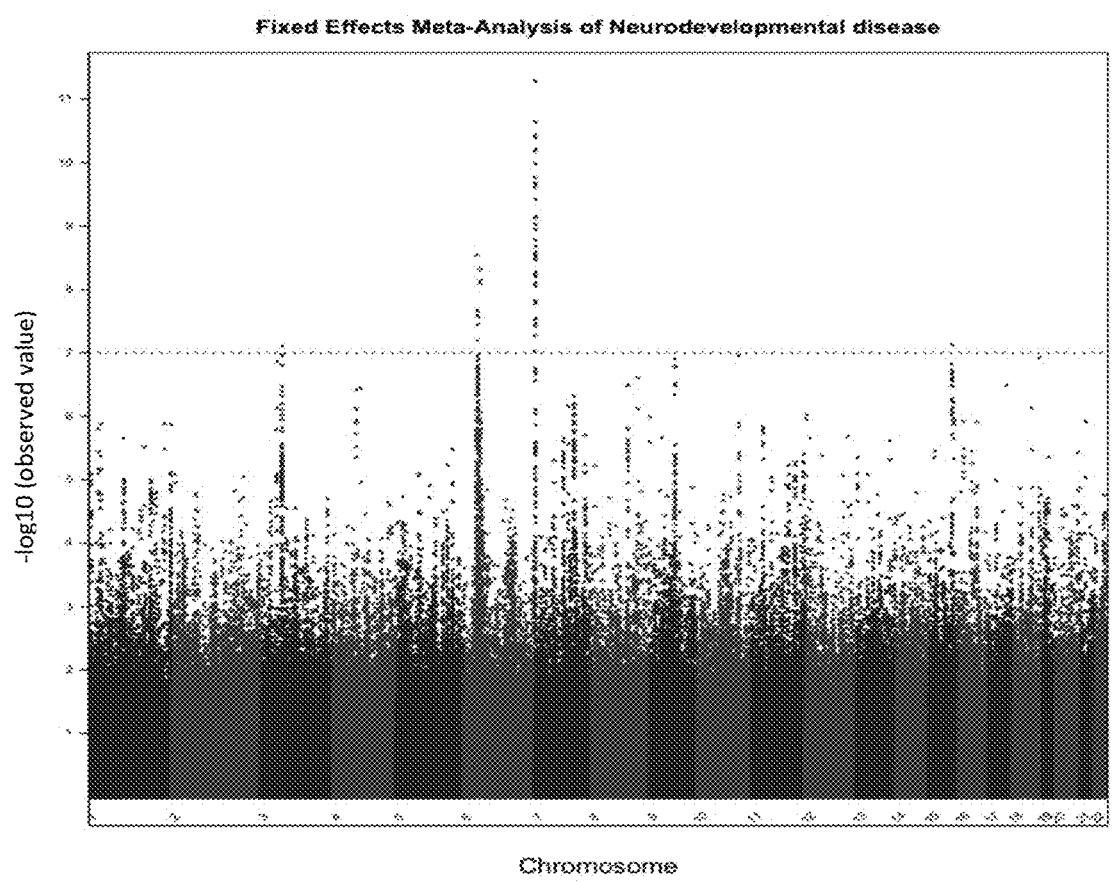
FIG. 2 shows Manhattan plot of SCZ-BP-ASD datasets meta-analysed, using a heterogeneity filter >0.05.

We have total of 18,069 schizophrenia, bipolar and autism samples together with 47,440 control samples, all with GWAS data and were meta-analyzed together. See the Manhattan plots shown in FIGS. 1 and 2. We identified several genome wide significant loci on chromosomes 15, 8, and 7.

Genome-wide Significant Loci

Chr15q25.2 neuromedin B—novel
  Neuropeptide, associated with obesity and eating behavior.
  Association between SCZ and obesity reported by Kraepelin as early as 1919. 40-60% of SCZ population obese.
chr8q24.3 TSNARE1—novel
  SNARE domain containing protein
chr7p22.3 MAD1L1—not previously GWS
  MAD1L1 is a component of the mitotic spindle-assembly checkpoint that prevents the onset of anaphase until all chromosomes are properly aligned at the meta phase plate
  NUDT1 Misincorporation of oxidized nucleoside triphosphates into DNA/RNA during replication and transcription can cause mutations that may result in carcinogenesis or neurodegeneration. The protein encoded by this gene is an enzyme that hydrolyzes oxidized purine nucleoside triphosphates, such as 8-oxo-dGTP, 8-oxo-dATP, 2-hydroxy-dATP, and 2-hydroxy rATP to mono phosphates, thereby preventing misincorporation. The encoded protein is localized mainly in the cytoplasm, with some in the mitochondria, suggesting that it is involved in the sanitization of nucleotide pools both for nuclear and mitochondrial genomes.

chr6p22.1 MHC Locus previously associated with SCZ, BP and mood disorders.
chr3p21.1 PBRM1/ITIH3 Locus previously associated with SCZ, BP and mood disorders.
chr1q43 SDCCAG8 Locus previously associated with SCZ BP and mood disorders not associated with autism.

Figure 3:
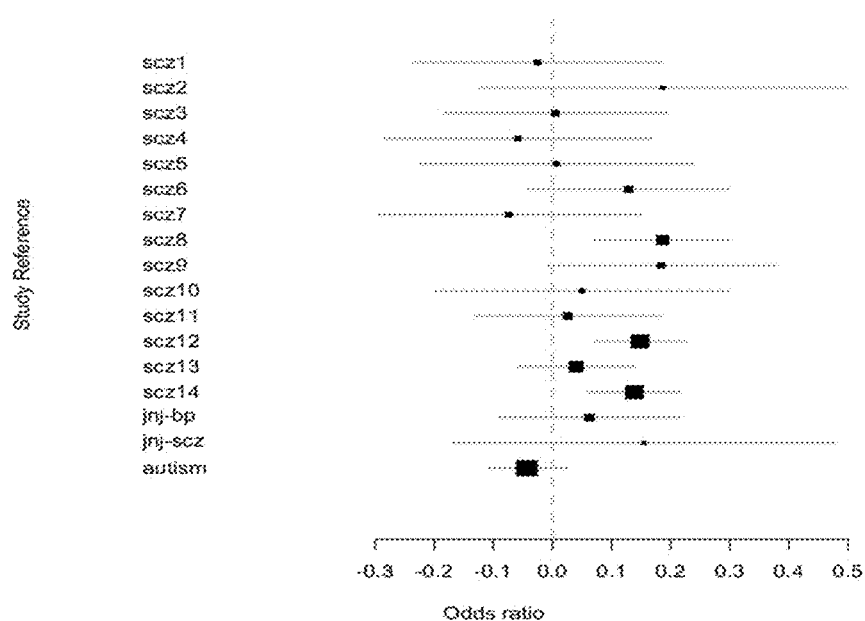
FIG. 3. Chr3 beta forest plot delineating individual studies and significance of the association.
Figure 4:
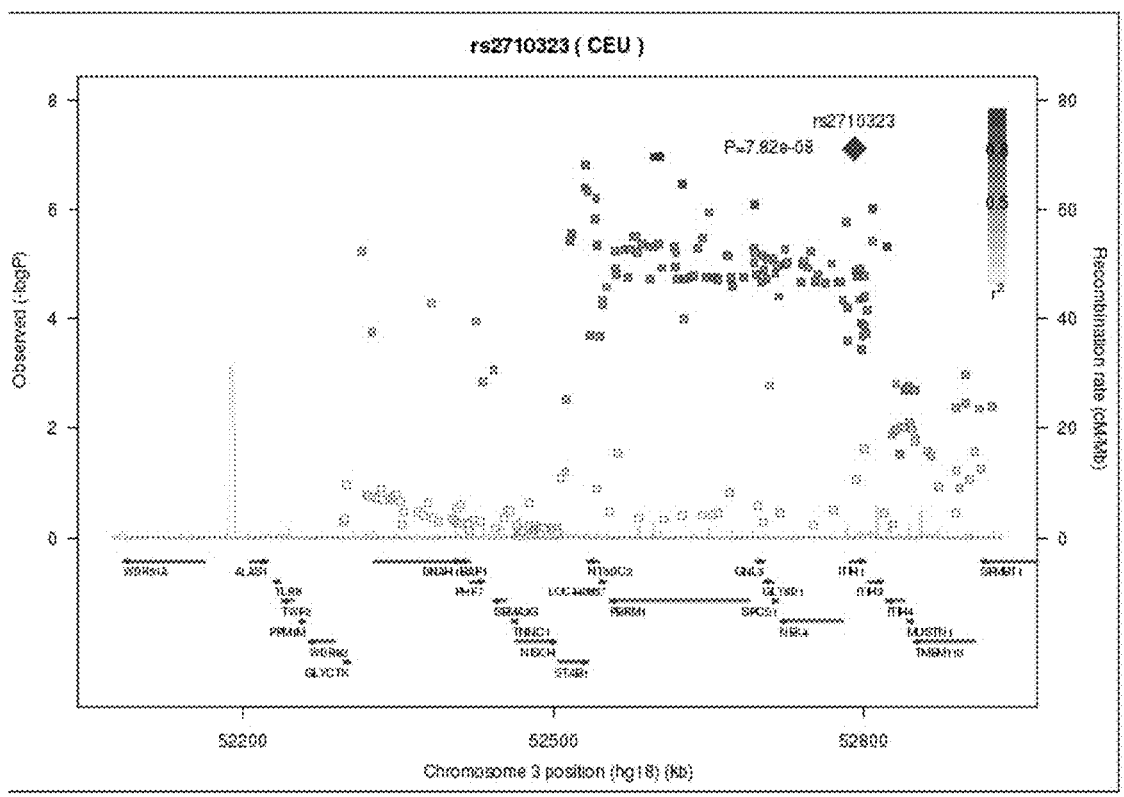
FIG. 4. Chr3 regional association plot. The association signal spans multiple genes.

We also identified several targets on chromosome 3. See FIGS. 3 and 4. These targets included The CACNA1D (calcium channel, voltage-dependent, L type, alpha 1D subunit) gene—a member of the CACN family of genes showing significance in previous CNV analyses. Other genes in the region that potentially also associate include: NT5DC2 5'-nucleotidase domain containing 2; ITH1 *Homo sapiens* inter-alpha-trypsin inhibitor heavy chain 1; NEK4 NIMA (never in mitosis gene a)-related kinase 4 (NEK4), transcript variant 2; GNL3 guanine nucleotide binding protein-like 3; PB1 polybromo 1 isoform 4; and GLT8D1 Glycosyltransferase 8 domain-containing protein 1.

Figure 5:
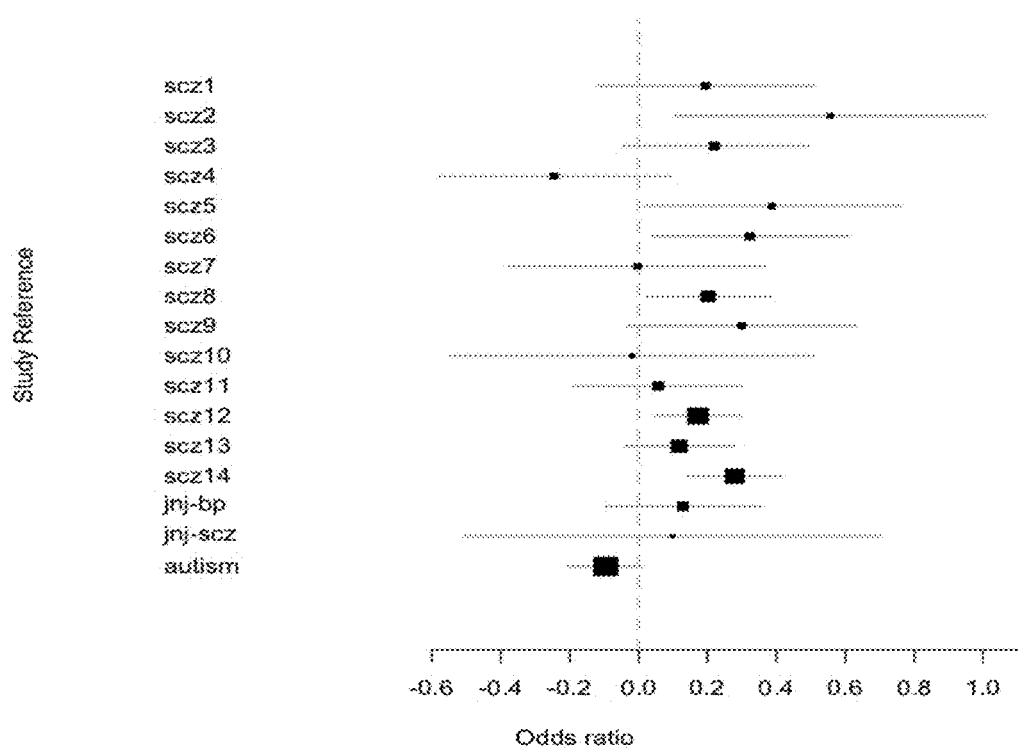
FIG. 5 shows a forest plot for the associated region on chr 6, followed by association plot for the region (FIG. 6).
Figure 6:
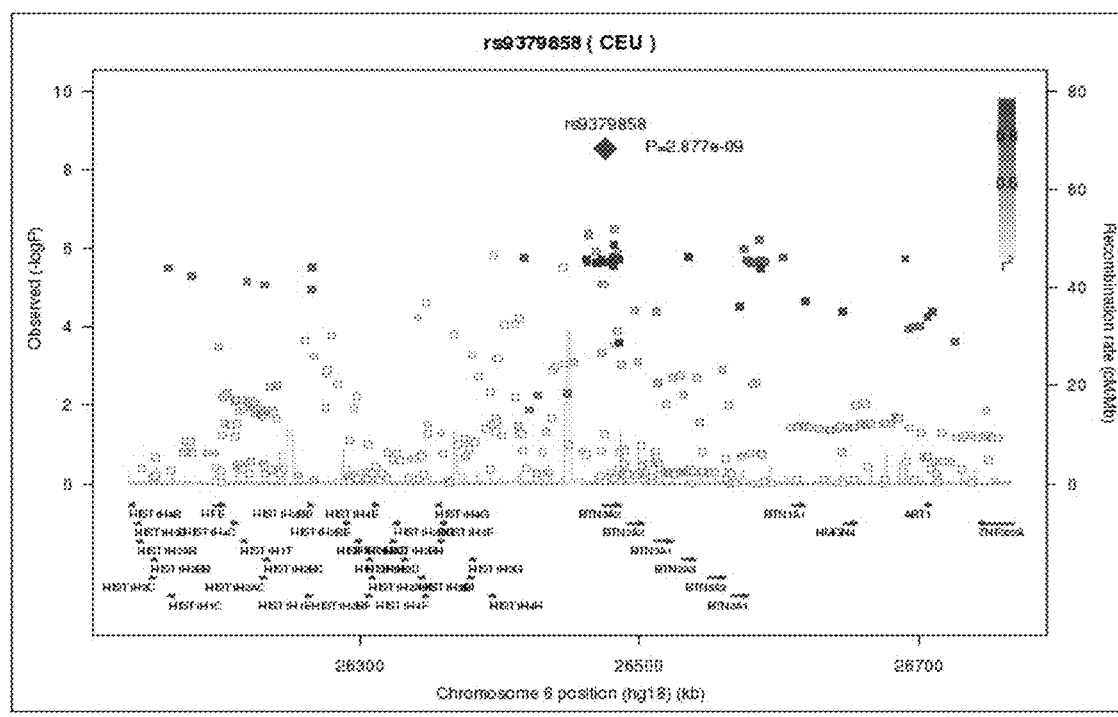
FIG. 6. Chr6 regional association plot. The association signal spans across the MHC locus.

We also identified targets on chromosome 6. See FIGS. 5 and 6.

Figure 7:
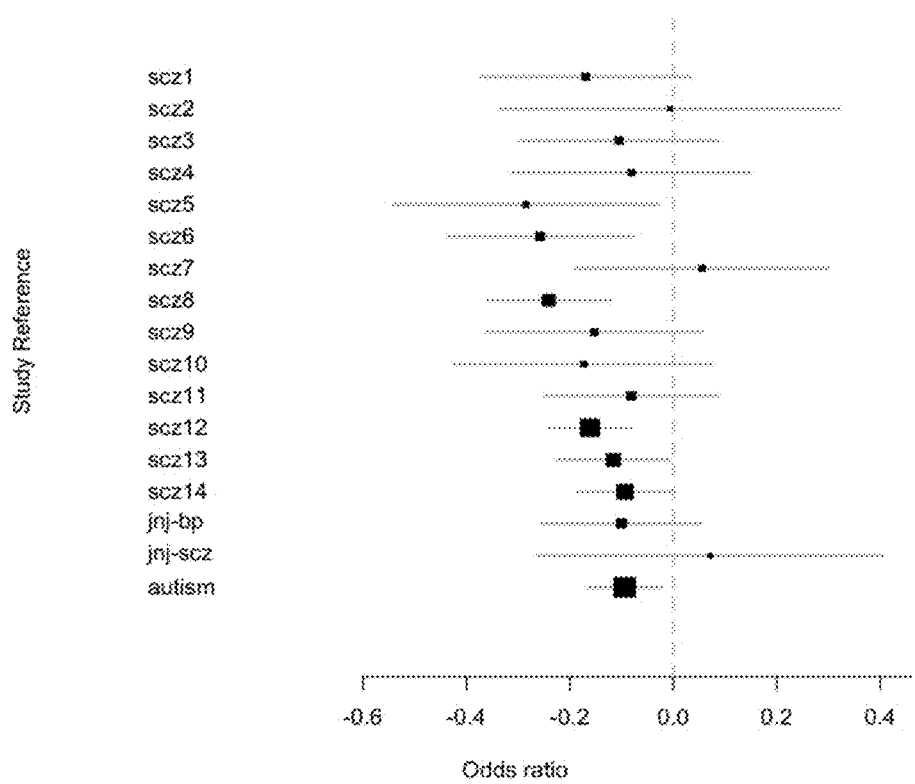
FIG. 7. Chr7 beta forest plot delineating individual studies and significance of the association.
Figure 8:
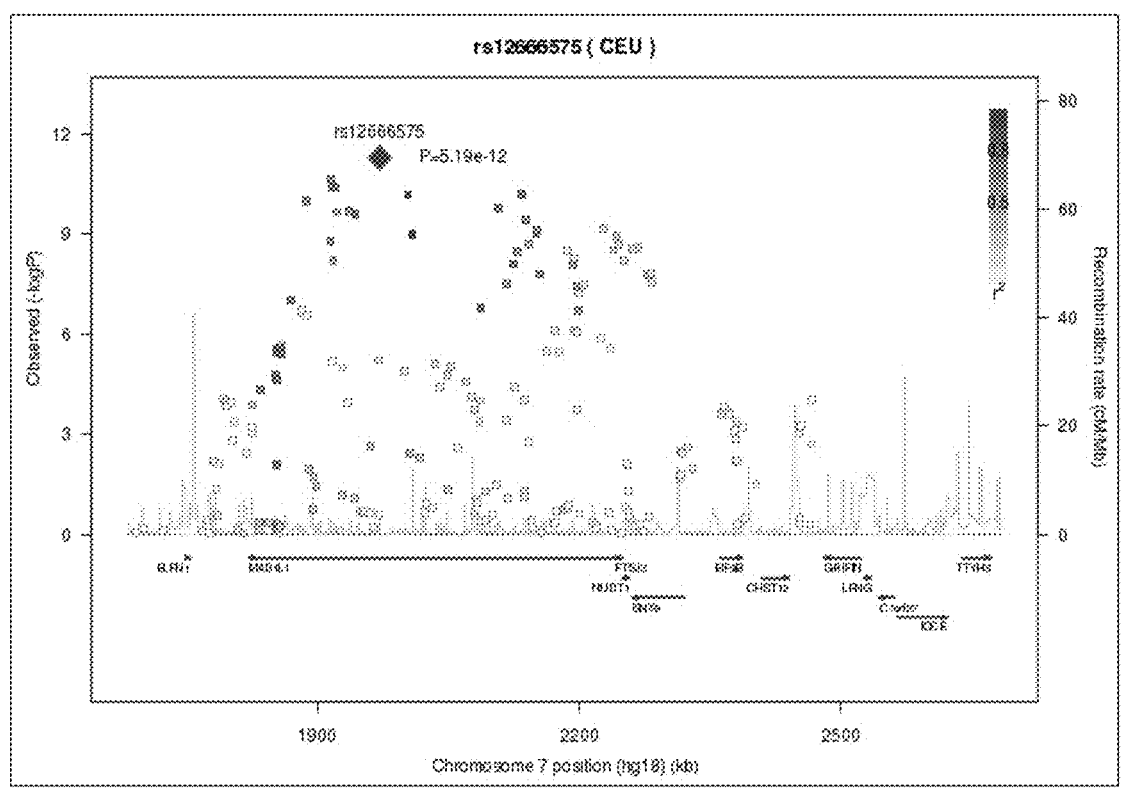
FIG. 8. Chr7 regional association plot.

Several targets were identified on chromosome 7. See FIGS. 7 and 8. These genes include MAD1L1 Mitotic spindle assembly checkpoint protein MAD1; FTSJ2 S-adenosylmethionine-binding protein involved in processing and modification of rRNA; NUDT1 nudix-type motif 1 involved in the sanitization of nucleotide pools both for nuclear and mitochondrial genomes; and sorting nexin 8 (SNX8) involved in several stages of intracellular trafficking.

Figure 9:
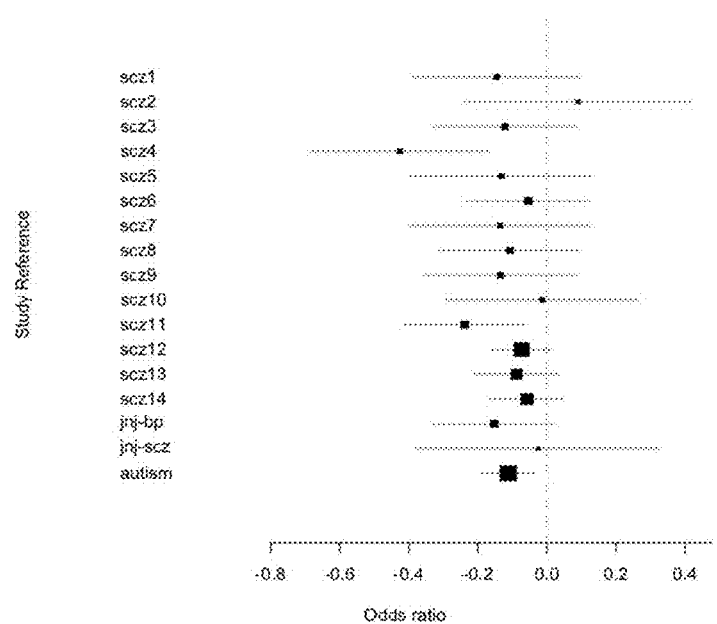
FIG. 9. Chr15 beta forest plot delineating individual studies and significance of the association.
Figure 10:
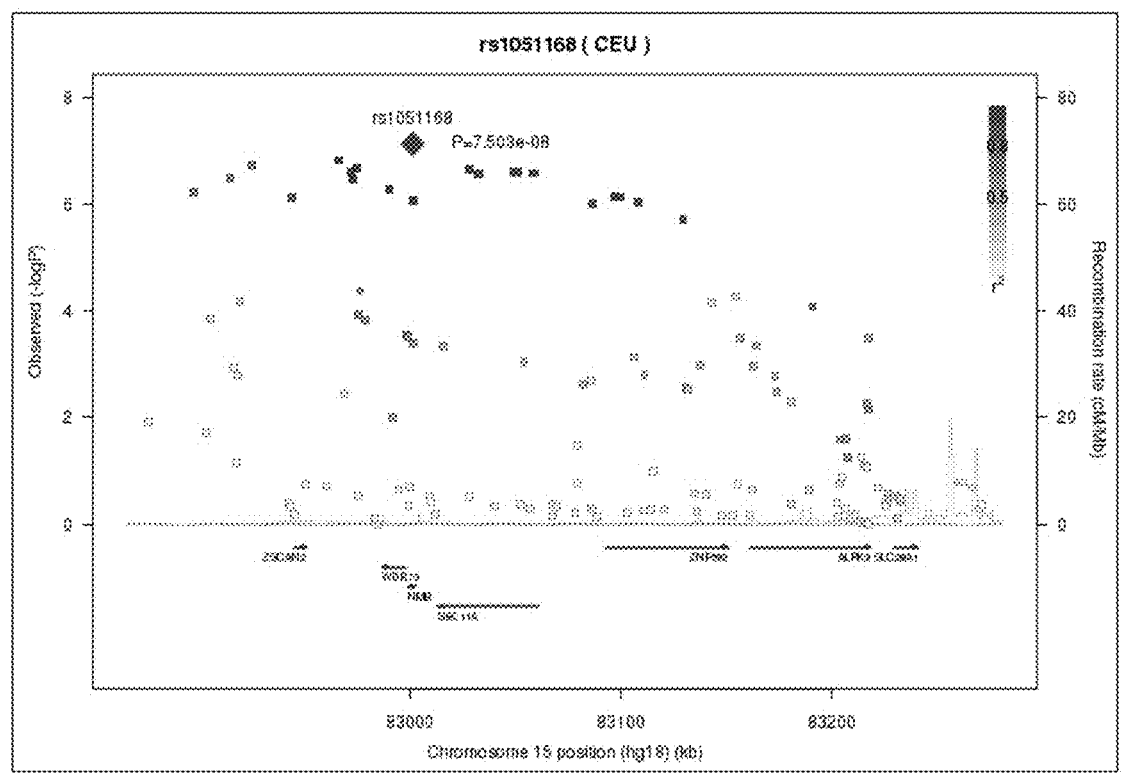
FIG. 10. Chr15 regional association plot.

Finally targets were also identified on chromosome 15. See FIGS. 9 and 10. The association signal on chromosome 15 spans several genes, including NMB neuromedin B (bombesin) which can signal satiety and modulate 5-HT. Other genes in the associated regio include SEC11A signal peptidase; SCAND2 non coding RNA; ZSCAN2 zinc finger protein 29 transcriptional regulation; ALPK3 alpha-kinase 3; and PDE8A phosphodiesterase 8A which hydrolyzes the second messenger cAMP.

All of these genes provide targets for screening assays to identify therapeutic agents for the treatment of neurological disorders. Taken together, we have identified 7 genome-wide significant loci, two of which are novel (chr15q25.2 containing neuromedin B, and chr8q24.3 TSNARE1, containing SNARE domain containing protein) and a third (chr1 q43 SDCCAG8), which has been reported to be associated with schizophrenia and bipolar disease, but we show for the first time is also associated with autism.

Current pharmacological treatment of schizophrenia is limited to the typical and atypical antipsychotics, which almost exclusively targeted dopamine and serotonin receptors. Our inventions yield new insights in to the genetics of schizophrenia and neuropsychiatric diseases and new targets for therapeutic and diagnostic developments and products.

EXAMPLE II

A meta analysis of 13,394 schizophrenia and biploar cases and 34,676 controls, from 16 cohorts, was carried out to identify novel psychosis susceptibility loci. Following meta analysis, 40 variants at 6 loci surpassed genome wide significance. Five of the 6 loci have been associated with SCZ or BP. Two of the genome wide significant variants that mapped to one locus, TSNARE1, had not previously been shown to associate with either schizophrenia or bipolar disorder. The function of TSNARE1 is unclear, however, bio-informatic predictions based on phylogenetic ancestry indicate it may have a vertebrate specific function in intracellular protein transport and synaptic vesicle exocytosis.

Methods

Study Cohorts. The study included 13,394 schizophrenia and bipolar cases and 34,676 controls (Table 1) including 3,182 schizophrenia cases and 1,032 bipolar cases collected from 28 clinical trials conducted by Janssen Research & Development, LLC, these were matched to 15,277 and 8,000 controls respectively from the Children's Hospital of Philadelphia (CHOP). All JNJ cases were genotyped on the Illumina 1M and CHOP controlson either the Illumina HH550 or 610 Quad arrays.

In addition, 351 schizophrenia cases and 2,107 control subjects from the University of Pennsylvania (UPenn) were included, along with 806 schizophrenia cases from Mount Sinai School of Medicine and Sheba Medical Center. Both cohorts were genotyped on the Affymetrix 6.0 array at The Children's Hospital of Philadelphia (CHOP) as previously described (1). The remaining 8,023 schizophrenia cases and 9,292 controls formed part of the Schizophrenia Psychiatric Genome-Wide Association Study Consortium (PGC), as previously described (2), and were downloaded from the NIMH website as schizophrenia distribution 9 (www.nimhgenetics.org/).

TABLE 1

| Collection | Case | Control | Platform |
|---|---|---|---|
| JNJ SCZ/CHOP control | 3182 | 15277 | Illumina 1M/Illumina 550K |
| PGC MGS2 | 2681 | 2653 | Affymetrix 6.0 |
| UPENN/MS | 1157 | 2107 | Affymetrix 6.0 |
| JNJ BP/CHOP control | 1032 | 8000 | Illumina 1M/Illumina 550K |
| PGC Aberdeen | 720 | 699 | Affymetrix 5.0 |
| PGC UCLA | 705 | 637 | Illumina 550K |
| PGC Bulgaria | 527 | 609 | Affymetrix 6.0 |
| PGC UCL | 521 | 494 | Affymetrix 5.0 |
| PGC Cardiff/58BC | 475 | 1494 | Affymetrix 500K |
| PGC catie | 410 | 391 | Affymetrix 500K |
| PGC Sweden 1&2 | 558 | 396 | Affymetrix 5.0/Affymetrix 6.0 |
| PGC Edinburgh | 368 | 284 | Affymetrix 6.0 |
| PGC Potugal | 346 | 216 | Affymetrix 5.0 |
| PGC Dublin | 272 | 860 | Affymetrix 6.0 |

TABLE 1-continued

| Collection | Case | Control | Platform |
|---|---|---|---|
| PGC TOP3 (Norway) | 248 | 369 | Affymetrix 6.0 |
| PGC Zucker Hillside | 192 | 190 | Affymetrix 500K |
| Total | 13394 | 34676 | |

Description of JNJ Samples.

The unrelated schizophrenia (SZ), schizoaffective (SA), or bipolar I (BP) patients were from 28 clinical trials (Table 1) conducted by Janssen Research & Development, LLC to assess the efficacy and safety of risperidone, paliperidone and an investigative compound (R209130). The diagnoses of SZ, SA, and BP were based on clinician rated DSM IV criteria. Detailed descriptions of these clinical trials can be found at ClinicalTrials.gov as well as in published works (4-33) thus are not repeated here.

A total of 5544 DNA samples from 5431 patients and 49 quality control (QC) samples were genotyped on the Illumina Human1M-Duo. DNA samples from all patients who participated in these clinical trials and consented to the genetic study were genotyped for 21 out of the 28 clinical trials. A small number of DNA samples from the remaining 7 clinical trials were also genotyped (Table 2). The DNA samples were genotyped in 2 batches, with 3102 samples in the first batch and 2491 samples in the second batch. Genotype data were successfully generated on 5508 samples. A few sample QC steps were performed to remove the duplicated and/or problematic samples. First, gender discrepancies were examined using both the heterozygosity rate of the X-chromosome SNPs and the call rate of the Y-chromosome SNPs. Samples with discrepant and ambiguous gender information were excluded. Second, the relatedness of the genotyped samples was examined using pairwise Identity-by-State. Planned but not confirmed duplicates as well as unplanned duplicates with discrepant phenotype data were excluded from subsequent analyses. For each pair of samples that were planned and confirmed duplicates, unplanned duplicates with consistent phenotype data, or samples of related individuals, the sample with a smaller standard deviation of the Log R-ratio (LRR) was retained. After the sample QC, there were 4962 samples (3251 SZ, 377 SA, and 1334 BP) remaining Table 3 summarizes the basic demographic information of these patients.

TABLE 2

Summary of the JNJ clinical trials.

| Trial | Trial ID | Clinical-Trials.gov Identifier | Drug* | Disease | # of Patients Genotyped | All Samples Genotyped | Genotyping Batch | Publication | PMID |
|---|---|---|---|---|---|---|---|---|---|
| R076477-SCH-101 | CR004273 | NCT00791232 | Pali ER, Ris | SZ | 1 | No | 1 | (4) | |
| R076477-SCH-301 | CR004384 | NCT00086320 | Pali ER, Pbo | SZ | 187 | Yes | 1 | (5) | 17224706 |
| R076477-SCH-302 | CR004381 | NCT00085748 | Pali ER, Pbo | SZ | 93 | Yes | 1 | (6) | 18165460 |
| R076477-SCH-303 | CR003379 | NCT00078039 | Pali ER, Olz, Pbo | SZ | 473 | Yes | 1 | (7), (10) | 17092691, 18466043 |
| R076477-SCH-304 | CR004378 | NCT00077714 | Pali ER, Olz, Pbo | SZ | 296 | Yes | 1 | (8), (10) | 17601495, 18466043 |
| R076477-SCH-305 | CR004375 | NCT00083668 | Pali ER, Olz, Pbo | SZ | 333 | Yes | 1 | (9), (10) | 17466492, 18466043 |
| R076477-SCH-3015 | CR010501 | NCT00334126 | Pali ER, Quet | SZ | 220 | Yes | 1 | (11) | 19411369 |
| R076477-SCA-3001 | CR010498 | NCT00397033 | Pali ER, Pbo | SA | 173 | Yes | 2 | (12, 14) | 20492853, 20957127 |

TABLE 2-continued

Summary of the JNJ clinical trials.

| Trial | Trial ID | Clinical-Trials.gov Identifier | Drug* | Disease | # of Patients Geno-typed | All Samples Geno-typed | Geno-typing Batch | Publica-tion | PMID |
|---|---|---|---|---|---|---|---|---|---|
| R076477-SCA-3002 | CR013099 | NCT00412373 | Pali ER, Pbo | SA | 187 | Yes | 2 | (13, 14) | 20814330, 20957127 |
| R076477-BIM-3001 | CR010834 | NCT00299715 | Pali ER, Pbo | BP | 310 | Yes | 2 | (15) | 20624657 |
| R076477-BIM-3002 | CR010858 | NCT00309699 | Pali ER, Quet, Pbo | BP | 350 | Yes | 2 | (16) | 20565430 |
| R076477-BIM-3003 | CR010855 | NCT00309686 | Pali ER, Pbo | BP | 214 | Yes | 2 | (17) | 20947174 |
| R092670-SCH-201 | CR004357 | NCT00074477 | Pali Palm, Pbo | SZ | 168 | Yes | 1 | (18) | 19941696 |
| R092670-PSY-3001 | CR004198 | NCT00111189 | Pali Palm, Pbo | SZ | 14 | No | 1 | (19), (20) | 19959339, 21696265 |
| R092670-PSY-3002 | CR004195 | NCT00210717 | Pali Palm, Consta | SZ | 493 | Yes | 1 | (21) | 21777507 |
| R092670-PSY-3003 | CR002353 | NCT00210548 | Pali Palm, Pbo | SZ | 249 | Yes | 1 | (22) | 20389255 |
| R092670-PSY-3004 | CR003562 | NCT00101634 | Pali Palm, Pbo | SZ | 404 | Yes | 1 | (23) | 20555312 |
| R092670-PSY-3005 | CR002350 | NCT00119756 | Pali Palm | SZ | 17 | No | 1 | (24) | 19481579 |
| R092670-PSY-3007 | CR012550 | NCT00590577 | Pali Palm, Pbo | SZ | 468 | Yes | 2 | (25), (26) | 20473057, 21569242 |
| RIS-SCH-401 | CR002899 | NCT00297388 | Ris | SZ or SA | 148 | Yes | 2 | (27) | 16965196 |
| RIS-SCP-402 | CR002890 | NCT00061802 | Ris, Pbo | SZ or SA | 62 | Yes | 1 | (28) | 17054789 |
| RIS-BIM-301 | CR003631 | NCT00076115 | Ris, Pbo | BP | 120 | Yes | 2 | (29) | 19839994 |
| RIS-INT-85 | | | Ris | SZ | 8 | No | 1 | (30) | 15201572 |
| RIS-INT-69 | CR006049 | NCT00253162 | Ris, Halo, Pbo | BP | 233 | Yes | 1 | (31) | 15572276 |
| RIS-USA-239 | CR006052 | NCT00257075 | Ris, Pbo | BP | 186 | Yes | 2 | (32) | 15169694 |
| RIS-USA-259 | CR002761 | NCT00034775 | Ris | SZ | 16 | No | 1 | (33) | 15323593 |
| R209130-SCH-201 | | | R209130, Pbo | SZ | 7 | No | 1 | | |
| R209130-SCH-202 | CR004342 | NCT00063297 | R209130, Pbo | SZ | 1 | No | 1 | | |

*Pali ER: Paliperidone ER OROS; Pali Palm: PaliperidonePalmitate; Ris: Risperidone; Consta: Risperdal Consta; Olz: Olanzapine; Quet: Quetiapine; Halo: Haloperidol; Pbo: Placebo

TABLE 3

Basic demographic information of the JNJ SZ, SA, and BP patients

| | Schizophrenia (N = 3251) | Schizoaffective (N = 377) | Bipolar (N = 1344) |
|---|---|---|---|
| Sex, n (%) | | | |
| F | 1240 (38.1) | 152 (40.3) | 629 (47.2) |
| M | 2011 (61.9) | 225 (59.7) | 705 (52.8) |
| Age, years | | | |
| Mean (SD) | 40.2 (12) | 38.7 (9.5) | 37.8 (13.5) |
| Median (Range) | 40 (17, 81) | 39 (19, 61) | 39 (10, 77) |
| Race, n (%) | | | |
| Asian | 117 (3.6) | 52 (13.8) | 37 (2.8) |
| Black or African America | 703 (21.6) | 86 (22.8) | 247 (18.5) |
| White | 2360 (72.6) | 228 (60.5) | 1021 (76.5) |
| Other | 71 (2.2) | 11 (2.9) | 29 (2.2) |

Preliminary Quality Control. For each cohort, we excluded from further analysis any sample that had missing genotypes for more than 2% of the SNPs on the array, further we only included SNPs with genotype missing rate <5%, minor allele frequency >0.01, as well as HWE-pvalue >0.0001.

Duplicate Samples and Cryptic Relatedness. We generated pairwise IBD values for all samples using the plink genome command, excluding one sample from any pair with a PI_HAT value exceeding 0.3.

Population Stratification. Principal components were generated on each cohort using smartPCA, eigenvectors were included as covariates in a logistic regression to control for population stratification as required. To determine the genomic inflation for each case control set we carried an association analysis on the genotyped data using plink prior to imputation. If genomic inflation exceeded 1.03, principal components were included as covariates in the post-imputation GWAS.

Prephasing. For each cohort, samples were prephased for imputation using the SHAPEIT package. Each chromosome was prephased separately. For case control sets that were typed on different arrays, such as the Johnson and Johnson and CHOP set, the prephasing was carried for each chip type separately and prior to imputation the haplotypes were restricted to SNPs common to both arrays.

Imputation. We used the Impute2 package to impute unobserved genotypes in each cohort using the reference haplotypes in release 2 of the HapMap 3 that included approximately 1.5 million variants from 1,011 individuals from Africa, Asia, Europe and the Americas.

Genotype Concordance. Internal cross validation was carried out automatically by Impute2, the calculation is performed by masking one variant at a time in the study data, imputing the masked variant and comparing the result to the original genotype. Average concordance for all datasets was >90%.

Post-imputation Association Analysis. Case control association was carried out using the snptest package. We applied an additive model on the genotype dosages generated by Impute2 including the proportion of missing data and gender were as covariates for all cohorts. In the presence of population stratification, we also included the first 10 principal components from the smartPCA analysis as covariates.

Meta Analysis. Inverse variance fixed effects meta analysis was carried out using the metal package controlling for genomic inflation during the meta analysis. A final round of genomic control was also applied to the results of the meta analysis. Random effects meta analysis was carried out using the RE2 model in the METASOFT package.

Results

Figure 11:
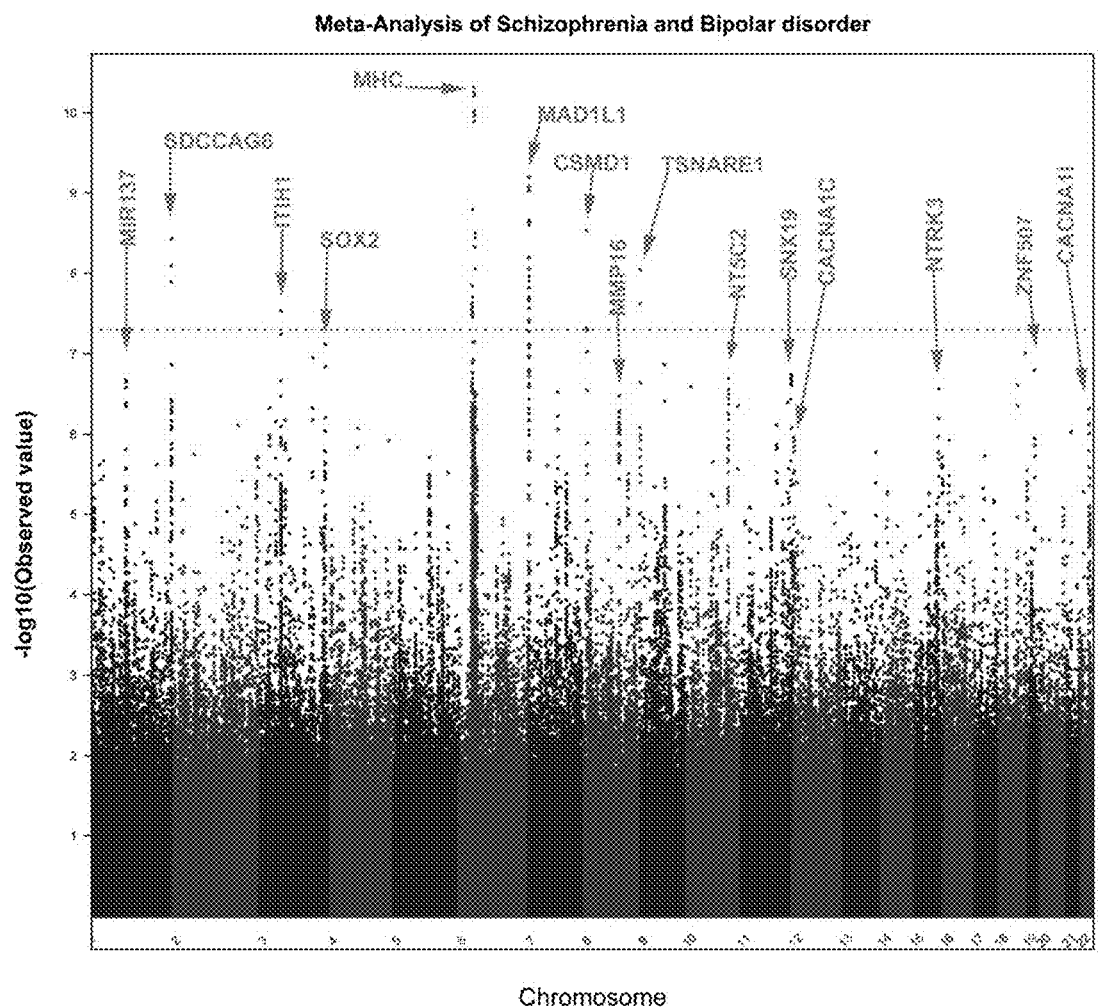
FIG. 11. Manhattan plot of the SCZ-BP meta-analysis. The dotted line indicates genome wide significance threshold.
Figure 12:
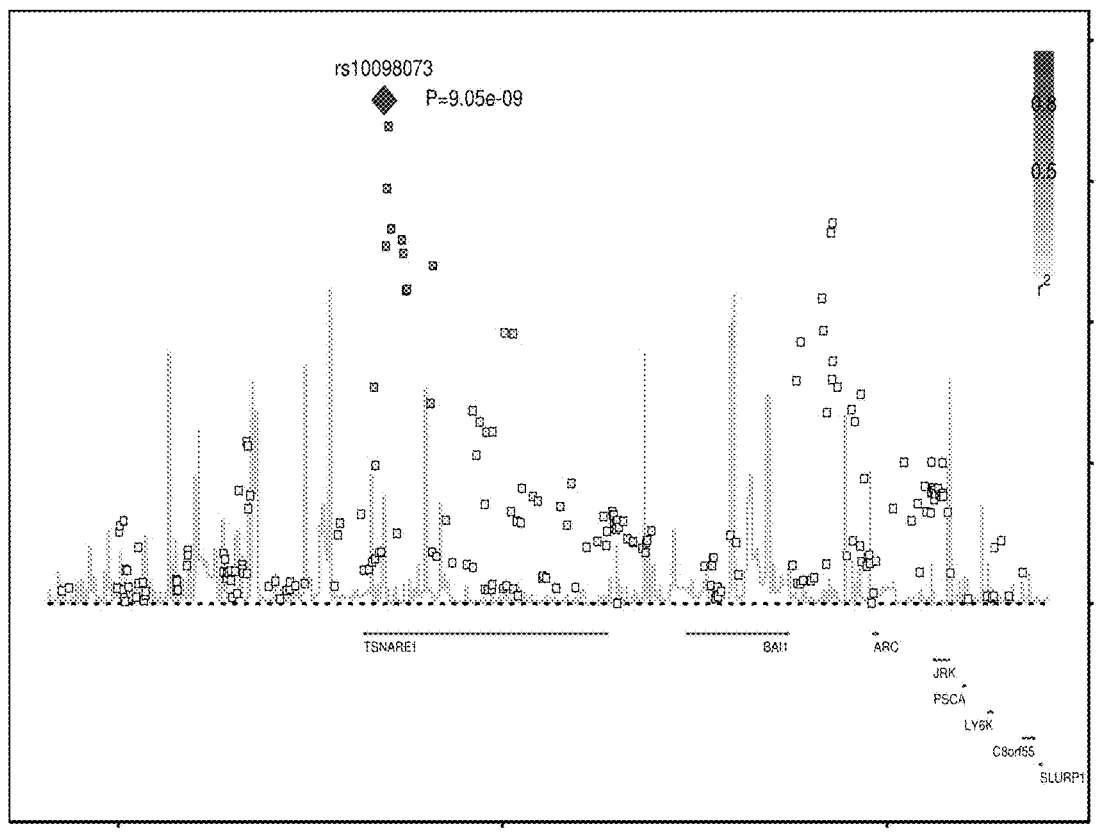
FIG. 12. TSNARE1 regional association plot.
Figure 13:
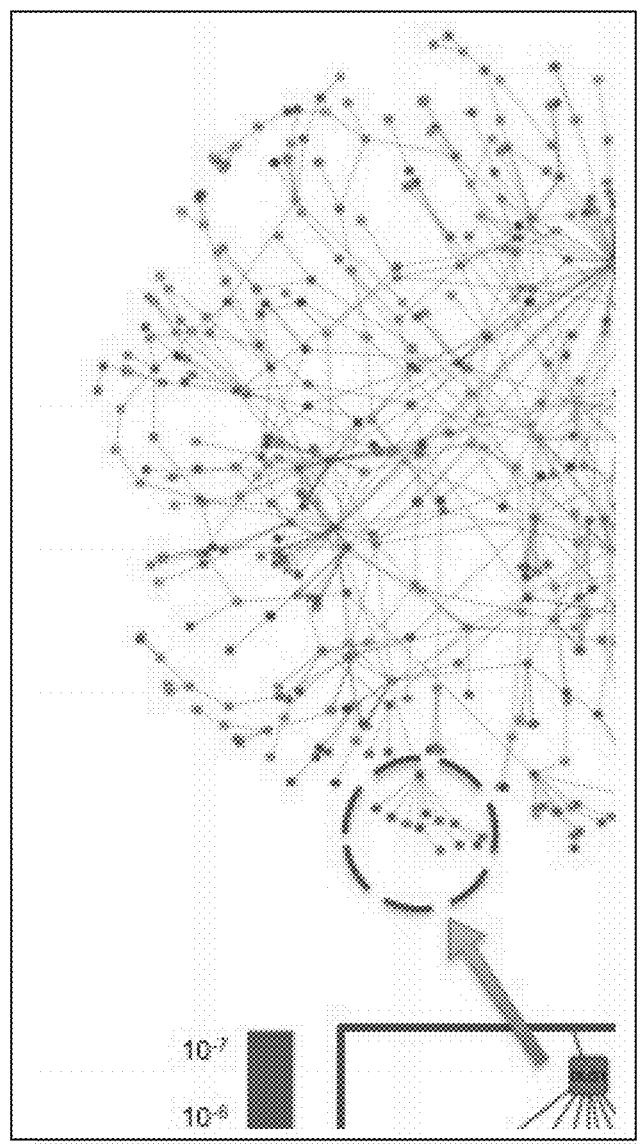
FIG. 13. The overall LCC with the DLG1 mediated sub-network corresponding to the post-receptor segment of the NR pathway circled and boxed. Gene-wise P-value significance denoted on a green to red color scale. Circled nodes are genes with SNPs that had P-values <1×10-3; all others are boxed.

Following the meta analysis 40 variants remained significant after Bonferroni correction (P-values $<5 \times 10^{-8}$) (Table 4). The 40 SNPs mapped to 6 loci, 5 of which had been previously associated with susceptibility to SCZ and/or BP (FIG. 11). Two SNPs mapped to a novel locus containing a gene of unknown function, TSNARE1 (t-SNARE domain containing 1) which maps to chr8q24.3. In addition to the two genome-wide significant SNPs multiple other SNPs in LD showed a trend towards association at the locus (FIG. 12). Odds ratios for the most significantly associated SNP (rs10098073, P-value $9.05 \times 10^{-9}$) across the 16 cohorts ranged from 0.76 to 0.99 (SD 0.06) with one outlier, the Dublin cohort, crossing 1 at 1.02.

While the function of the TSNARE1 gene remains unknown, a recent publication suggests it may have evolved, within the vertebrate lineage, from the harbinger transposon superfamily (3). Bio-informatic predictions based on phylogenetic ancestry indicate it may bind SNARE (soluble N-ethylmaleimide-sensitive factor attached protein receptor) proteins and have SNAP receptor activity. TSNARE1 may therefore have a vertebrate specific function in intracellular protein transport and synaptic vesicle exocytosis.

TABLE 4

Genome wide significant variants following SCZ meta analysis.

| Gene | rsID | CHR | BP (hg17) | Freq | Pval | Direction effect | A1 | A2 | HetPVal |
|---|---|---|---|---|---|---|---|---|---|
| SDCCAG8 | rs10927013 | 1 | 241655779 | 0.4368 | $8.09 \times 10^{-9}$ | ++++++++++++++++ | G | T | 0.91 |
| | rs2039839 | 1 | 241665293 | 0.5645 | $1.28 \times 10^{-8}$ | ---------------- | A | G | 0.93 |
| | rs6703335 | 1 | 241675590 | 0.5627 | $3.71 \times 10^{-9}$ | ---------------+ | A | G | 0.91 |
| ITIH1 | rs2710323 | 3 | 52790945 | 0.4669 | $2.97 \times 10^{-8}$ | -++-++-+++++++++ | C | T | 0.39 |
| MHC | rs9379858 | 6 | 26475668 | 0.1069 | $1.42 \times 10^{-8}$ | +++-++-++-++++++ | C | T | 0.35 |
| | rs3799380 | 6 | 26575161 | 0.2201 | $2.80 \times 10^{-8}$ | +++-++-++++++++ | C | T | 0.82 |
| | rs6456728 | 6 | 26585758 | 0.7797 | $2.36 \times 10^{-8}$ | ---+---+--------- | A | G | 0.82 |
| | rs7749305 | 6 | 27554545 | 0.1004 | $2.57 \times 10^{-8}$ | +++-++++++++++++ | C | T | 0.29 |
| | rs6904596 | 6 | 27599278 | 0.8963 | $3.06 \times 10^{-8}$ | ---+------------ | A | G | 0.27 |
| | rs17750424 | 6 | 27809101 | 0.0847 | $1.99 \times 10^{-8}$ | ++++++++++++++++ | C | T | 0.38 |
| | rs17693963 | 6 | 27818144 | 0.9034 | $1.61 \times 10^{-9}$ | +++-++++++++++++ | A | C | 0.36 |
| | rs34706883 | 6 | 27913234 | 0.9096 | $3.14 \times 10^{-8}$ | ++++++++++++++++ | A | C | 0.39 |
| | rs13212651 | 6 | 27914964 | 0.9096 | $3.34 \times 10^{-8}$ | ++++++++++++++++ | A | G | 0.39 |
| | rs13194781 | 6 | 27923618 | 0.9095 | $3.51 \times 10^{-8}$ | ++++++++++++++++ | A | G | 0.42 |
| | rs13199772 | 6 | 27942064 | 0.9096 | $3.40 \times 10^{-8}$ | ++++++++++++++++ | A | G | 0.42 |
| MAD1L1 | rs10275045 | 7 | 1887352 | 0.4035 | $2.16 \times 10^{-8}$ | -+-+-------+---+ | C | T | 0.36 |
| | rs12537914 | 7 | 1914885 | 0.3647 | $2.03 \times 10^{-8}$ | -+-+-------+---- | C | T | 0.47 |
| | rs4721184 | 7 | 1917310 | 0.3698 | $2.74 \times 10^{-8}$ | +-+-++++++-+++- | C | T | 0.47 |
| | rs2056480 | 7 | 1920827 | 0.6321 | $1.54 \times 10^{-8}$ | ---+-------+---+ | A | G | 0.56 |
| | rs4721190 | 7 | 1921258 | 0.5959 | $3.83 \times 10^{-8}$ | ---+-------+---+ | A | G | 0.69 |
| | rs12699477 | 7 | 1935479 | 0.3523 | $8.78 \times 10^{-9}$ | +-++++++++-++++ | C | T | 0.67 |
| | rs2280550 | 7 | 1943082 | 0.6389 | $3.80 \times 10^{-8}$ | -+-+-------+---+ | A | G | 0.49 |
| | rs12666575 | 7 | 1970947 | 0.3578 | $8.27 \times 10^{-10}$ | ------+----+---+ | C | T | 0.19 |
| | rs4721295 | 7 | 2003195 | 0.3778 | $6.23 \times 10^{-10}$ | +-++++-++++-+++ | G | T | 0.07 |
| | rs1107592 | 7 | 2007958 | 0.62 | $5.64 \times 10^{-9}$ | +-++++-++++-+++- | A | G | 0.04 |
| | rs3778969 | 7 | 2106516 | 0.6329 | $6.43 \times 10^{-9}$ | ------+----+---+ | A | G | 0.16 |
| | rs10224497 | 7 | 2116493 | 0.5742 | $1.09 \times 10^{-8}$ | ++++++-++++-+++- | A | G | 0.13 |
| | rs10239050 | 7 | 2124916 | 0.6149 | $1.11 \times 10^{-8}$ | +-++++-++++-+++- | A | G | 0.12 |
| | rs3800913 | 7 | 2129763 | 0.6036 | $4.03 \times 10^{-8}$ | ++++++-++++-+++- | A | G | 0.15 |
| | rs3800917 | 7 | 2134465 | 0.64 | $2.29 \times 10^{-9}$ | -+-----+----+---+ | A | G | 0.22 |

TABLE 4-continued

Genome wide significant variants following SCZ meta analysis.

| Gene | rsID | CHR | BP (hg17) | Freq | Pval | Direction effect | A1 | A2 | HetPVal |
|---|---|---|---|---|---|---|---|---|---|
|  | rs3778991 | 7 | 2138981 | 0.656 | $2.21 \times 10^{-9}$ | ------+----+---- | A | G | 0.20 |
|  | rs3778994 | 7 | 2142381 | 0.6165 | $2.53 \times 10^{-9}$ | ------+----+---- | A | C | 0.21 |
|  | rs4721441 | 7 | 2150586 | 0.3564 | $9.41 \times 10^{-10}$ | ++++++-++++-++++ | C | T | 0.29 |
|  | rs3779003 | 7 | 2151428 | 0.3471 | $2.33 \times 10^{-9}$ | ------+----+---- | C | T | 0.23 |
|  | rs3757440 | 7 | 2239462 | 0.647 | $1.98 \times 10^{-8}$ | ++++++++++--+++- | A | G | 0.28 |
|  | rs7787274 | 7 | 2242519 | 0.6506 | $1.08 \times 10^{-8}$ | ------------+---+ | A | G | 0.21 |
|  | rs7799006 | 7 | 2244752 | 0.3503 | $1.24 \times 10^{-8}$ | ------------+---+ | C | T | 0.23 |
| CSMD1 | rs6558872 | 8 | 4225547 | 0.5707 | $4.75 \times 10^{-8}$ | ----+----+-----+ | A | G | 0.46 |
| TSNARE1 | rs10098073 | 8 | 143307411 | 0.5351 | $9.05 \times 10^{-9}$ | ++-++++++++++++ | A | C | 0.93 |
|  | rs4129585 | 8 | 143310840 | 0.5659 | $2.38 \times 10^{-8}$ | ++++++++++++++++ | A | C | 0.99 |

EXAMPLE III

Protein—Protein Interactions (PPI) Show Association of Specific Gene Pathways with Schizophrenia and Bipolar Disorder To test if any gene pathways are enriched in schizophrenia/BP we constructed a PPI network based on the results of the scz/BP GWAS meta-analysis including 13,394 cases and 34,676 controls (as previously described). Gene-level P-values were calculated from the meta-analysis data, 2,998 genes were significant with P-values below 0.05 from the 17,693 genes included in the analysis. The protein-protein interaction (PPI) network was constructed based on indices of protein interactions derived from primary interaction databases including BIND, BioGRID, CORUM, DIP, HPRD, InnateDB, IntAct, MatrixDB, MINT, MPact, MPIDB, MPPI and OPHID as compiled by iRefindex. The network algorithm was retrained using human-human protein interactions supported by at least two publications listed in Pubmed. The largest connected component (LCC, 540 nodes and 768 edges) was used for further analysis. Pathway analysis of the genes in the LCC highlighted several enriched functional pathways in schizophrenia and bipolar disease including the src kinase pathway, circled in Table 5, below.

REFERENCES

1. Glessner J T, Reilly M P, Kim C E, Takahashi N, Albano A, Hou C, et al. Strong synaptic transmission impact by copy number variations in schizophrenia. Proc Natl Acad Sci USA. 2010; 107(23):10584-9. PMCID: 2890845.
2. Genome-wide association study identifies five new schizophrenia loci. Nature genetics. 2011; 43(10):969-76. PMCID: 3303194.
3. Smith J J, Sumiyama K, Amemiya C T. A living fossil in the genome of a living fossil: Harbinger transposons in the coelacanth genome. Mol Biol Evol. 2012; 29(3):985-93. PMCID: 3278475.
4. Cleton A, Rossenu S, Talluri K, Francetic I, Remmerie B, Janssens L, et al. Evaluation of the pharmacokinetics of an extended-release formulation of paliperidone with an immediate-release formulation of risperidone. Annual Meeting of the American Society for Clinical Pharmacology and Therapeutics; Mar. 21-24, 2007; Anaheim, Calif., USA: Clinical Pharmacology and Therapeutics; 2007. p. S62.
5. Kramer M, Simpson G, Maciulis V, Kushner S, Vijapurkar U, Lim P, et al. Paliperidone extended-release tablets for prevention of symptom recurrence in patients with schizophrenia: a randomized, double-blind, placebo-controlled study. J Clin Psychopharmacol. 2007; 27(1):6-14.
6. Tzimos A, Samokhvalov V, Kramer M, Ford L, Gassmann-Mayer C, Lim P, et al. Safety and tolerability

TABLE 5

| Category | Term | RT | Gene Count | % | P-Value | Benajamini |
|---|---|---|---|---|---|---|
| KEGG-Pathway | Proteasome | RT | 13 | 2.4 | 2.1E-6 | 2.5E-4 |
| KEGG-Pathway | Renal cell carcinoma | RT | 15 | 2.7 | 6.9E-6 | 4.1E-4 |
| KEGG-Pathway | MAPK signaling pathway | RT | 32 | 5.8 | 7.4E-6 | 2.9E-4 |
| KEGG-Pathway | Pathways in cancer | RT | 35 | 6.3 | 3.1E-5 | 9.1E-4 |
| KEGG-Pathway | GnRH signaling pathway | RT | 16 | 2.9 | 9.1E-5 | 2.2E-3 |
| KEGG-Pathway | Long-term potentiation | RT | 13 | 2.4 | 1.2E-4 | 2.3E-3 |
| KEGG-Pathway | Ubiquitin mediated proteolysis | RT | 19 | 3.4 | 1.4E-4 | 2.4E-3 |
| KEGG-Pathway | Non-small cell lung cancer | RT | 11 | 2.0 | 2.8E-4 | 4.2E-3 |
| KEGG-Pathway | Progesterone-mediated oocyte maturation | RT | 14 | 2.5 | 3.0E-4 | 4.0E-3 |
| KEGG-Pathway | Neurotrophin signaling pathway | RT | 17 | 3.1 | 4.1E-4 | 4.9E-3 |
| KEGG-Pathway | Regulation of actin cytoskeleton | RT | 24 | 4.3 | 4.1E-4 | 4.5E-3 |
| KEGG-Pathway | Long-term depression | RT | 12 | 2.2 | 5.5E-4 | 5.5E-3 |
| KEGG-Pathway | T cell receptor signaling pathway | RT | 15 | 2.7 | 9.0E-4 | 8.2E-3 |
| KEGG-Pathway | Prostate cancer | RT | 13 | 2.4 | 1.5E-3 | 1.2E-2 |
| KEGG-Pathway | Focal adhesion | RT | 21 | 3.8 | 2.4E-3 | 1.9E-2 |
| KEGG-Pathway | Pancreatic cancer | RT | 11 | 2.0 | 2.9E-3 | 2.1E-2 |
| KEGG-Pathway | Glioma | RT | 10 | 1.8 | 3.8E-3 | 2.6E-2 |
| KEGG-Pathway | ErbB signaling pathway | RT | 12 | 2.2 | 3.8E-3 | 2.5E-2 |
| KEGG-Pathway | TGF-beta signaling pathway | RT | 12 | 2.2 | 3.8E-3 | 2.5E-2 |
| KEGG-Pathway | Fc epsilon RI signaling pathway | RT | 11 | 2.0 | 5.2E-3 | 3.2E-2 | of oral paliperidone extended-release tablets in elderly patients with schizophrenia: a double-blind, placebo-controlled study with six-month open-label extension. Am J Geriatr Psychiatry. 2008; 16(1):31-43.
7. Kane J, Canas F, Kramer M, Ford L, Gassmann-Mayer C, Lim P, et al. Treatment of schizophrenia with paliperidone extended-release tablets: a 6-week placebo-controlled trial. Schizophr Res. 2007; 90(1-3):147-61.
8. Marder S R, Kramer M, Ford L, Eerdekens E, Lim P, Eerdekens M, et al. Efficacy and safety of paliperidone extended-release tablets: results of a 6-week, randomized, placebo-controlled study. Biol Psychiatry. 2007; 62(12):1363-70.
9. Davidson M, Emsley R, Kramer M, Ford L, Pan G, Lim P, et al. Efficacy, safety and early response of paliperidone extended-release tablets (paliperidone ER): results of a 6-week, randomized, placebo-controlled study. Schizophr Res. 2007; 93(1-3):117-30.
10. Meltzer H Y, Bobo W V, Nuamah I F, Lane R, Hough D, Kramer M, et al. Efficacy and tolerability of oral paliperidone extended-release tablets in the treatment of acute schizophrenia: pooled data from three 6-week, placebo-controlled studies. J Clin Psychiatry. 2008; 69(5):817-29.
11. Canuso C M, Dirks B, Carothers J, Kosik-Gonzalez C, Bossie C A, Zhu Y, et al. Randomized, double-blind, placebo-controlled study of paliperidone extended-release and quetiapine in inpatients with recently exacerbated schizophrenia. Am J Psychiatry. 2009; 166(6):691-701.
12. Canuso C M, Lindenmayer J P, Kosik-Gonzalez C, Turkoz I, Carothers J, Bossie C A, et al. A randomized, double-blind, placebo-controlled study of 2 dose ranges of paliperidone extended-release in the treatment of subjects with schizoaffective disorder. J Clin Psychiatry. 2010; 71(5):587-98.
13. Canuso C M, Schooler N, Carothers J, Turkoz I, Kosik-Gonzalez C, Bossie C A, et al. Paliperidone extended-release in schizoaffective disorder: a randomized, controlled study comparing a flexible dose with placebo in patients treated with and without antidepressants and/or mood stabilizers. J Clin Psychopharmacol. 2010; 30(5):487-95.
14. Canuso C M, Turkoz I, Fu D J, Bossie C A. Role of paliperidone extended-release in treatment of schizoaffective disorder. Neuropsychiatr Dis Treat. 2010; 6:667-79.
15. Berwaerts J, Xu H, Nuamah I, Lim P, Hough D. Evaluation of the efficacy and safety of paliperidone extended-release in the treatment of acute mania: a randomized, double-blind, dose-response study. J Affect Disord. 2012; 136(1-2):e51-60.
16. Vieta E, Nuamah I F, Lim P, Yuen E C, Palumbo J M, Hough D W, et al. A randomized, placebo- and active-controlled study of paliperidone extended release for the treatment of acute manic and mixed episodes of bipolar I disorder. Bipolar Disord. 2010; 12(3):230-43.
17. Berwaerts J, Lane R, Nuamah I F, Lim P, Remmerie B, Hough D W. Paliperidone extended-release as adjunctive therapy to lithium or valproate in the treatment of acute mania: a randomized, placebo-controlled study. J Affect Disord. 2011; 129(1-3):252-60.
18. Kramer M, Litman R, Hough D, Lane R, Lim P, Liu Y, et al. Paliperidonepalmitate, a potential long-acting treatment for patients with schizophrenia. Results of a randomized, double-blind, placebo-controlled efficacy and safety study. Int J Neuropsychopharmacol. 2010; 13(5):635-47.
19. Hough D, Gopal S, Vijapurkar U, Lim P, Morozova M, Eerdekens M. Paliperidonepalmitate maintenance treatment in delaying the time-to-relapse in patients with schizophrenia: a randomized, double-blind, placebo-controlled study. Schizophr Res. 2010; 116(2-3):107-17.
20. Kozma C M, Slaton T, Dirani R, Fastenau J, Gopal S, Hough D. Changes in schizophrenia-related hospitalization and ER use among patients receiving paliperidonepalmitate: results from a clinical trial with a 52-week open-label extension (OLE). Curr Med Res Opin. 2011; 27(8):1603-11.
21. Fleischhacker W W, Gopal S, Lane R, Gassmann-Mayer C, Lim P, Hough D, et al. A randomized trial of paliperidonepalmitate and risperidone long-acting injectable in schizophrenia. Int J Neuropsychopharmacol. 1-12.
22. Gopal S, Hough D W, Xu H, Lull J M, Gassmann-Mayer C, Remmerie B M, et al. Efficacy and safety of paliperidonepalmitate in adult patients with acutely symptomatic schizophrenia: a randomized, double-blind, placebo-controlled, dose-response study. Int Clin Psychopharmacol. 2010; 25(5):247-56.
23. Nasrallah H A, Gopal S, Gassmann-Mayer C, Quiroz J A, Lim P, Eerdekens M, et al. A controlled, evidence-based trial of paliperidonepalmitate, a long-acting injectable antipsychotic, in schizophrenia. Neuropsychopharmacology. 2010; 35(10):2072-82.
24. Hough D, Lindenmayer J P, Gopal S, Melkote R, Lim P, Herben V, et al. Safety and tolerability of deltoid and gluteal injections of paliperidonepalmitate in schizophrenia. Prog Neuropsychopharmacol Biol Psychiatry. 2009; 33(6):1022-31.
25. Pandina G J, Lindenmayer J P, Lull J, Lim P, Gopal S, Herben V, et al. A randomized, placebo-controlled study to assess the efficacy and safety of 3 doses of paliperidonepalmitate in adults with acutely exacerbated schizophrenia. J Clin Psychopharmacol. 2010; 30(3):235-44.
26. Bossie C A, Sliwa J K, Ma Y W, Fu D J, Alphs L. Onset of efficacy and tolerability following the initiation dosing of long-acting paliperidonepalmitate: post-hoc analyses of a randomized, double-blind clinical trial. BMC Psychiatry. 2011; 11:79.
27. Simpson G M, Mahmoud R A, Lasser R A, Kujawa M, Bossie C A, Turkoz I, et al. A 1-year double-blind study of 2 doses of long-acting risperidone in stable patients with schizophrenia or schizoaffective disorder. J Clin Psychiatry. 2006; 67(8):1194-203.
28. Gharabawi G M, Greenspan A, Rupnow M F, Kosik-Gonzalez C, Bossie C A, Zhu Y, et al. Reduction in psychotic symptoms as a predictor of patient satisfaction with antipsychotic medication in schizophrenia: data from a randomized double-blind trial. BMC Psychiatry. 2006; 6:45.
29. Haas M, Delbello M P, Pandina G, Kushner S, Van Hove I, Augustyns I, et al. Risperidone for the treatment of acute mania in children and adolescents with bipolar disorder: a randomized, double-blind, placebo-controlled study. Bipolar Disord. 2009; 11(7):687-700.
30. Turner M, Eerdekens E, Jacko M, Eerdekens M. Long-acting injectable risperidone: safety and efficacy in stable patients switched from conventional depot antipsychotics. Int Clin Psychopharmacol. 2004; 19(4):241-9.
31. Smulevich A B, Khanna S, Eerdekens M, Karcher K, Kramer M, Grossman F. Acute and continuation risperidonemonotherapy in bipolar mania: a 3-week placebo-controlled trial followed by a 9-week double-blind trial of risperidone and haloperidol. Eur Neuropsychopharmacol. 2005; 15(1):75-84.

32. Hirschfeld R M, Keck P E, Jr., Kramer M, Karcher K, Canuso C, Eerdekens M, et al. Rapid antimanic effect of risperidonemonotherapy: a 3-week multicenter, double-blind, placebo-controlled trial. Am J Psychiatry. 2004; 161(6):1057-65.

33. Lindenmayer J P, Eerdekens E, Berry S A, Eerdekens M. Safety and efficacy of long-acting risperidone in schizophrenia: a 12-week, multicenter, open-label study in stable patients switched from typical and atypical oral antipsychotics. J Clin Psychiatry. 2004; 65(8):1084-9.

EXAMPLE IV

Common and Rare Genetic Risk Factors for Schizophrenia

As described in the previous examples, schizophrenia is a psychiatric brain disorder with profound genetic heterogeneity. Genetic risk factors of schizophrenia range in frequency from common to rare, including common single nucleotide polymorphisms (SNPs), recurrent rare copy number variants (CNVs) and de novo mutations (DNMs) [1-16]. Current genome-wide association studies (GWAS) in schizophrenia have reported 108 genome-wide significant loci, each of small effect size [16]. It has also been reported that at least a quarter of the genetic contribution to schizophrenia risk can be explained by common SNPs [1, 16, 17]. On the other hand, multiple case-control studies have identified rare CNVs of strong effect to the risk of schizophrenia [4-6, 8-10, 13, 15, 18, 19]. In addition, recent sequencing studies have shed new light on the genetic basis of schizophrenia that DNMs play a prominent part in the sporadic form of schizophrenia [11, 14, 20, 21].

In these studies, multiple pieces of evidence show that genetic susceptibility of schizophrenia displays disruption across a group of functionally related genes implying complex genetic network underlying schizophrenia [10, 11, 20]. To explore the network structure of schizophrenia, many network-based approaches have been applied to different types of genetic variations [22-26]. Among the different types of gene networks, protein-protein interaction (PPI) networks as described above in Example III have been shown to be a powerful tool for identifying disease-associated modules and pathways, and reveal the biological significance of diverse genetic variations [22, 27-33]. For example, instead of pursuing genome-wide significance, two GWA studies have successfully identified disease-associated gene modules, which are comprised of many closely interacting genes showing nominal significance, by integrating PPI networks analysis into GWAS [31,32]. However, it is still a challenge to conduct a comprehensive PPI network analysis, in particular by incorporating different types of genetic factors from different tissue types.

In the present example, we established a network-based approach to investigate the gene modules and pathways underlying schizophrenia, and to explore the inherent associations among multiple genetic risk factors. Our analysis uncovered significantly enriched association signals in pathways relevant to synaptic plasticity, neural development and signaling transduction such as long-term potentiation, neurotrophin signaling pathway, ERBB signaling pathway and MAPK signaling pathway, suggesting those play contributory roles in the pathophysiology of schizophrenia. We also demonstrated that genes targeted by common SNPs are more likely to interact with genes carrying DNMs. Finally, we identified a group of interacting genes showing a significant combined effect to the genetic susceptibility of schizophrenia.

The following materials and methods are provided to facilitate the practice of Example IV.

GWAS Data Sets

Gene-level P values were calculated based on SNP P values from the largest GWAS conducted by Schizophrenia Psychiatric Genome-Wide Association Study Consortium (PGC), which recruited 36,989 cases and 113,075 controls (PGC phase 2, abbreviated as PGG2)[16]. The association results were downloaded from the website of PGC (http://www.med.unc.edu/pgc/downloads). As a control, we used the GWAS data of Crohn's disease (CD) from the International IBD Genetics Consortium (http://www.ibdgenetics.org) including a total of 3,685 cases and 5,968 controls[34].

Gene-Level Associations

Gene-level associations were calculated by VEGAS [35]. VEGAS performs Monte-Carlo simulations from the multivariate normal distribution based on the LD pattern from reference populations and assigns an estimated P value to each gene. SNPs located within 50 kb upstream and 50 kb down stream of gene boundaries are used in the analysis in order to capture regulatory regions and SNPs in LD. Previous studies suggested P value <0.05 as the threshold of gene-level significance [32,35]. However, since the number of genome-wide significant loci from the PGG2 study are much more than from the previous studies as a result of study size differences, the gene-level significance at both P value <0.01 (2501 significant genes) and P value <0.05 (4698 significant genes) was evaluated in this study. Genes located in the MHC region (25-34 mb on chr6) were excluded in the analysis.

Rare Genetic Variations Curation

In this study, we used the sequencing results from previous studies [11, 14, 20] and annotated the variants by wANNOVAR (http://wannovar.usc.edu) [36]. We used SIFT and Polyphen2 (HDIV) scores compiled by dbNSFP2 database as well as the AVSIFT score based on annotations at http://sift.bii.a-star.edu.sg to assess whether the missense variants are benign or damaging. For the CNVs, we collected the genes disrupted by CNVs reported in large case-control studies of schizophrenia.

Network Analysis

Figure 15A:
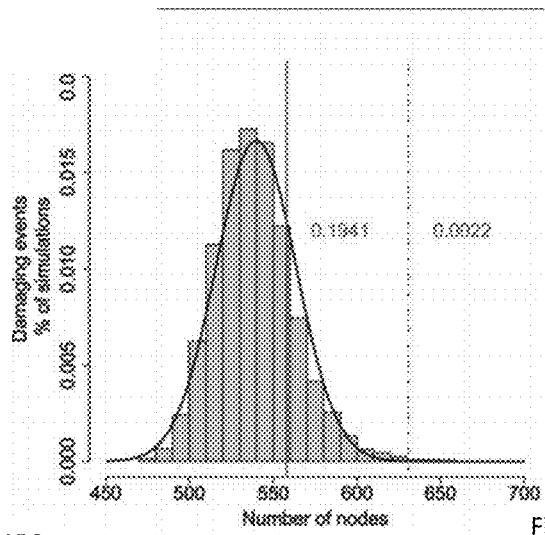
FIGS. 15A-15E FIG. 15A: Connectedness of the LCC based on gene-level significant genes (Pgene<0.01) from PGC2 study and genes harboring DNMs. Original size of LCC based on gene-wise significant genes constituting 402 nodes and 620 edges. 635 genes harboring DNMs are added to generate the new LCC. The background distribution is generated by 10,000 LCCs based on adding 635 random selected genes. P values are estimated by the proportion of LCCs from random networks with more nodes or edges than the real network. As a control, we use the LCC generated by adding top 635 gene-level significant genes from Crohn's disease as control. Dash lined enotes the size of LCC generated by adding DNMs. Solid line denotes the size of LCC generated by adding CD top genes. Adding DNMs significantly increased the size of LCCs (DNMs: Pnode=0.0022, Pedge=0.0032; CD: Pnode=0.1941, Pedge=0.0678), while adding top CD genes did not. For comparison, we also added the synonymous and non-frameshift substitutions to generate the new LCC. The size of new LCC is not significantly larger than random simulations (Benign substitutions: Pnode=0.698, Pedge=0.0571; CD: Pnode=0.1922, Pedge=0.1900).
Figure 15B:
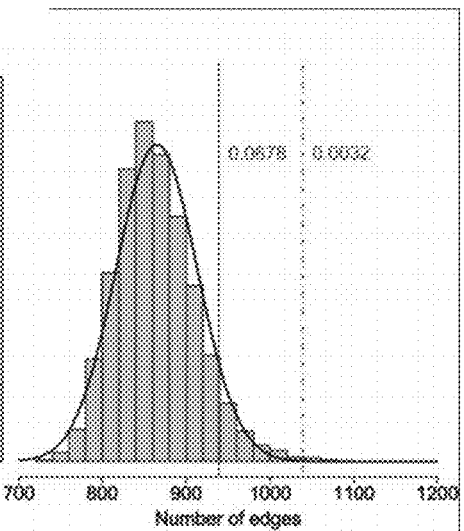
Figure 15C:
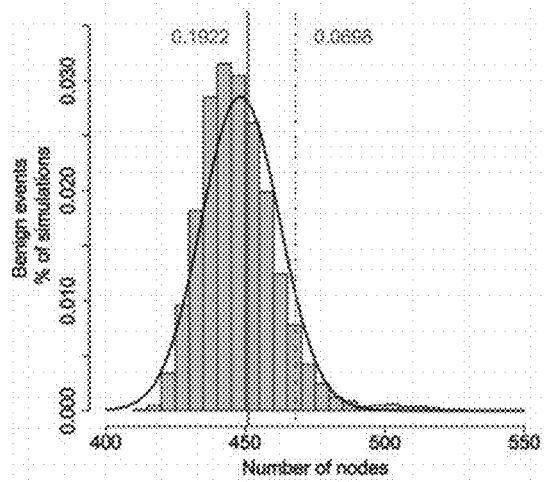
Figure 15D:
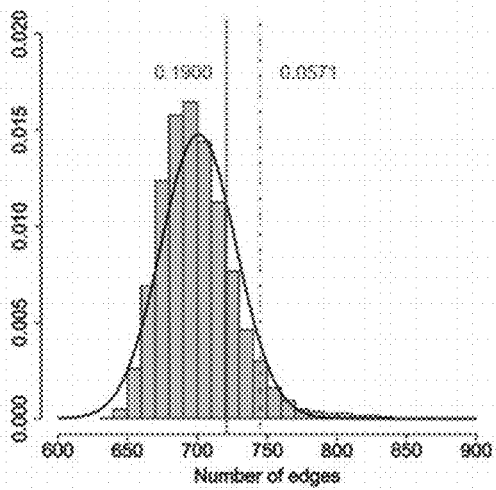
Figure 15E:
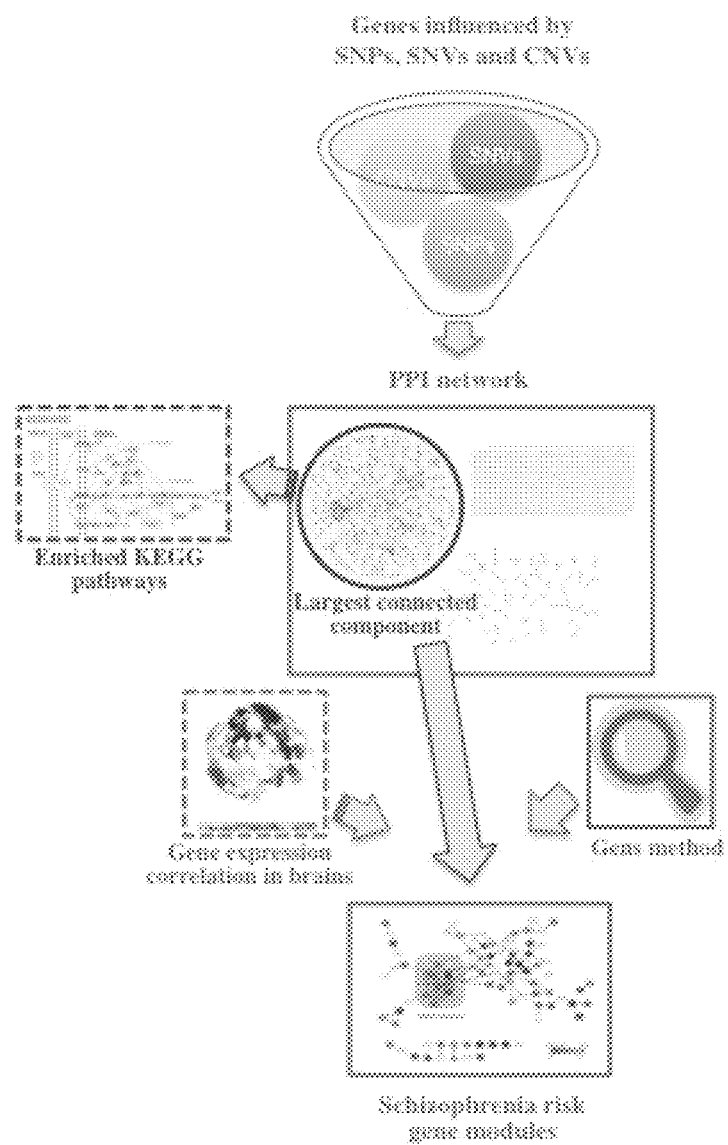
Figure 16A:
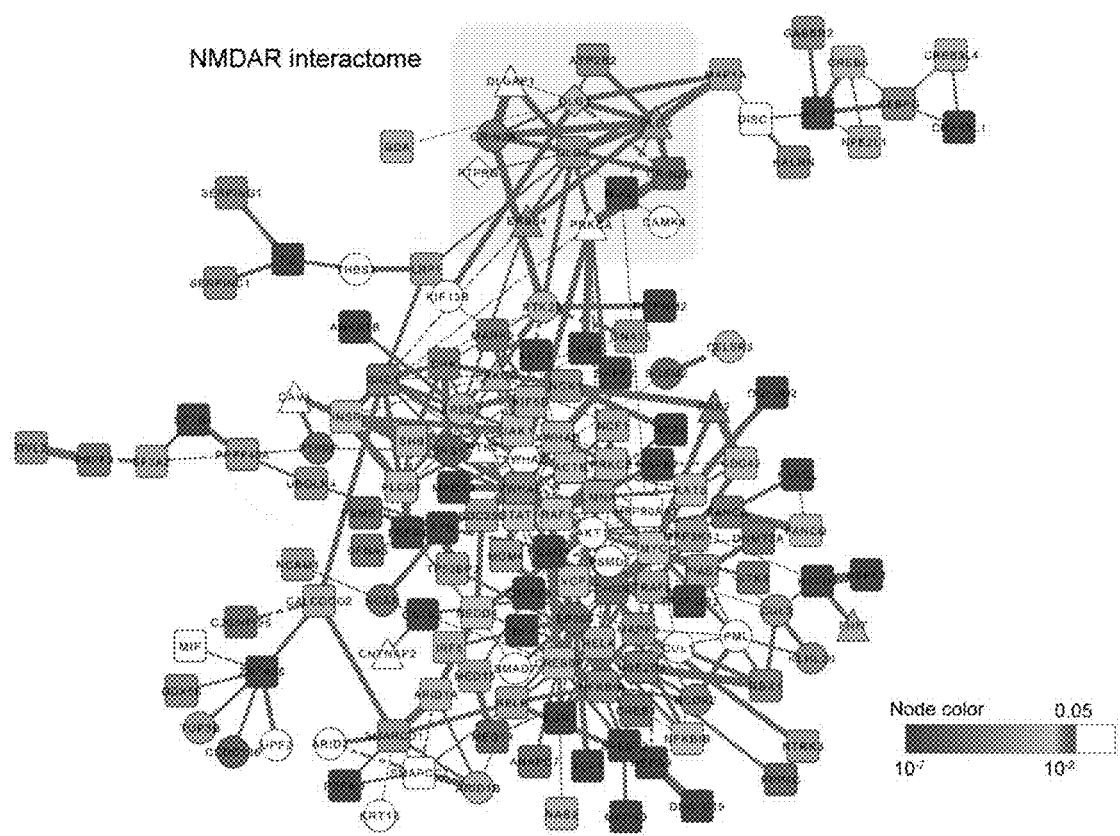
FIGS. 16A-16G.
Figure 16B:
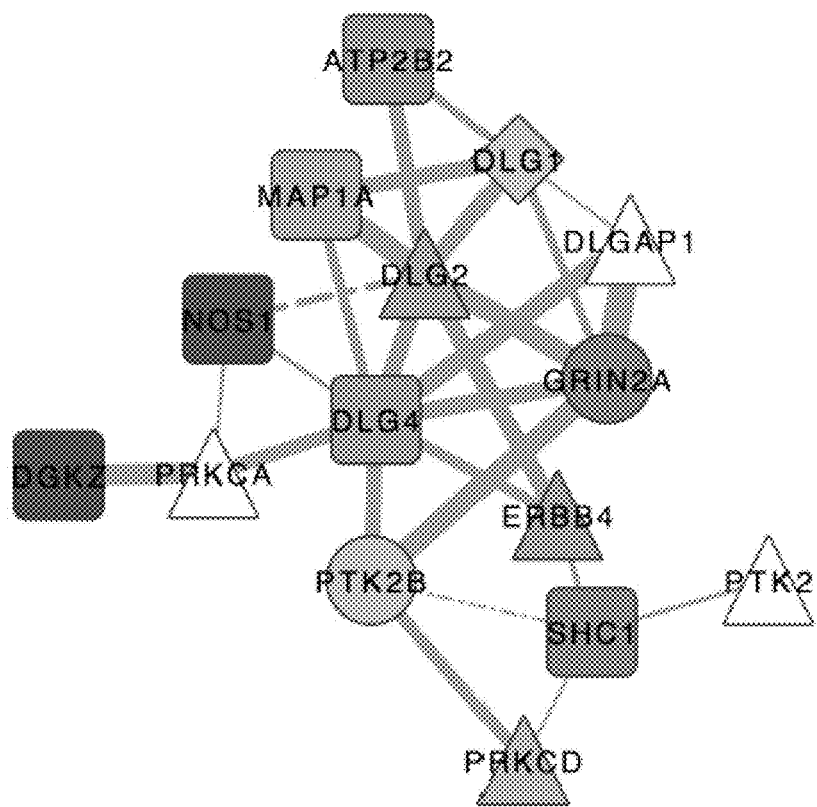
Figure 16C:
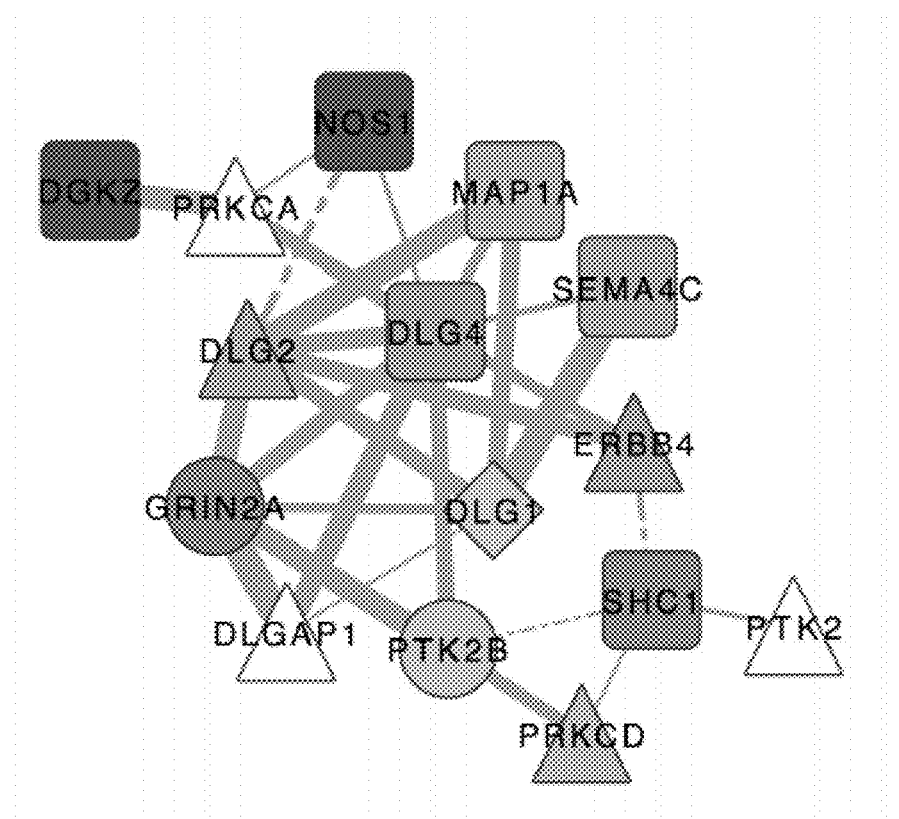
Figure 16D:
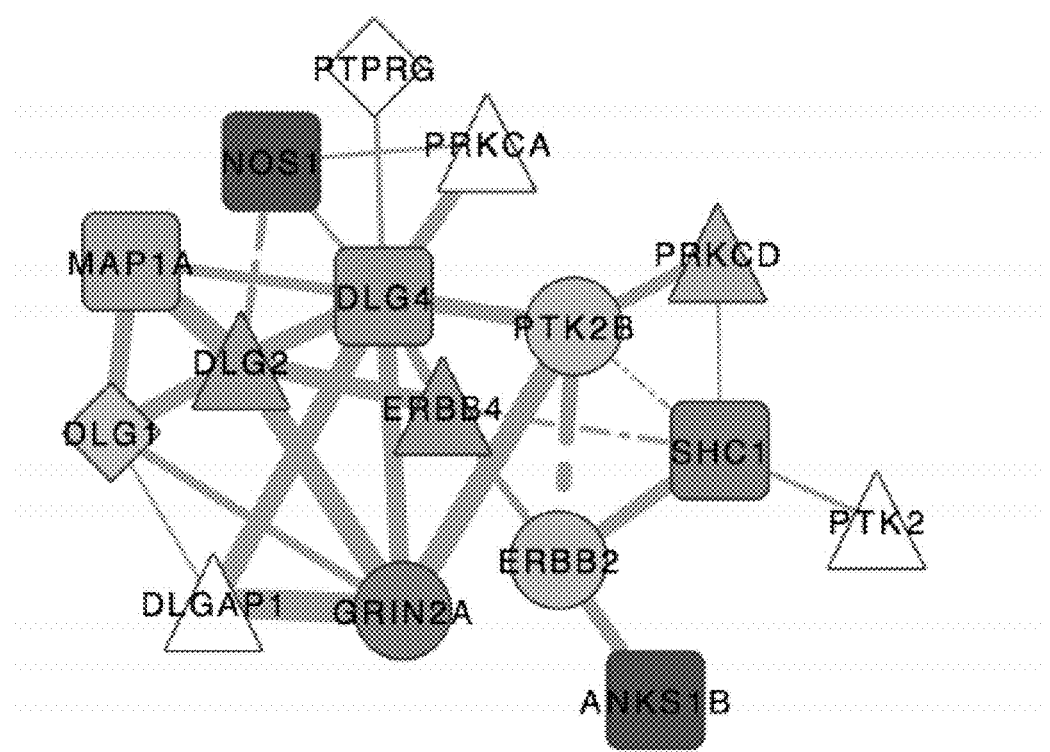
Figure 16E:
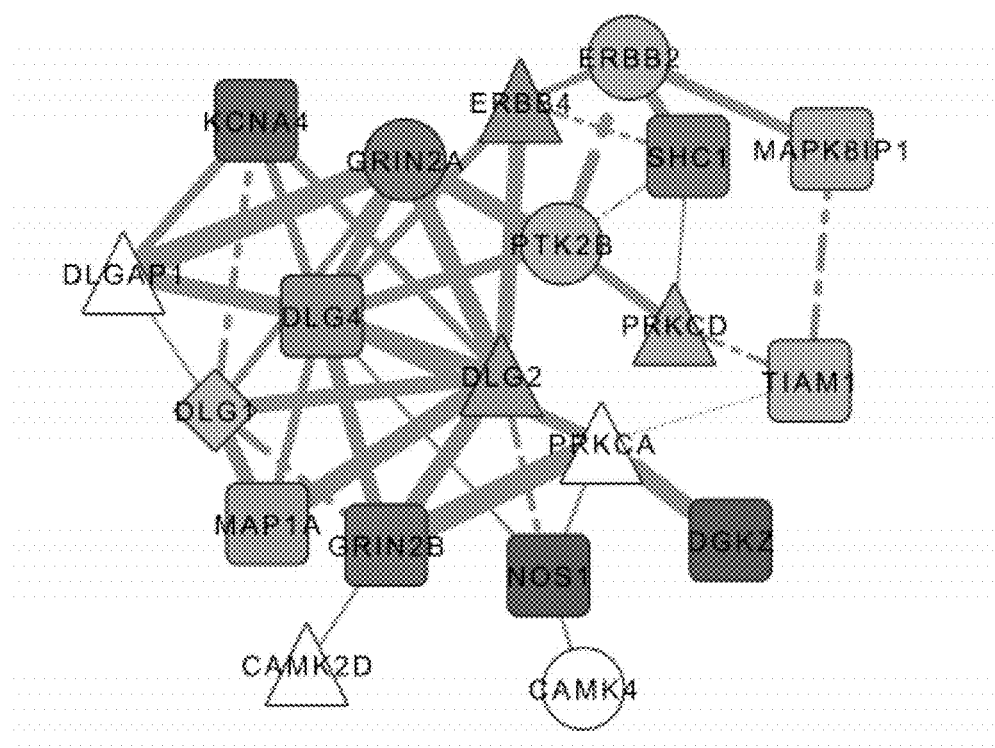
Figure 16F:
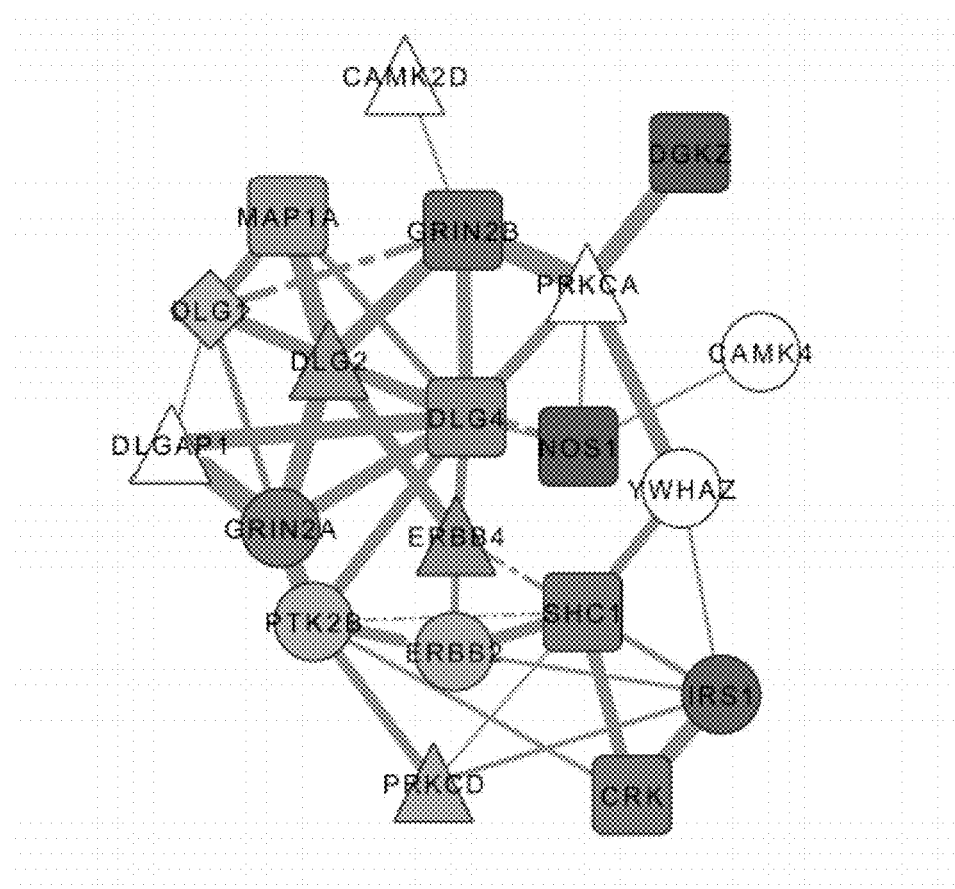
Figure 16G:
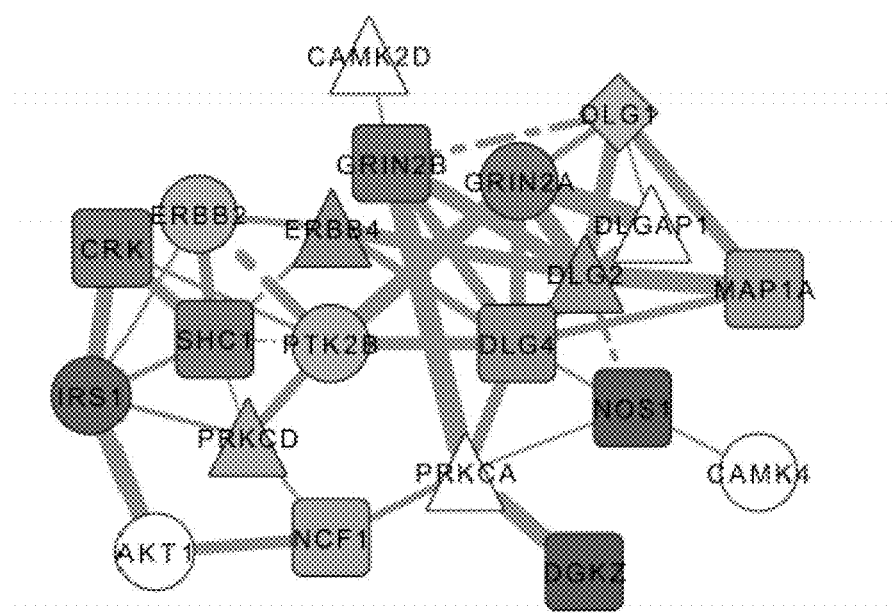
Figure 17A:
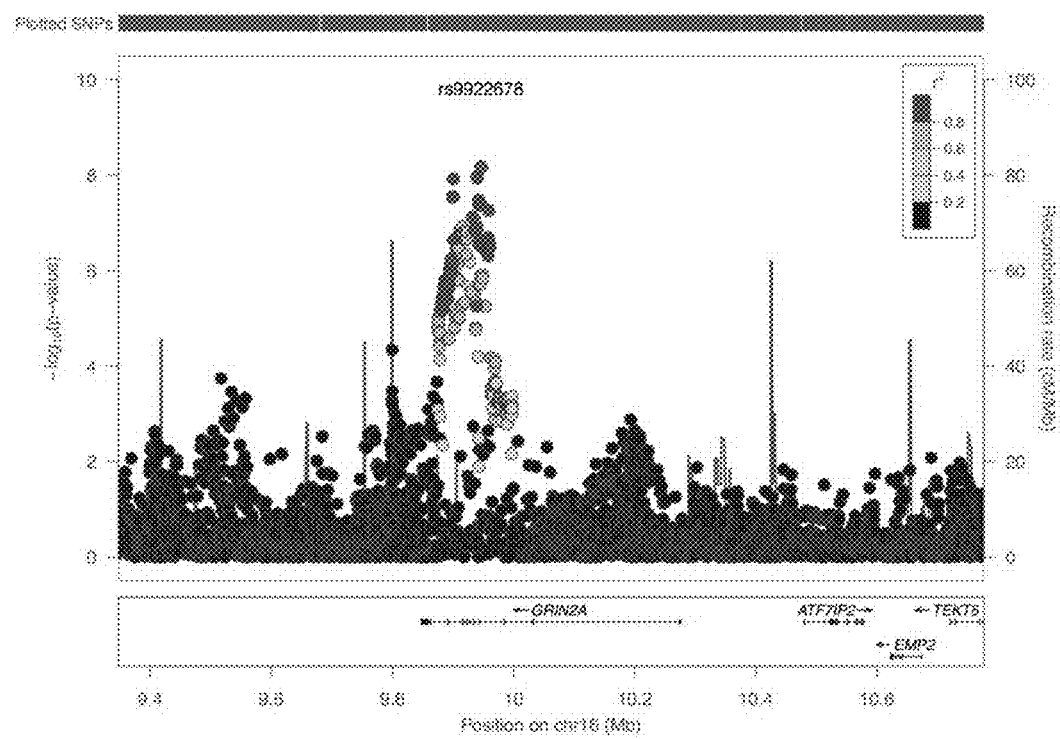
FIGS. 17A-17BB. Regional plot of the gene loci identified from the PPI network, which show strong associations with schizophrenia risk. Plotted are the significance of association (−10-transformed P values) and the recombination rate. SNPs are colored to reflect pairwise LD (r2) with the most significantly associated genotyped SNP. The most significant genotyped SNPs are marked in purple.
Figure 17B:
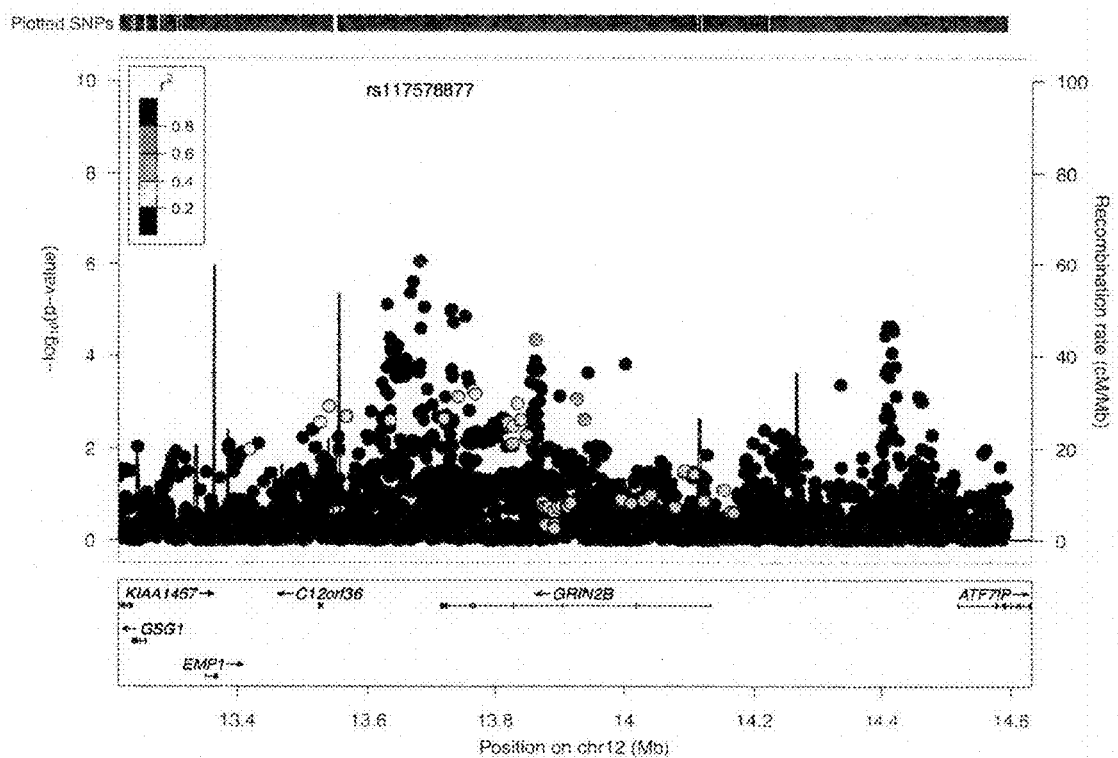
Figure 17C:
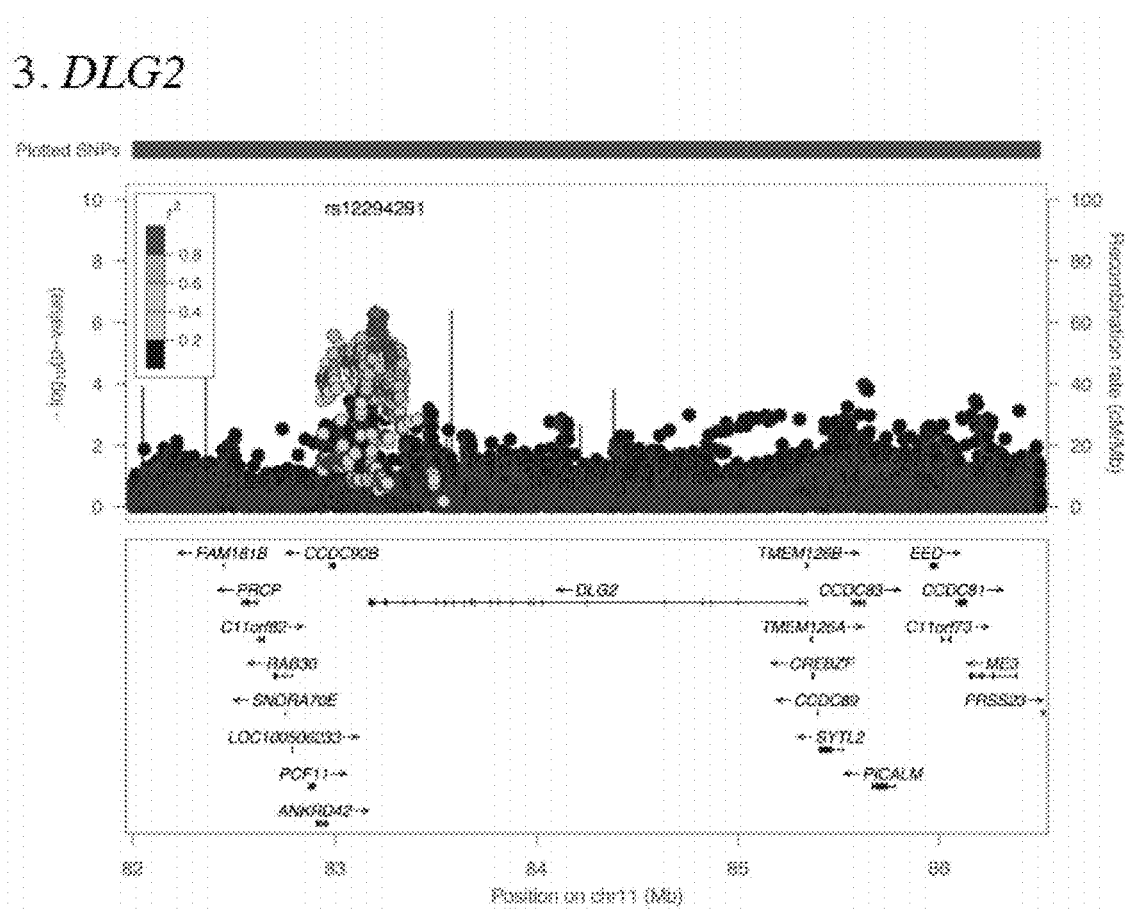
FIG. 17C. DLG2.
Figure 17D:
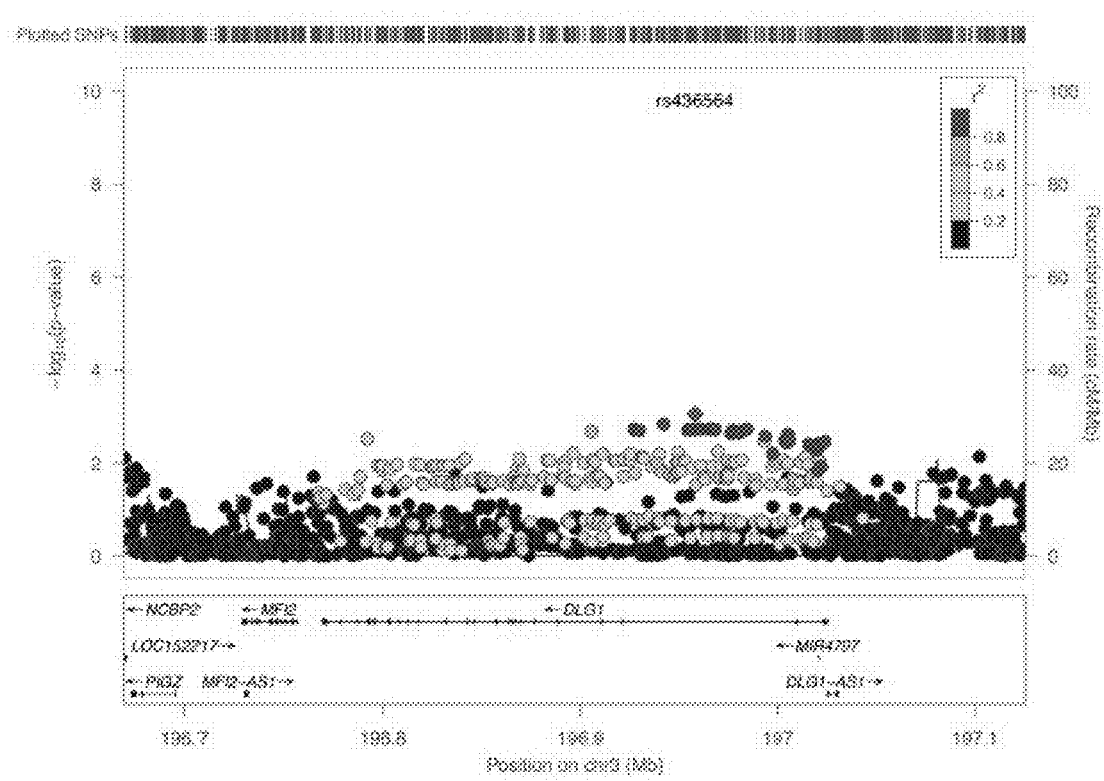
FIG. 17D. DLG1.
Figure 17E:
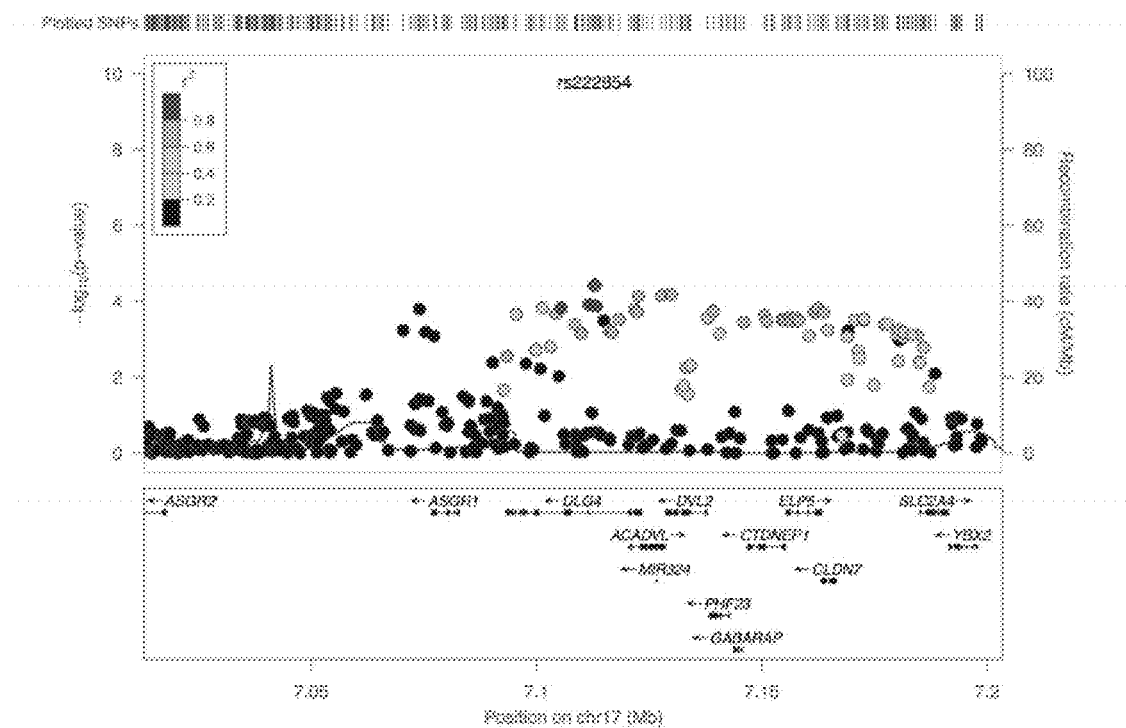
FIG. 17E. DLG4.
Figure 17F:
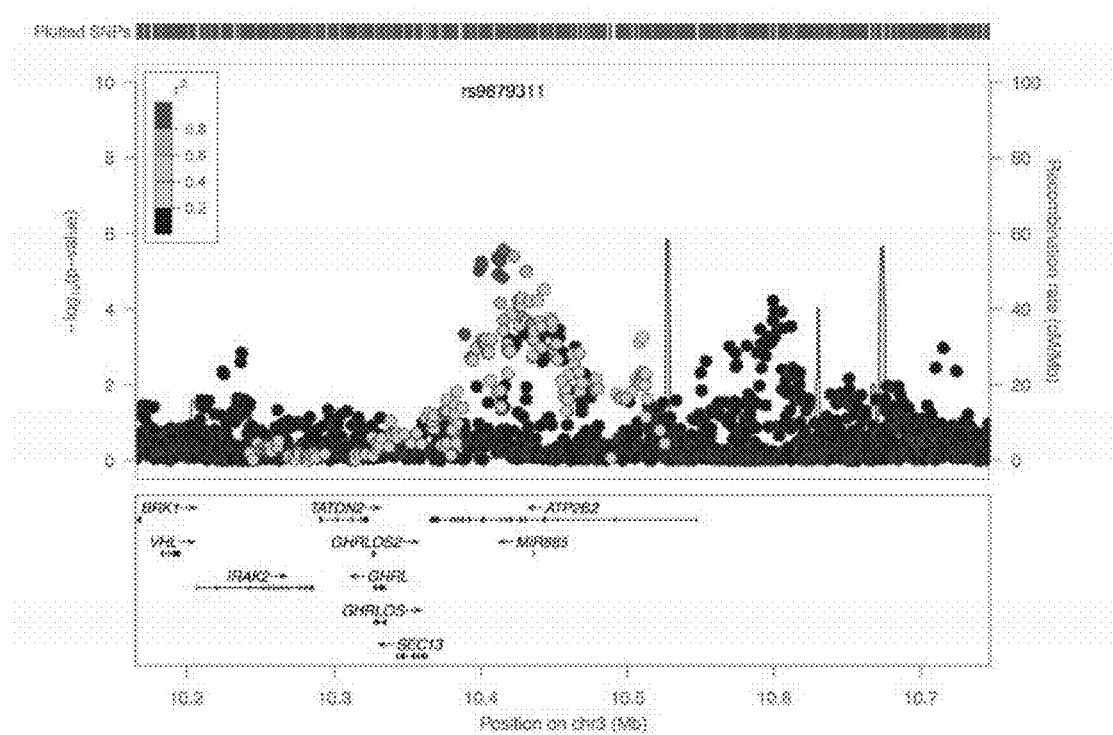
FIG. 17F. ATP2B2.
Figure 17G:
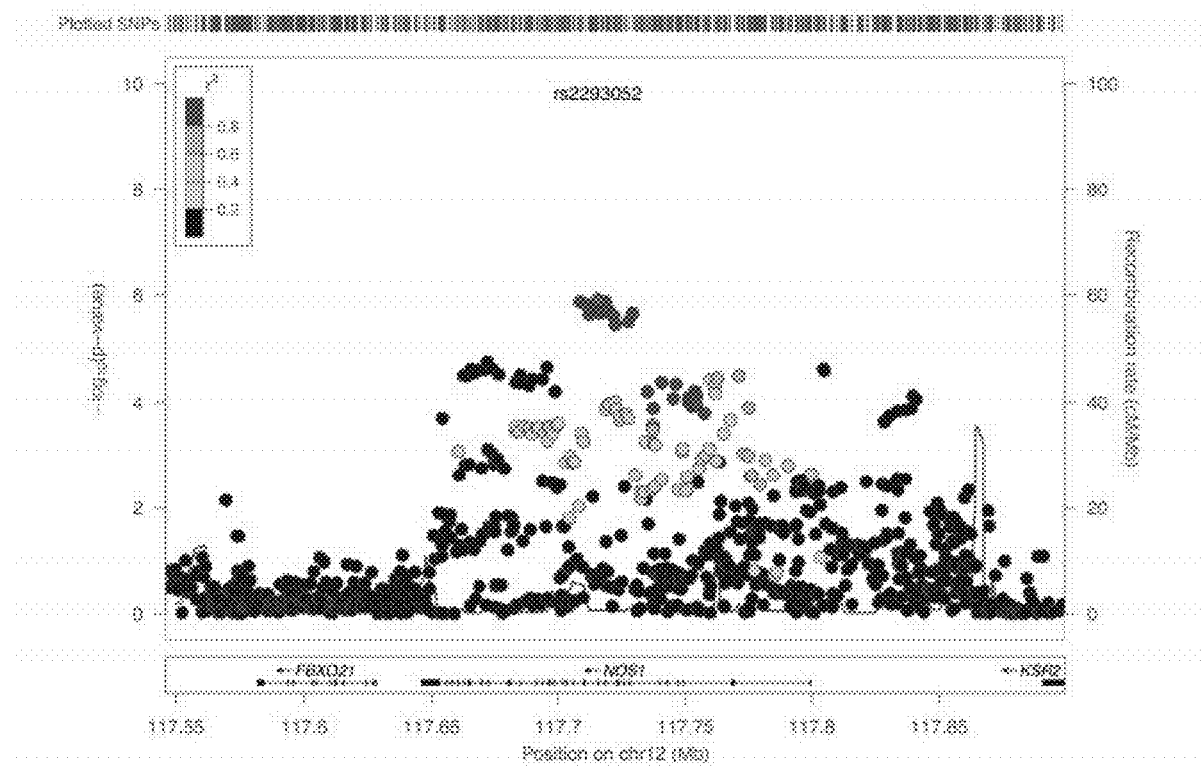
FIG. 17G. NOS1.
Figure 17H:
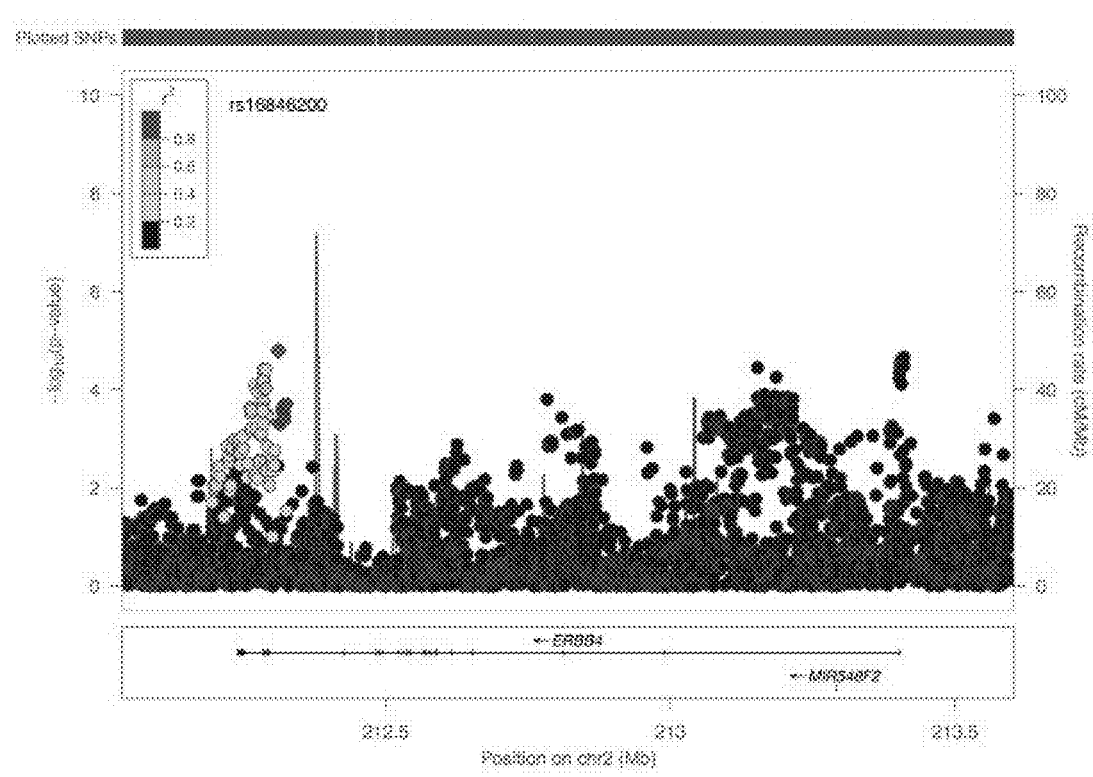
FIG. 17H. ERBB4.
Figure 17I:
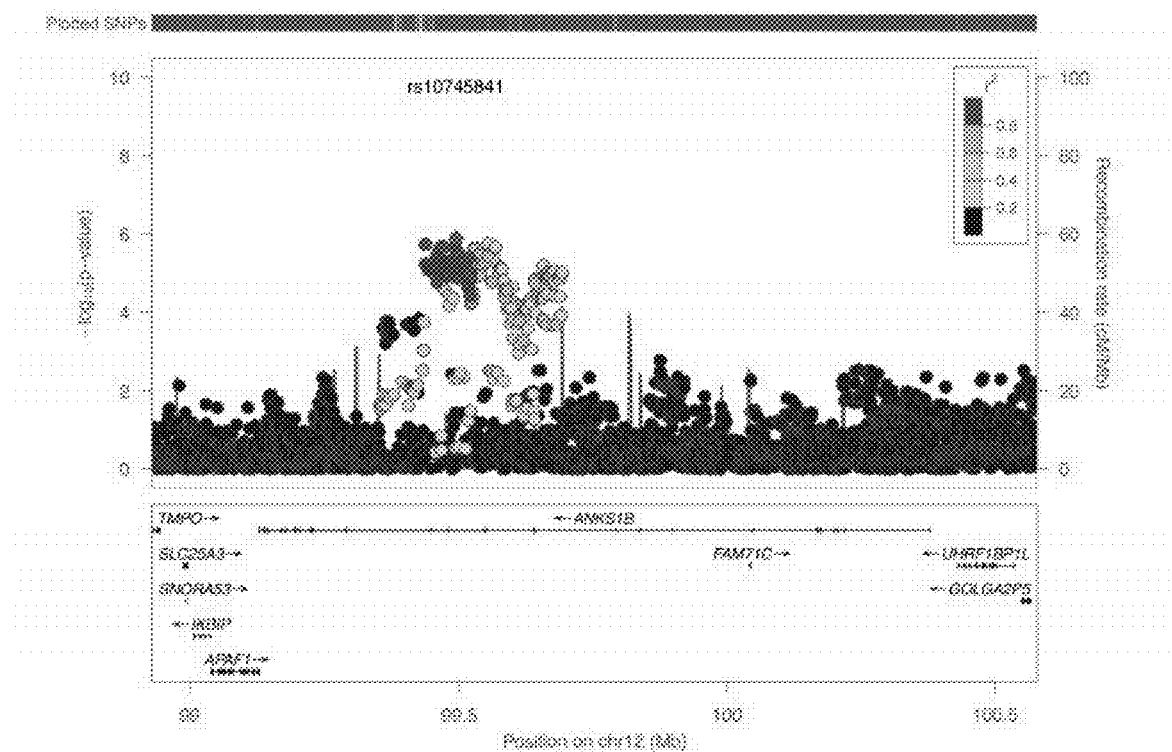
FIG. 17I. ANSK1B.
Figure 17J:
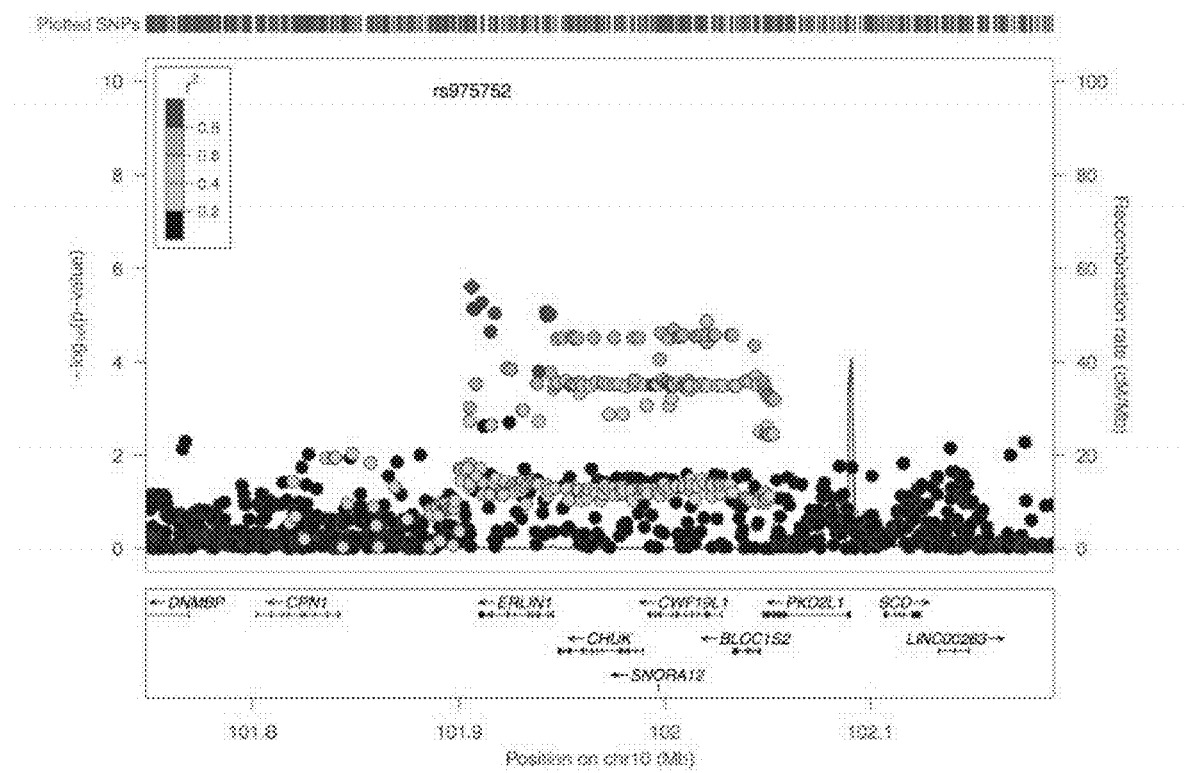
FIG. 17J. CHUK.
Figure 17K:
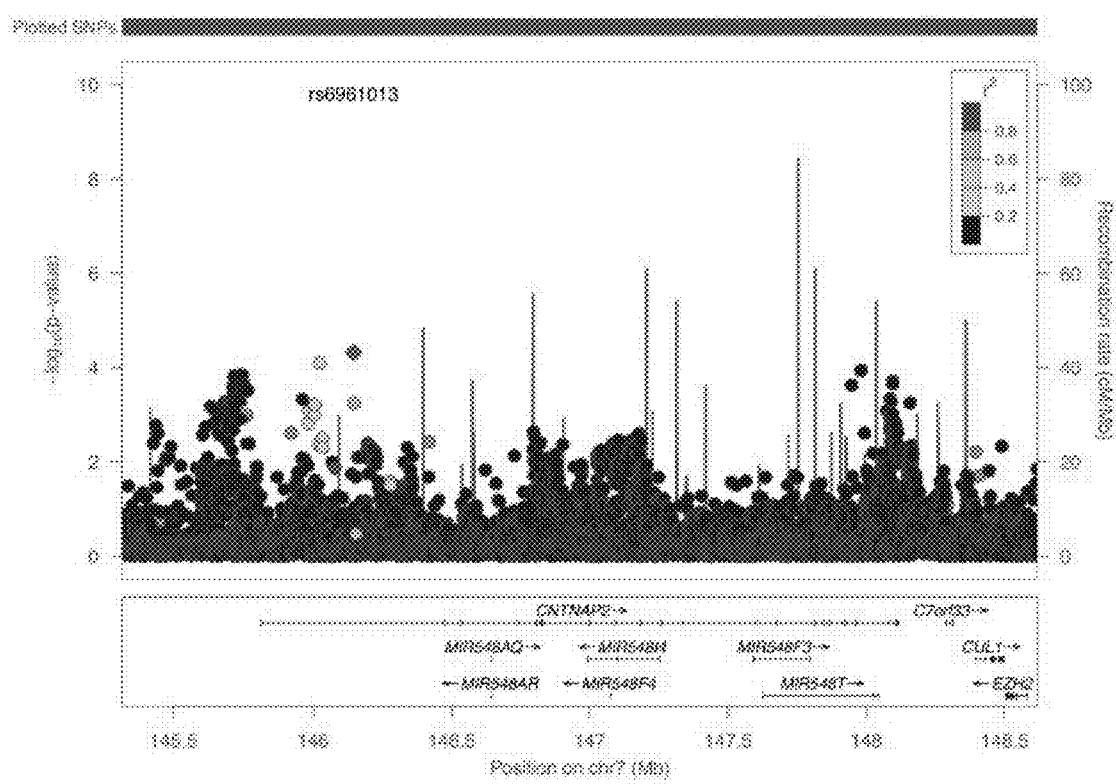
FIG. 17K. CNTN2.
Figure 17L:
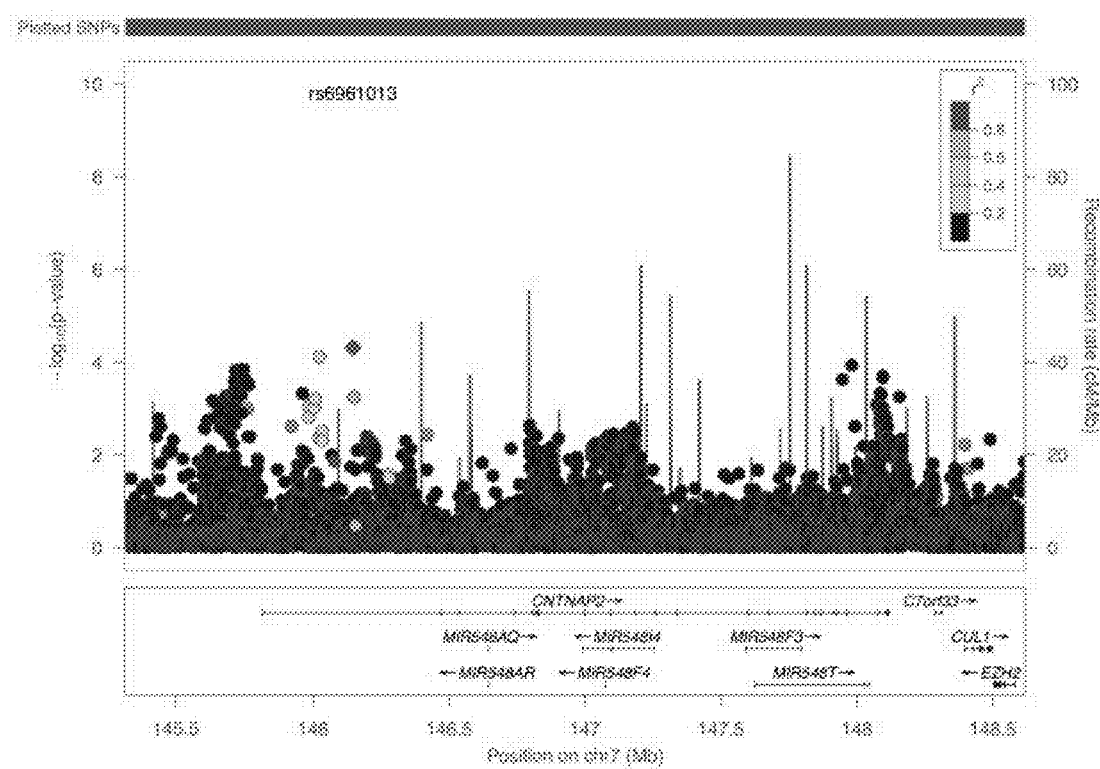
FIG. 17L. CNTNAP2.
Figure 17M:
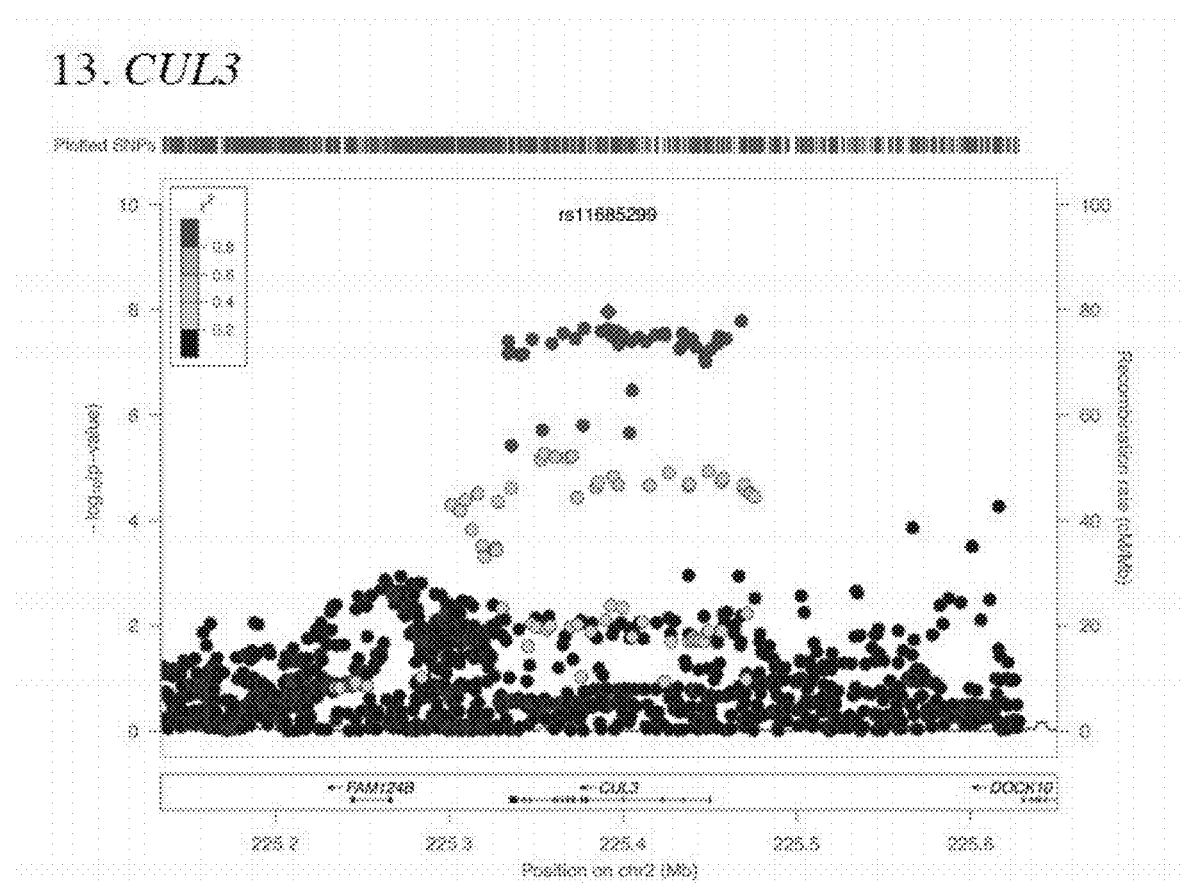
FIG. 17M. CUL3.
Figure 17N:
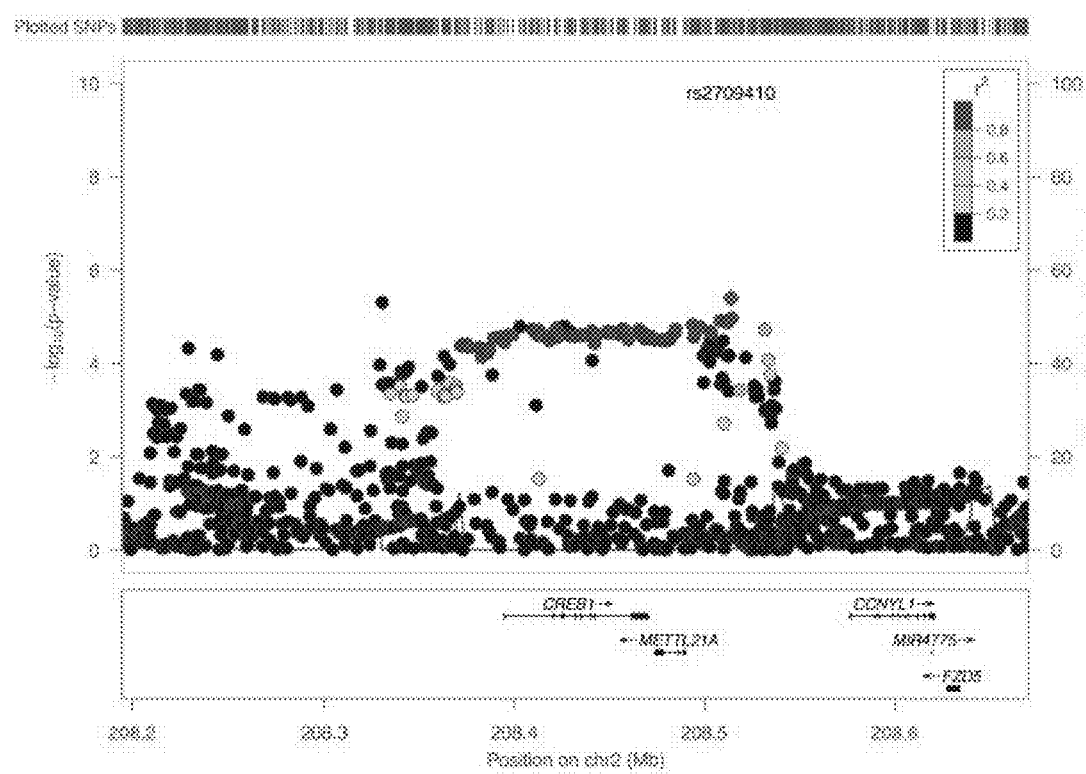
FIG. 17N. CREB1.
Figure 17O:
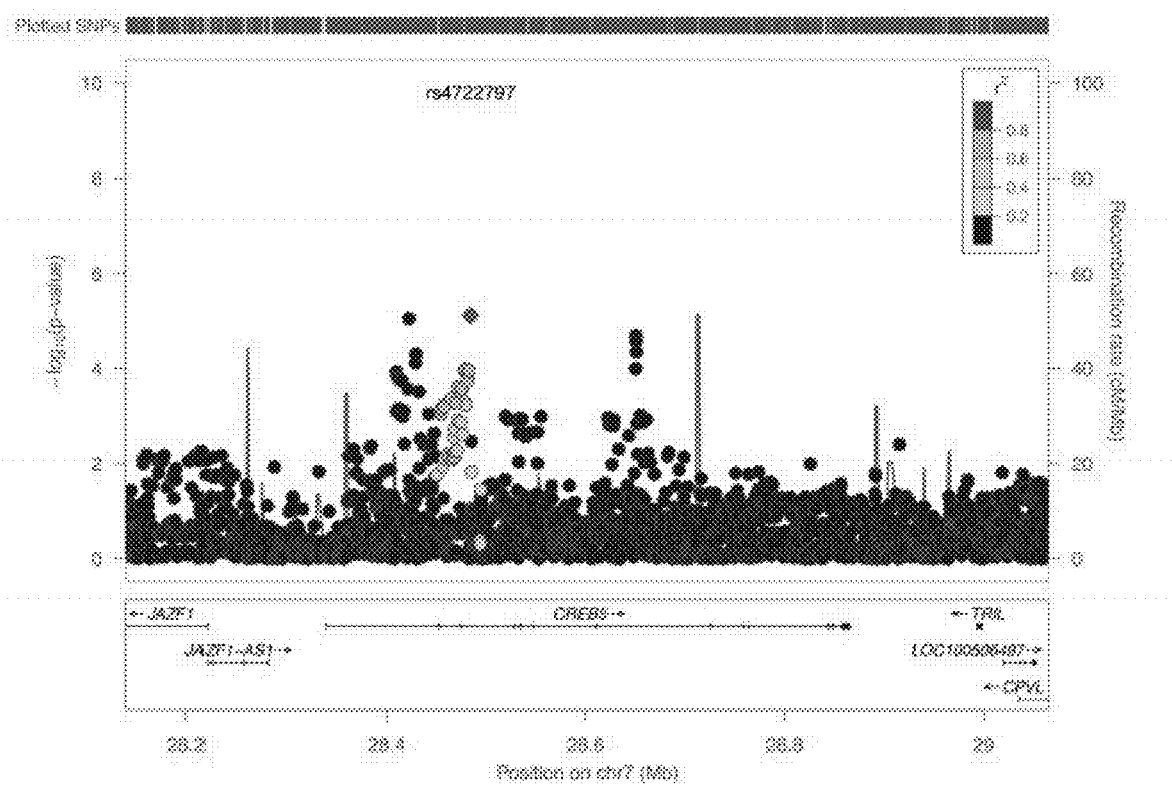
FIG. 17O. CREB5.
Figure 17P:
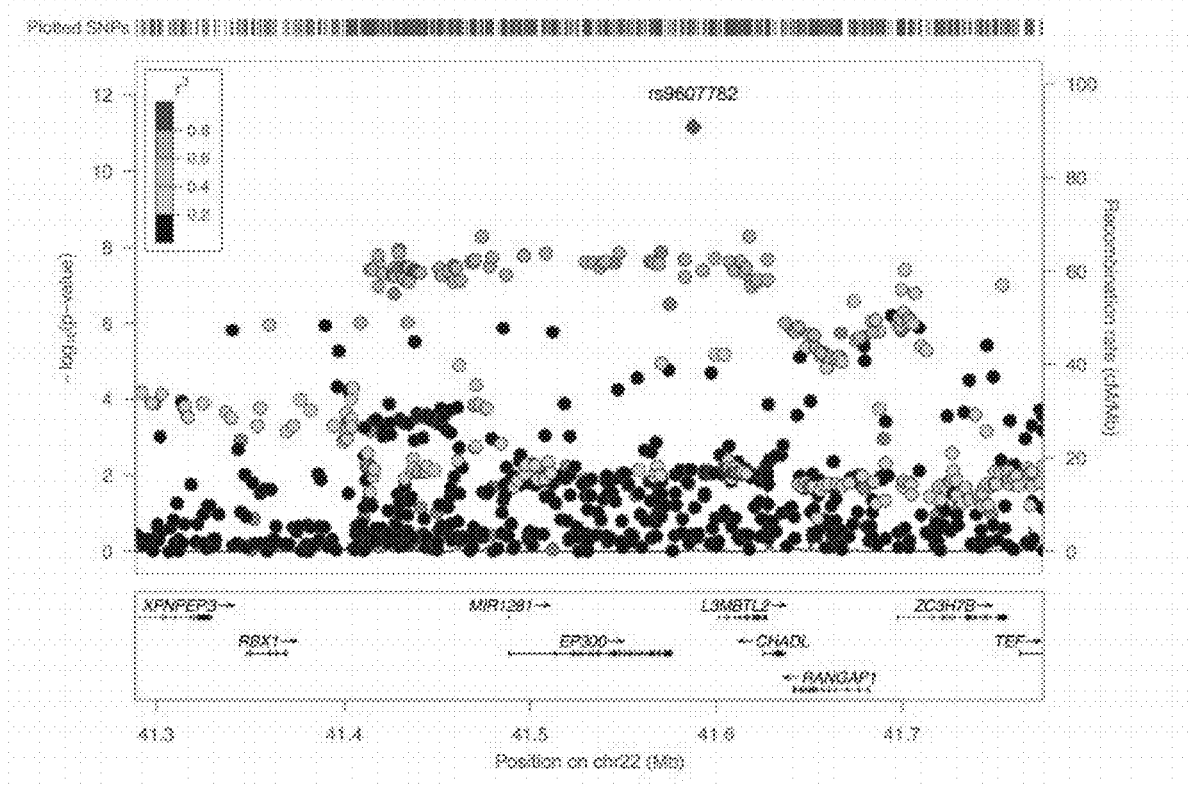
FIG. 17P. EP300.
Figure 17Q:
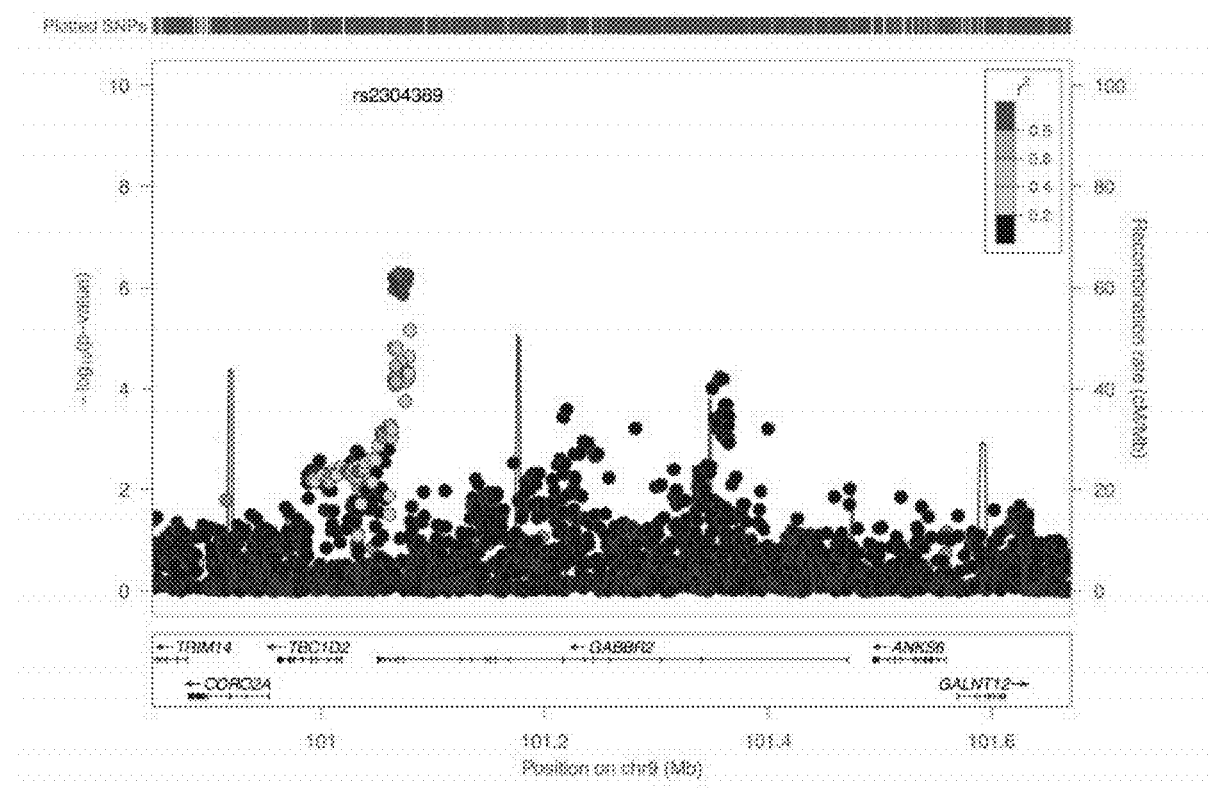
FIG. 17Q. GABBR2.
Figure 17R:
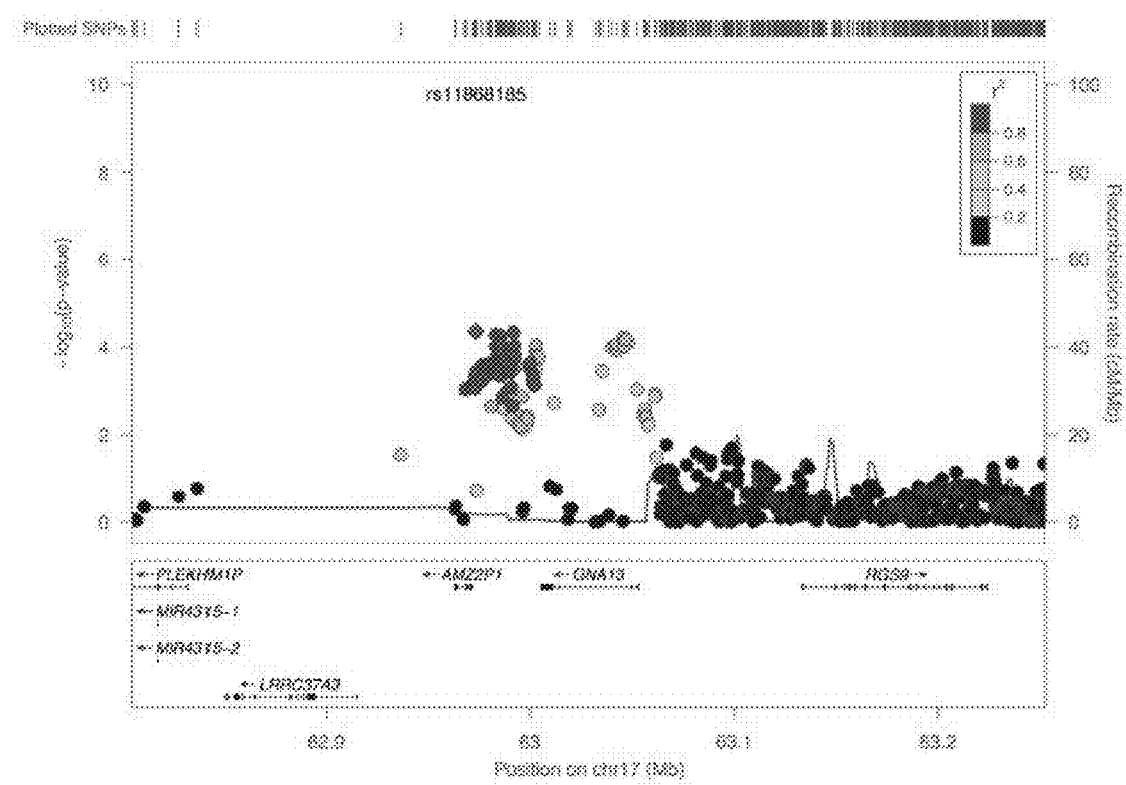
FIG. 17R. GNA13.
Figure 17S:
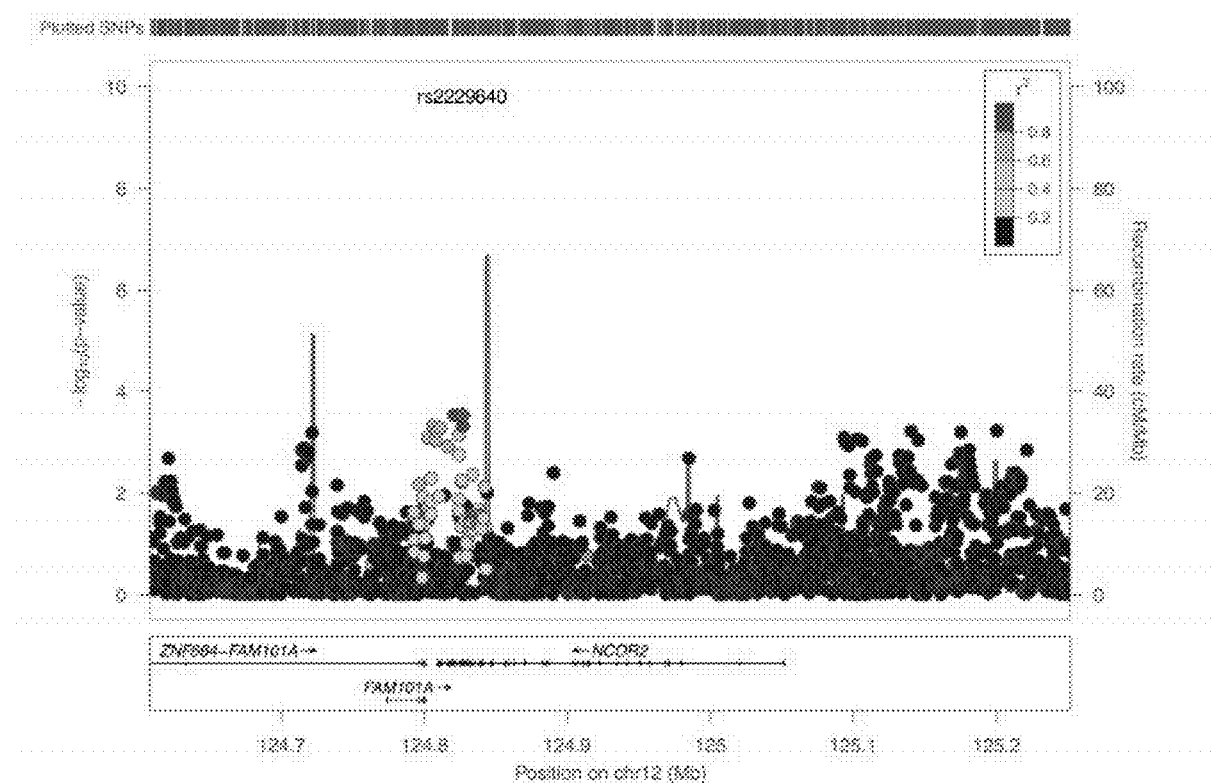
FIG. 17S. NCOR2.
Figure 17T:
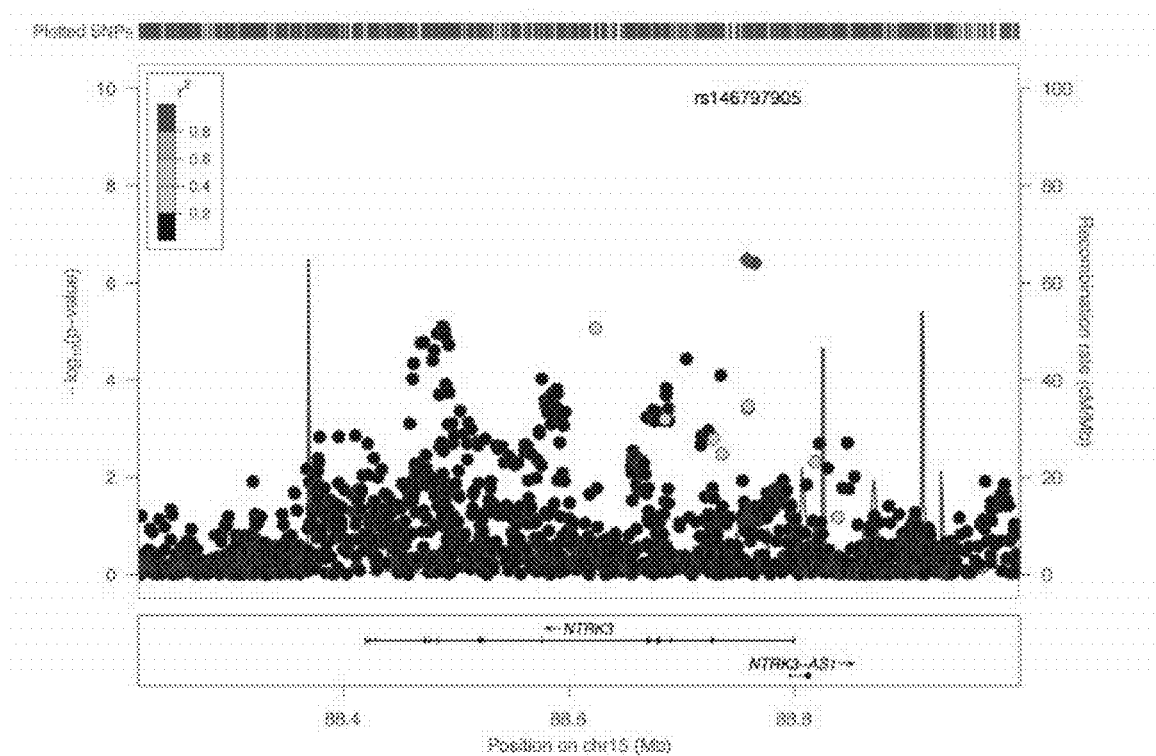
FIG. 17T. NTRK3.
Figure 17U:
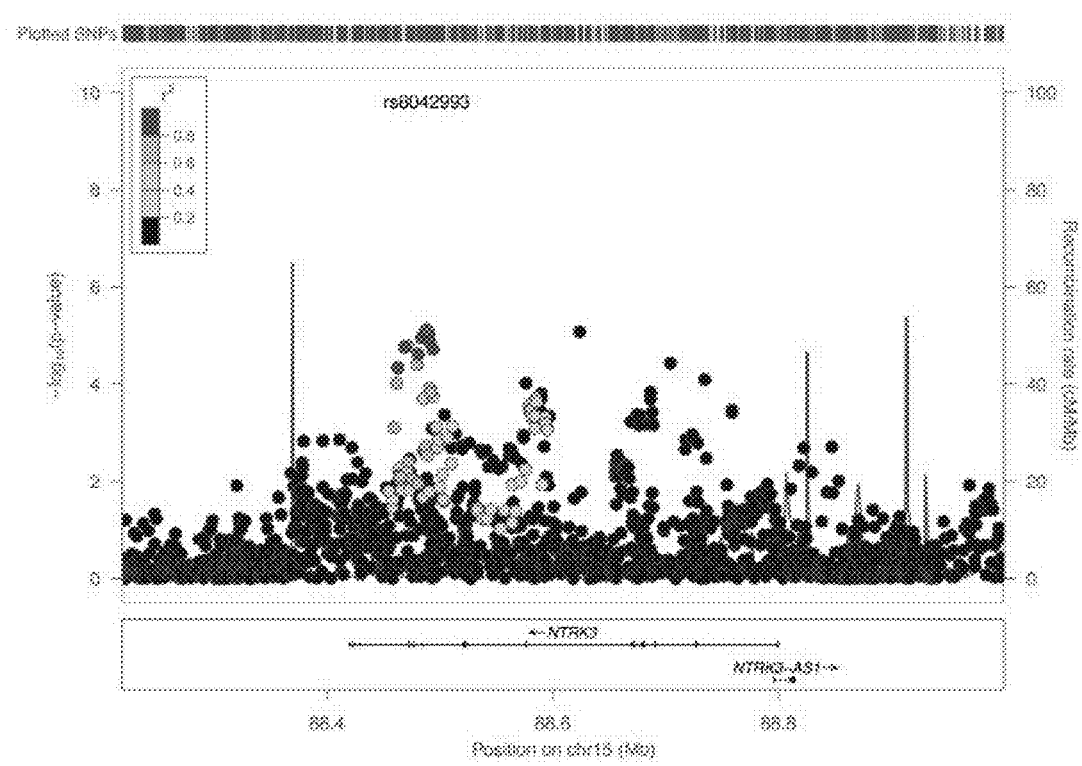
FIG. 17U. NTKR3 (remove 146797905)
Figure 17V:
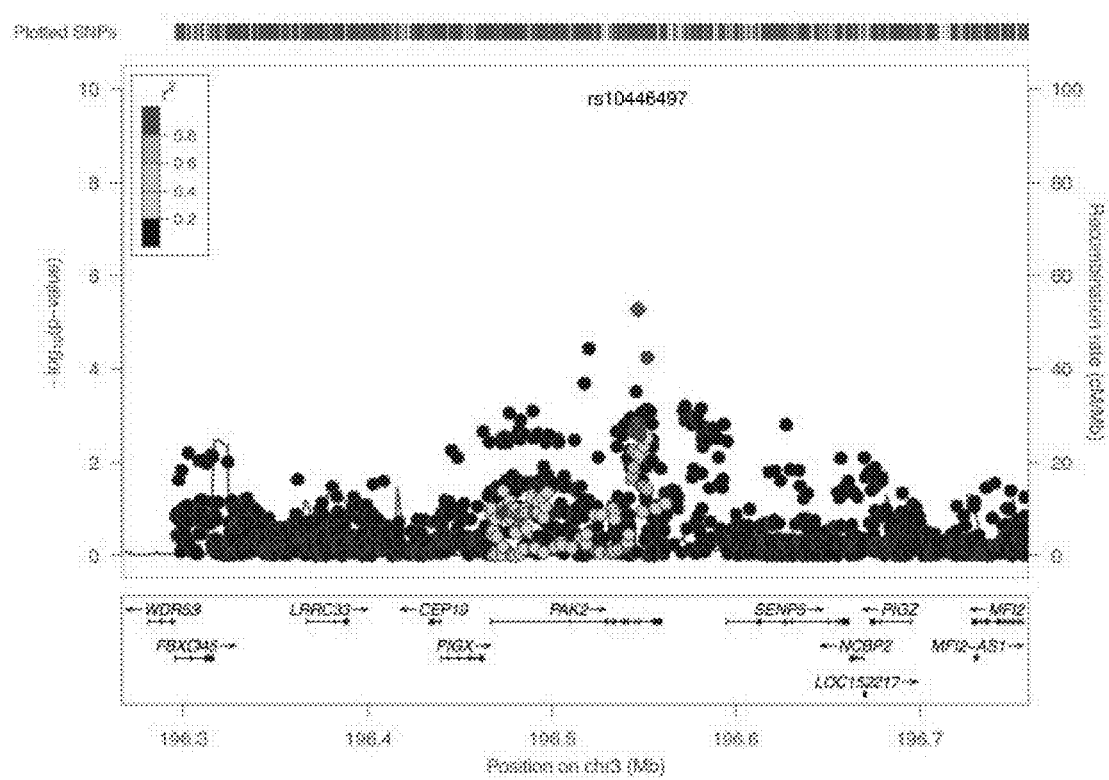
FIG. 17V. PAK2.
Figure 17W:
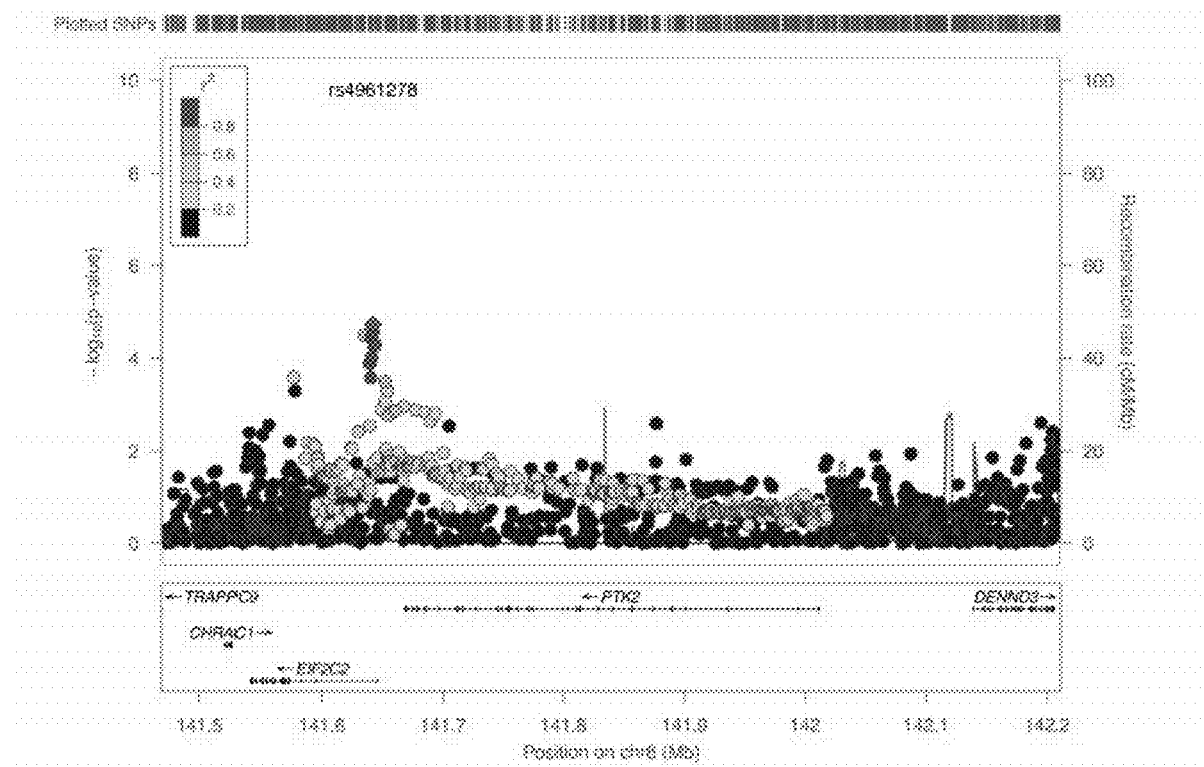
FIG. 17W. PTK2.
Figure 17X:
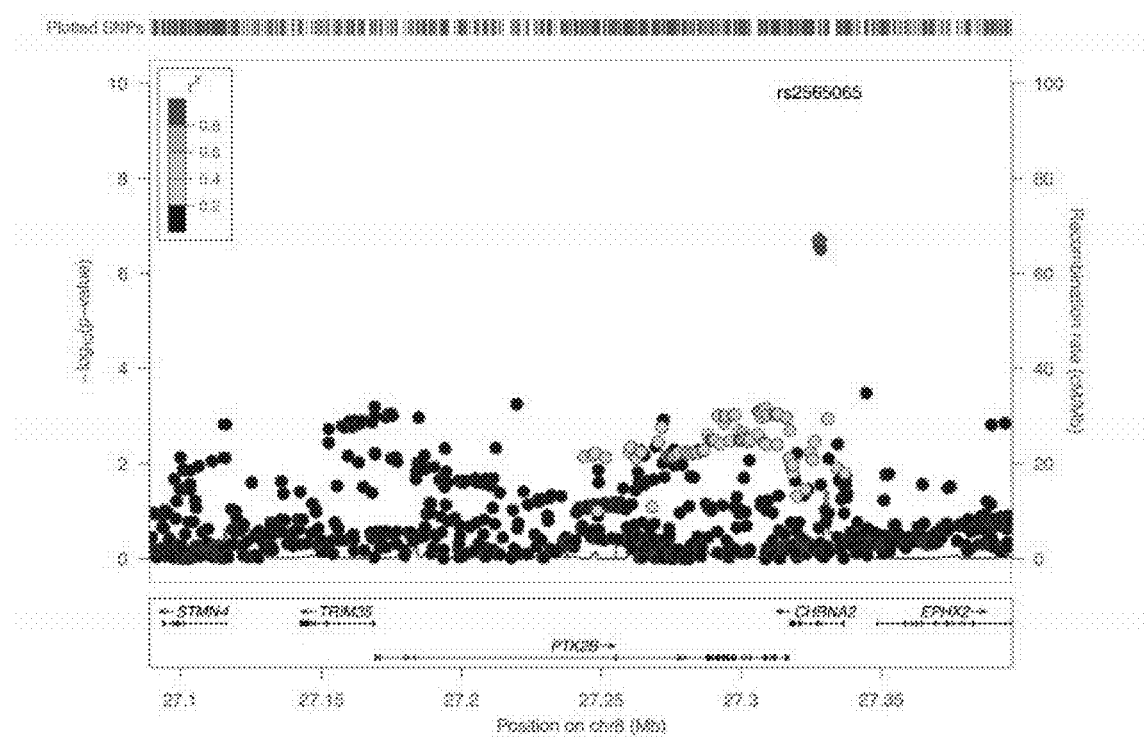
FIG. 17X. PTK2B.
Figure 17Y:
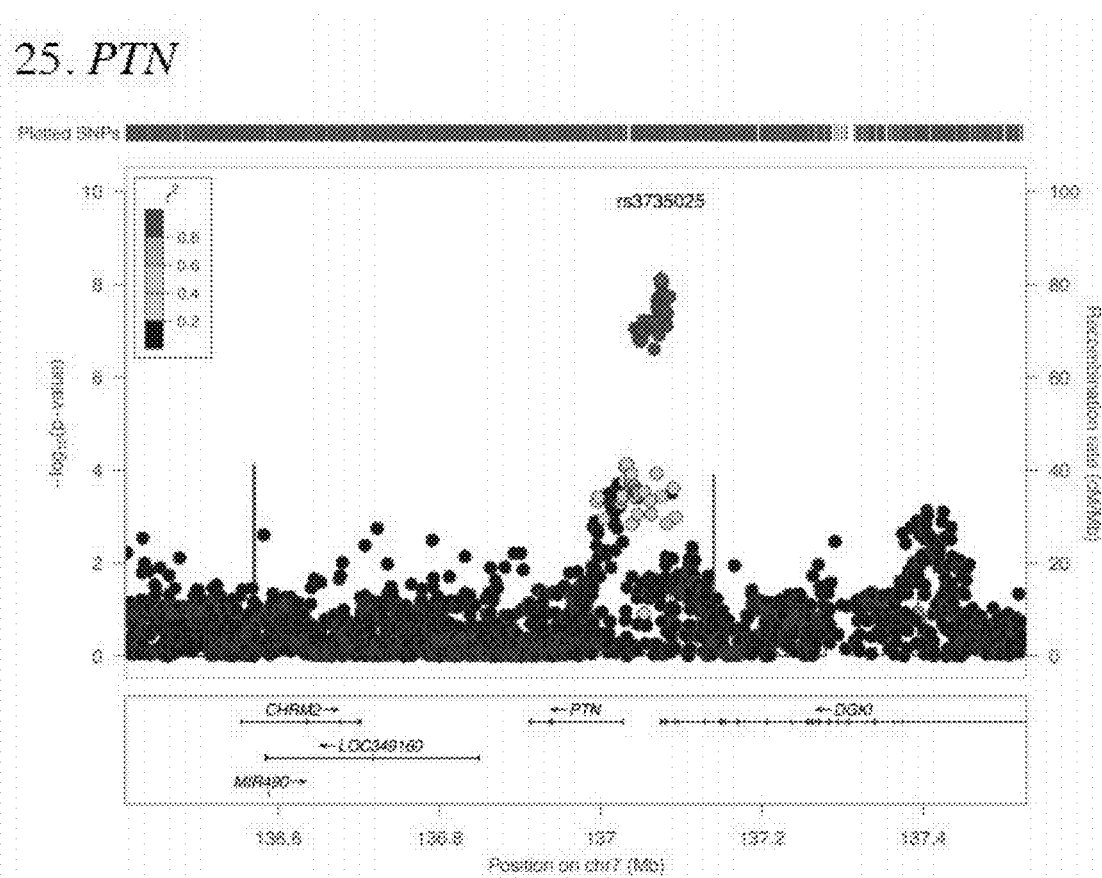
FIG. 17Y. PTN.
Figure 17Z:
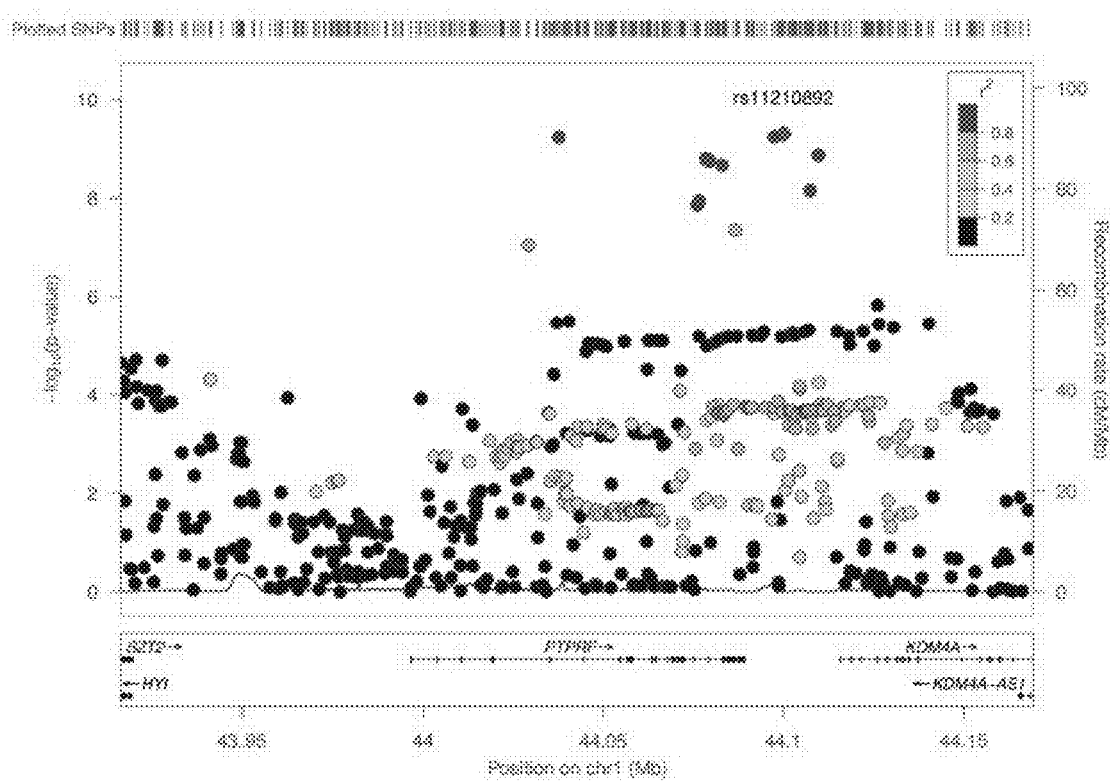
FIG. 17Z. PTPRF.
Figure 17A:
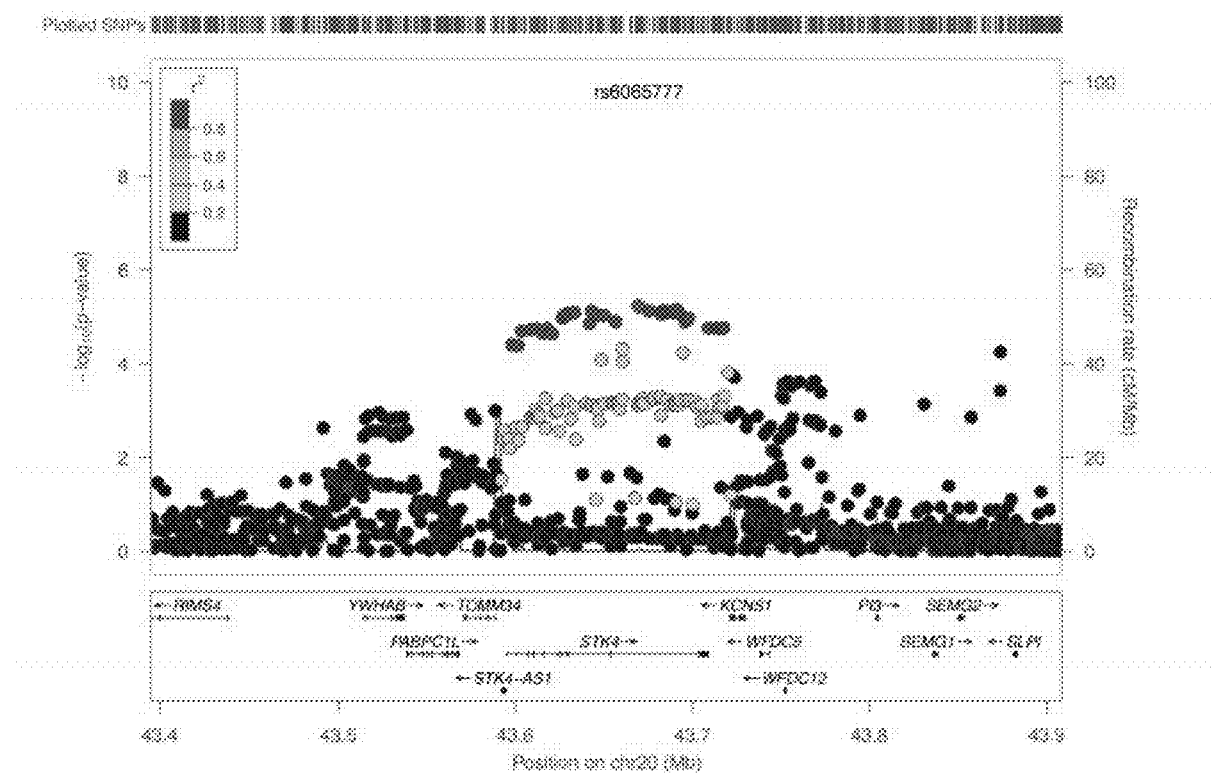
Figure 17B:
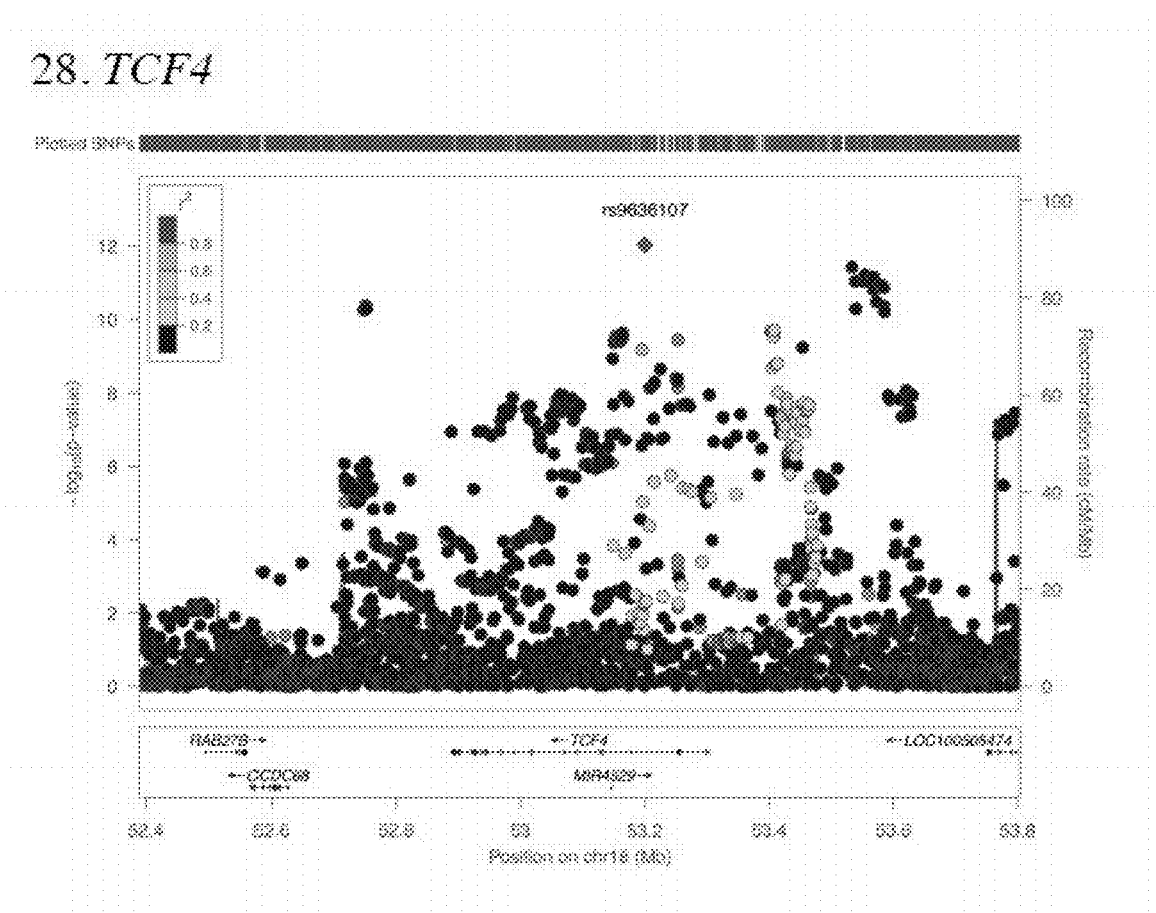

Schematic overview of the network analysis pipeline in this study was provided in FIG. 15E. The PPI Network was constructed based on the database iRefindex, which collected the protein interactions from a number of primary interaction databases [37]. In order to control the rate of false positive interactions, we selected only those interactions that were supported by at least two independent PubMed literatures. A high-confidence network with 9,090 proteins (nodes) and 25,864 interactions (edges) was subsequently built for downstream analyses. We next mapped the significant genes (P<0.05) identified by VEGAS to the PPI network, and obtained a sub-network comprised of the significant genes and the interactions among them. The sub-network contains several connected components and many singletons. We then extracted the largest connected component (LCC) of the sub-network for downstream analysis.

Figure 14A:
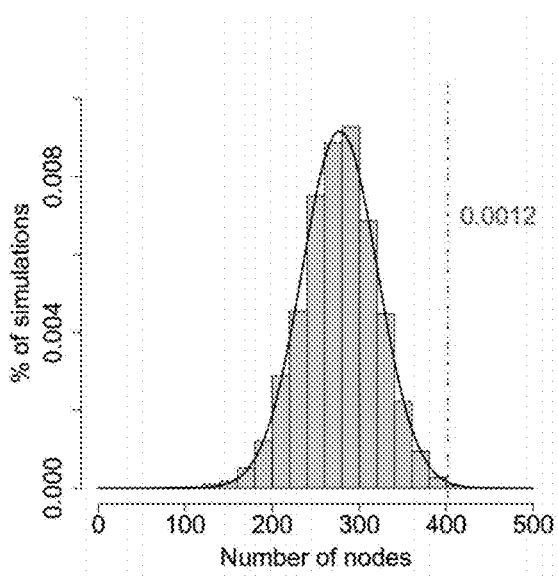
FIGS. 14A-14C. Connectedness of the LCC based on gene-wise significant genes (Pgene <0.01) from PGC2 study. The background distributions are generated by the number of nodes (FIG. 14A) and edges (FIG. 14B) of LCCs from 10,000 random simulations. P values are estimated by the proportion of LCCs from 10,000 random networks with more nodes or edges than the real network. Both node and edge numbers of the real data are significantly larger than random simulations (Pnode=0.0012; Pedge=0.0003).
Figure 14B:
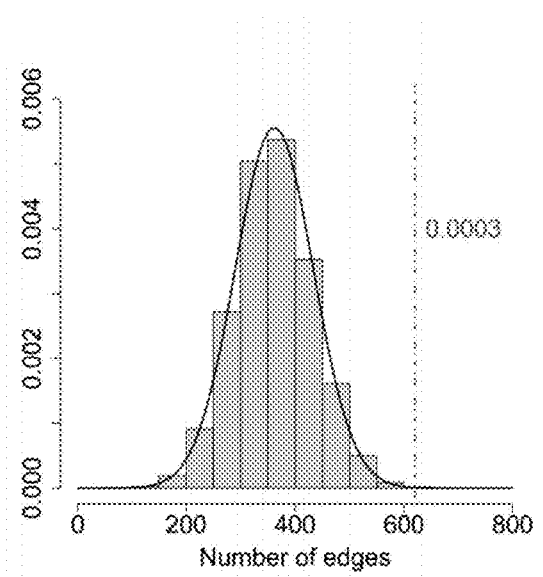

To test whether the size of the LCC is larger than what would be expected by chance, we randomly assigned P values of the same network and generated the simulated LCCs. We repeated this procedure 10,000 times, and use these simulations as background to estimate the significance of the LCCs generated from the real data (FIG. 14 and Table 6). To investigate the biological significance of the genes in the LCC, we carried out a gene function enrichment analysis against the KEGG database using DAVID[38].

TABLE 6

Statistics of LCCs generated by genes with significant gene-wise P values.

| | node | $P_{node}$ | edge | $P_{edge}$ |
|---|---|---|---|---|
| PGC2 ($P_{gene}$ < 0.05) | 1114 | <0.0001 | 2012 | <0.0001 |
| PGC2 ($P_{gene}$ < 0.01) | 402 | 0.0012 | 620 | 0.0003 |
| CD ($P_{gene}$ < 0.05) | 104 | 0.0462 | 136 | 0.0242 |

Gens (GWAS Edge-Based Network Search) Algorithm

Gens algorithm is modified based on a previously published node-based network search method [30, 39, 40]. Gens first assigns a weight to each edge of the network calculated by the gene-wise P values and mRNA expression correlations of interacting gene pairs. See Qiao et al. (Bioinformatics 2014; 30(2): 157-164). The weight of each edge is defined as $$W_{ij} = C_{ij} \times \sqrt{P_i \times P_j}$$

where $C_{ij}$ denotes the Pearson Correlation Coefficient of interacting gene pairs, gene i and gene j. $P_i$ is the P value of Gene i, $P_j$ is the P value of Gene j.

The gene mRNA expression data were downloaded from Allen Brain Atlas (http://human.brain-map.org/static/download) The weight of each edge was then converted into a Z score $$Z_{ij} = \Phi^{-1}(1 - W_{ij})$$

where $\phi^{-1}$ represents the inverse normal cumulative distribution function.

The score of gene module is defined as $$Z_m = \Sigma z_{ij}/\sqrt{k}$$

where k is the number of edges in the module.

The search procedure starts from the seed edge, neighborhood interactors are added into the module if they can yield an increment greater than $Z_m \times r$, r is set to 0.05 in this study.

To evaluate the likelihood of the detected modules were identified by chance, Gens creates a background distribution by scoring 100,000 randomly generated modules with the same number of genes as the detected module. The significance is calculated as the proportion of those random generated modules whose $Z_m$ are larger than or equal to that of the identified module. Gens also adjusted the identified module size by defining a normalized module score $Z_n = (Z_m - mean(Z_m(\pi)))/sd(Z_m(\pi))$, where $Z_m(\pi)$ represents the distribution of $Z_m$ generated by 100,000 simulations.

We have implemented the Gens method in a web service tool, which is available from the URL http://gens.caglab.org.

Results

Figure 14C:
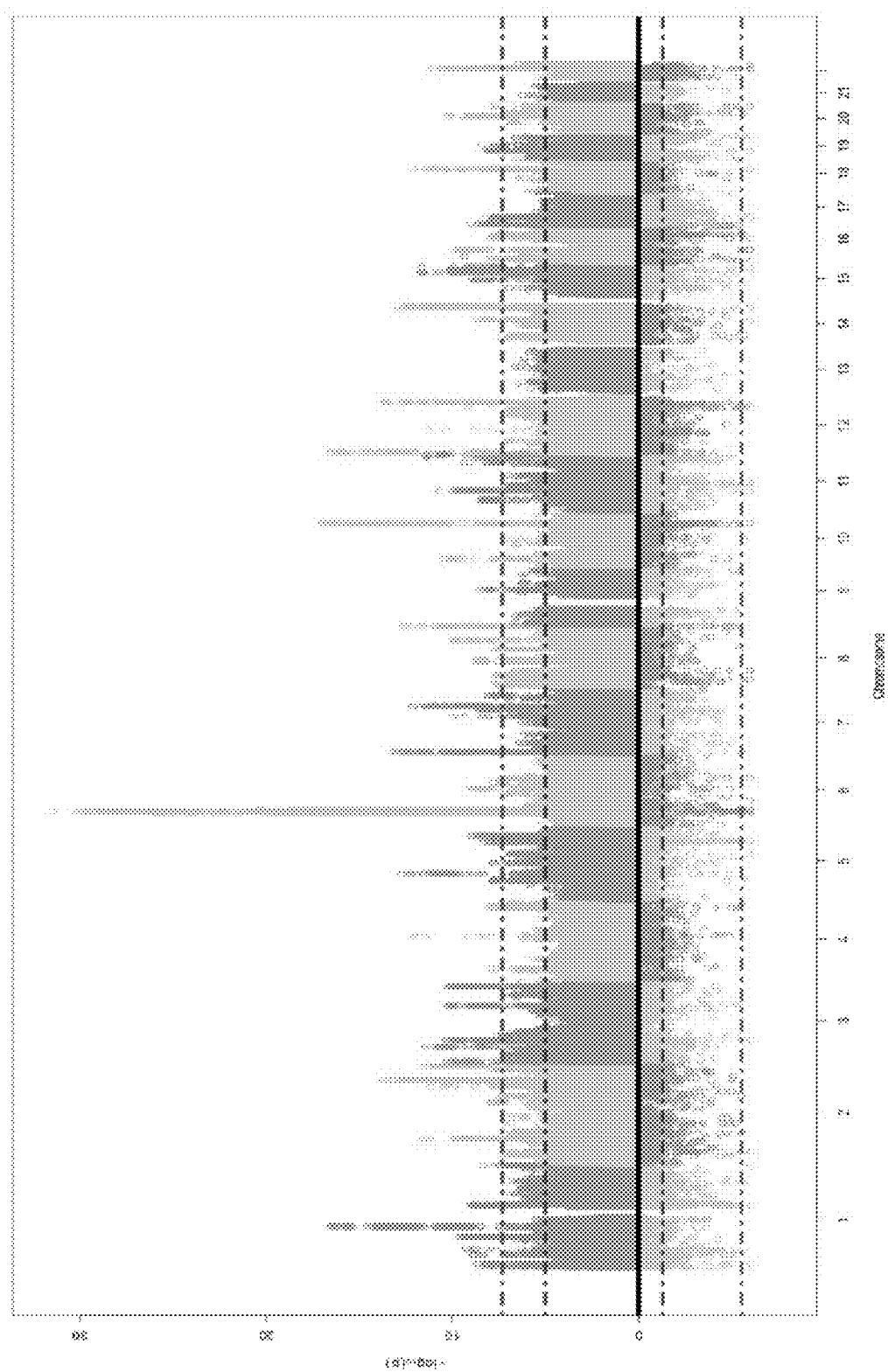

We first used VEGAS to convert the SNP associations into gene-level P values (FIG. 14C). We next extracted the sub-networks by genes with a significant gene-level P value. The identified sub-networks are comprised of connected components and singletons. Among the connected components, the largest connected component (LCC) contains most of the nodes and edges in the sub-network, which may participate in potential pathways underlying schizophrenia. To investigate the biological significance of the LCCs, we carried out a gene function enrichment analysis on the gene set of LCCs. We found significantly over-represented KEGG pathways, which are highly relevant to synaptic plasticity, neural development and signaling transduction such as long-term potentiation, neurotrophin signaling pathway, ERBB signaling pathway, MAPK signaling pathway and T cell receptor signaling pathway. Other enriched pathways include proteasome, ubiquitin mediated proteolysis pathway and multiple cancers associated pathways.

We further confirmed that the sizes of LCCs are significantly larger than the LCCs generated by simulated random networks (FIG. 14 and Table 6). For comparison, we performed the same analysis on a CD cohort, the LCC size is also larger than random simulations (Table 6). This result is consistent with a previous study pointing to a biological plausibility that a set of genes coherently contribute to disease risk through interactive co-function and co-regulation[32].

To examine whether genes belonging to the LCC network and identified by GWAS data are more likely to interact with genes harboring DNMs, we added the genes carrying potential DNMs (frameshift insertions/deletions, missense variants or nonsense variants) and extracted the LCC based on the merged gene set. The size of the LCC significantly increased, larger than 10,000 simulations of the above procedure based on the same number of randomly selected genes. As a control, we tested the same number of top significant genes from CD GWAS. The size of the resulting LCC was not significantly different from random simulations. Furthermore, we also found the size of LCC did not increase significantly than random simulations if genes with silent de novovariants in schizophrenia cases were included (FIG. 15).

In an attempt to add some more understanding to the schizophrenia genetic puzzle, we collected evidence for literature reported genes that are known to be disrupted by CNVs in schizophrenia patients (Table 7), and added them to the PPI network analysis. We subsequently derived the LCC from genes targeted by SNPs, DNMs and CNVs.

TABLE 7

Schizophrenia susceptibility genes from the literature (Genes disrupted by CNVs in schizophrenia patients and three susceptibility genes).

| Gene | CNV | Reference |
|---|---|---|
| DISC1 | No | 4 |
| NRG1 | No | 5 |
| DLG4 | No | 5, 7 |
| ERBB4 | Yes | 8 |
| NRXN1 | Yes | 8-11 |
| MYT1L | Yes | 10 |
| ASTN2 | Yes | 10 |
| CTNND2 | Yes | 10 |
| SLC1A3 | Yes | 8 |
| DLG2 | Yes | 8, 12, 13 |
| PRKCD | Yes | 8 |
| PRKAG2 | Yes | 8 |
| PTK2 | Yes | 8 |
| CAV1 | Yes | 8 |
| PTPRM | Yes | 8 |
| LAMA1 | Yes | 8 |
| MAGI2 | Yes | 8 |
| GRMT | Yes | 8 |
| CNTNAP2 | Yes | 9, 14 |
| VIPR2 | Yes | 11, 15 |
| DLG1 | Yes | 11, 12, 16 |
| PAK2 | Yes | 11, 16 |
| EHMT1 | Yes | 12 |
| DLGAP1 | Yes | 12 |
| CACNA1B | Yes | 17 |
| DOC2A | Yes | 17 |
| RET | Yes | 17 |
| RIT2 | Yes | 17 |

TABLE 7-continued

Schizophrenia susceptibility genes from the literature
(Genes disrupted by CNVs in schizophrenia patients
and three susceptibility genes).

| Gene | CNV | Reference |
|---|---|---|
| BARD1 | Yes | 13 |
| FHIT | Yes | 13 |
| LRP1B | Yes | 13 |
| PRKCA | Yes | 13 |
| CIT | Yes | 13 |
| RAPGEF6 | Yes | 13 |
| PTPRG | Yes | 17 |
| CAMK2D | Yes | 17 |
| PARK2 | Yes | 17 |
| NEDD4L | Yes | 11 |

To pinpoint a small group of interactive genes with significant combined/additive effect to schizophrenia, we developed an edge-based network search algorithm (Gens) for detecting casual gene modules in PPI networks (FIG. 15E). The results from gene-level significance at both 0.05 and 0.01 were highly consistent with each other demonstrating that the top-ranked gene modules overlapped considerably in their gene content. The shared genes between top-ranked modules significantly pointed to the interactome of N-methyl-D-aspartate receptor (NMDAR) genes including DLG1, DLG2, DLG4, ERBB4, GRIN2A and GRIN2B (FIG. 16). All of those genes exhibited strong associations with schizophrenia susceptibility (DLG1, rs436564, $P=8.97\times10^{-4}$; DLG2, rs12294291, $P=4.90\times10^{-7}$; DLG4, rs222854, $P=3.76\times10^{-5}$; ERBB4, rs16846200, $P=1.62\times10^{-5}$; GRIN2A, rs9922678, $P=6.72\times10^{-9}$; GRIN2B, rs11757887, $P=8.81\times10^{-7}$; FIG. 17) with GRIN2A, reaching genome-wide significance in the PGC2 study.

Some of the NMDAR genes are also targeted by rare variations. For example, DLG1 and GRIN2A have been reported to be targeted by DNMs; DLG1, DLG2 and ERBB4 have been reported to be targeted by CNVs. To further explore the risk genes from the PPI network, we next select all the gene modules with P<0.05 (P value calculated by random simulation, see Methods) and calculated the frequency of genes occurring in the selected modules. Genes with the frequency above the upper quartiles were defined as 'top genes'. The 'top genes' was used to construct a new PPI network of 152 nodes and 324 edges (FIG. 16), which reflects the most significant gene module derived from the network analysis.

Enrichment analysis indicated that they are enriched in the neurotrophin signaling pathway ($P=7.27\times10^{-13}$), ERBB signaling pathway ($P=1.84\times10^{-7}$), long-term potentiation ($P=5.37\times10^{-5}$), MAPK signaling pathway ($P=3.16\times10^{-5}$), T cell receptor signaling pathway ($P=1.17\times10^{-5}$), and pathways in cancer ($P=4.87\times10^{-8}$) to name a few. Moreover, in this network, we found multiple genes are connected with the core members of NMDAR interactome, such as ATP2B2, DLGAP, MAP1A, NOS1, PTK2B, PTPRG and PRKCA. Among them, ATP2B2 (rs9879311, $P=2.77\times10^{-6}$) and NOS1 (rs2293052, $P=1.24\times10^{-6}$) exhibited strong associations with schizophrenia risk in the PGC2 GWAS.

Beside the NMDAR interactome, we also found candidate genes showing strong associations with schizophrenia risk in the network, such as ANKS1B (rs10745841, $P=1.28\times10^{-6}$), CHUK (rs975752, $P=2.52\times10^{-6}$), CNTN2 (rs16937, $P=8.69\times10^{-7}$), CNTNAP2 (rs6961013, $P=4.80\times10^{-5}$), CREB1 (rs2709410, $P=4.07\times10^{-6}$), CREB5 (rs4722797, $P=7.58\times10^{-6}$; rs887622, $P=8.79\times10^{-6}$), CUL3 (rs11685299, $P=1.11\times10^{-8}$), EP300 (rs9607782, $P=6.76\times10^{-12}$), GABBR2 (rs2304389, $P=3.81\times10^{-7}$), GNA13 (rs11868185, $P=4.44\times10^{-5}$), NCOR2 (rs2229840, $P=2.90\times10^{-4}$), NTRK3 (rs146797905, $P=3.35\times10^{-7}$; rs8042993, $P=7.84\times10^{-6}$), PAK2 (rs10446497, $P=5.30\times10^{-6}$), PTK2 (rs4961278, $P=1.86\times10^{-5}$), PTK2B (rs2565065, $P=1.94\times10^{-7}$), PTN (rs3735025, $P=7.75\times10^{-9}$), PTPRF (rs11210892, $P=4.97\times10^{-10}$), STK4 (rs6065777, $P=5.92\times10^{-6}$), TCF4 (rs9636107, $P=9.09\times10^{-13}$). Among them, CUL3, EP300, NCOR2, PTK2B and PTPRF were targeted by DNMs, and PAK2, PARK2 and PTK2 were targeted by CNVs.

DISCUSSION

Given the heterogeneity and complexity of the genomic landscape in schizophrenia, we employed multiple network-based methods to reveal the instinct associations among different types of genetic risk variants, resulting in the discovery of novel gene modules and pathways underlying schizophrenia (FIG. 15).

With the recent GWAS success measures in schizophrenia uncovering 108 genome-wide significant loci [16], the genetic underpinnings of this complex disease have begun to unravel. However, a considerable number of nominally significant loci are likely to be identified in future studies through the analysis of larger sample sizes or the application of new and innovative methods. For example, the schizophrenia susceptibility gene CAMKK2 showing nominal significance (rs1063843, $P=2.32\times10^{-5}$) in the PGG2 study was successfully identified by integrative analysis of gene expression and PPI [41].

We hypothesize that a group of functionally related genes with nominal significance could jointly contribute to schizophrenia susceptibility. We further performed a PPI network-based pathway analysis on two GWA studies of schizophrenia and identified significantly enriched KEGG pathways in both studies. Some pathways have been strongly associated with schizophrenia, such as the long-term potentiation, ERBB signaling pathway and MAPK signaling pathway [42-46]. Interestingly, we found both the proteasome pathway and the ubiquitin mediated proteolysis pathway to be significantly enriched. Dysfunction of the ubiquitin-proteasome pathway (UPP) has been implicated in the pathology of various neurodegenerative conditions, and has been linked to several late-onset neurodegenerative diseases caused by aggregate-prone proteins such as Alzheimer's disease Parkinson's disease and Huntington's disease [47,48]. Cumulative evidence also suggests that schizophrenia patients have aberrant gene expression patterns and protein expression disruptions in the UPP suggesting the UPP may also contribute to the deficits in schizophrenia [49-53]. Our results are consistent with these findings and provide new evidence in support of the association between the UPP and the pathogenesis of schizophrenia.

Figure 18:
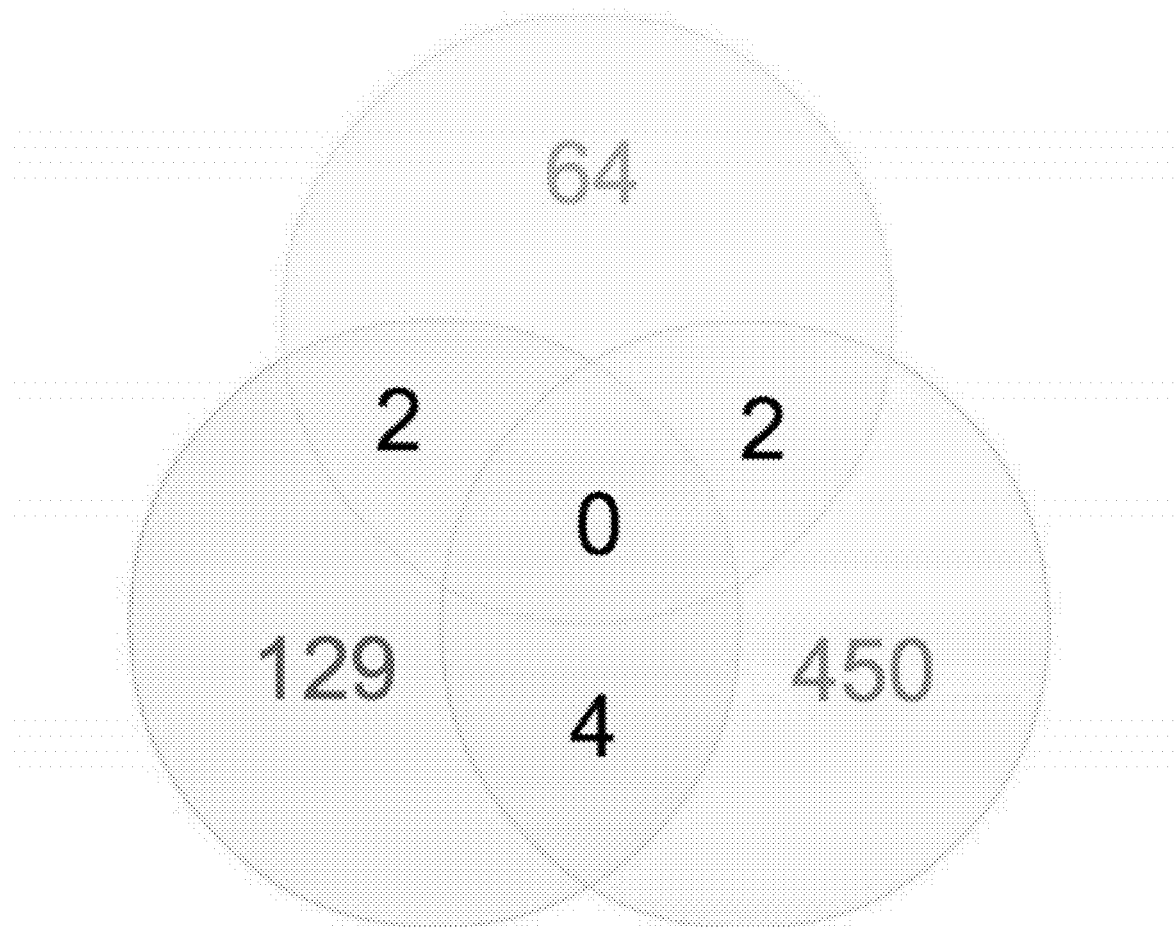
FIG. 18. Venn diagram summarizes the number of shared genes disrupted by DNMs in three exome sequencing studies of schizophrenia.

Cumulative evidence suggests that DNMs are an important cause of mental disorders such as schizophrenia, autism and intellectual disability [54]. DNMs occur in different genes of different patients may be collectively responsible for a portion of sporadic schizophrenia cases. However, unlike CNVs, genes recurrently mutated by SNVs are rare and the overlap of genes disrupted by DNMs from recent studies is also small (FIG. 18). Thus, we naturally raise the question if genes targeted by common SNPs are more likely to be targeted by DNMs, and if genes targeted by common SNPs are more likely to interact with genes carrying DNMs? For the first question, the PGC2 study unveiled significant overlap between genes in the schizophrenia GWAS associated intervals and those with DNMs in schizophrenia (P=0.0061)[16]. For the second question, our analysis provides new evidence suggesting that genes targeted by common SNPs or DNMs are likely to interact with each other or participant in the same pathway. Collectively, these results suggest that schizophrenia susceptibility involves a mutual interplay of both common and rare genetic risk factors.

We additionally developed an edge-based network search algorithm to identify the leading disease associated modules underlying schizophrenia. The network search method was initially node-based, and developed in order to detect a group of interactive genes which show significantly changes in mRNA expression [39]. Later, this method was successfully applied on the post-GWAS network analysis[24, 30-32]. Here, the advantage of Gens is that the edge-based method can utilize not only the node P values for the node but also the gene co-expression information as edge weights to score and rank the detected modules (Methods).

Using this approach, we found the top-ranked modules were significantly enriched in the NMDAR pathway associated genes including DLG1, DLG2, DLG4, ERBB4, GRIN2A, and GRIN2B. All of those genes show strong association with schizophrenia from GWAS. DLG1, DLG2, ERBB4 and GRIN2A were also targeted by DNMs or CNVs. In addition to GRIN2A, which has surpassed genome-wide significance (rs9922678, P=$6.72 \times 10^{-9}$) in the PGC2 study, DLG2 (rs12294291, P=$4.90 \times 10^{-7}$), GRIN2B (rs11757887, P=$8.81 \times 10^{-7}$) also showed strong associations nearly reaching genome-wide significance. These results suggested that the dysfunction of the NMDAR complex plays a leading role in the pathology of schizophrenia and is highly impacted by multiple genetic risk factors.

We further pinpointed two genes ATP2B2 (rs9879311, P=$2.77 \times 10^{-6}$) and NOS1 (rs2293052, P=$1.24 \times 10^{-6}$), which were closely connected to the NMDAR interactome and showed strong associations with schizophrenia risk. ATP2B2 encodes the plasma membrane calcium-transporting ATPase 2 which plays an important role in intracellular calcium homeostasis and extrudes $Ca^{2+}$ from cytosol into extracellular space. Family-based association studies suggested ATP2B2 as a risk gene for autism in multiple ethnicities [55-57]. A previous study also suggested ATP2B2 could confer risk to schizophrenia [58]. NOS1 encodes a member of nitric oxide synthases, which functions as a biologic mediator in neurotransmission. Previous studies also provided evidence of the associations between NOS1 and schizophrenia risk [59-61]. Besides the NMDAR interactome, CUL3, EP300, PTN, PTPRF, TCF4 reached genome-wide significance in the PGC2 study. CUL3, EP300 and PTPRF were also targeted by DNMs). EP300 servers as an important hub in the network which directly interacted with 14 genes (TCF4, EGR1, SREBF1 and SREBF2 located in genome-wide significant regions; AKT1 and SMAD7 targeted by DNMs). The product of EP300 functions as histone acetyltransferase and regulates transcription via chromatin remodeling. Defects of EP300 can cause Rubinstein-Taybi syndrome (a disease with short stature and intellectual disability) and may result in the formation of tumors[62-64]. Interestingly, the DNM (NM_001429, exon14, c.C2656G, p.P886A) found in EP300 is not predicted as damaging by either SIFT nor PolyPhen2, and a common missense variant in EP300 is also strongly associated with schizophrenia (rs20551, P=$1.38 \times 10^{-8}$; NM_001429, exon15, c.A2989G, p.I997V), which suggest that slight changes in the protein conformation of EP300 may confer risk to schizophrenia. EP300 is also interacted and co-expressed with CREB1 in the network. It is reported that EP300 can mediate cAMP-gene regulation through phosphorylated CREB proteins. CREB1 also showed strong association (rs2709410, P=$4.07 \times 10^{-6}$) in the PGC2 study. CREB1 has been linked to drug addiction, memory disorders and neurodegenerative diseases [65-68]. There is also some evidence of the association between CREB1 and schizophrenia [69-71]. PTN is another important hub, which interacted with eight genes (NCAN, PSMB10 and SGSM2 located in genome-wide significant regions; NCAN, PSMD2 and SGSM2 targeted by DNMs). PTN encodes pleiotrophin, which may suppress long-term potentiation induction[72]. In the network, candidate genes with nominal significance such as ANKS1B, CNTN2, CNTNAP2, GABBR2, NCOR2 and NTRK3 also may be involved in the pathology of schizophrenia. The product of ANKS1B is predominantly expressed in brain tissue and interacted with amyloid beta protein precursor, which may play a role in brain development. A recent study demonstrated that ANKS1B product regulates synaptic GluN2B levels and further influence the NMDAR function. Multiple pieces of evidence have linked CNTN2, CNTNAP2, GABBR2, and NTRK3 to neuropsychiatric disorders, including schizophrenia [3, 46, 73-79]. SNPs in NCOR2 are associated with cocaine dependence in a recent GWAS [80].

In conclusion, the heterogeneity and complexity of the genetic landscape in schizophrenia is high. Here, we demonstrate that common and rare genetic risk factors converge on PPI networks that are enriched for schizophrenia candidate genes involved in synaptic plasticity and neural development. We also provide new evidence demonstrating that the NMDAR interactome is highly targeted by multiple types of genetic risk factors and may play a leading role in the risk of schizophrenia. Furthermore, we pinpointed many nominally significant genes in GWAS showing strong evidence to influence schizophrenia risk according to their network properties.

References For Example IV

1. Ripke S, O'Dushlaine C, Chambert K, Moran J L, Kahler A K, Akterin S et al. Genome-wide association analysis identifies 13 new risk loci for schizophrenia. *Nature genetics* 2013; 45(10): 1150-1159.
2. Sleiman P, Wang D, Glessner J, Hadley D, Gur R E, Cohen N et al. GWAS meta analysis identifies TSNARE1 as a novel Schizophrenia/Bipolar susceptibility locus. *Scientific reports* 2013; 3: 3075.
3. Friedman J I, Vrijenhoek T, Markx S, Janssen I M, van der Vliet W A, Faas B H et al. CNTNAP2 gene dosage variation is associated with schizophrenia and epilepsy. *Molecular psychiatry* 2008; 13(3): 261-266.
4. International Schizophrenia C. Rare chromosomal deletions and duplications increase risk of schizophrenia. *Nature* 2008; 455(7210): 237-241.
5. Levinson D F, Duan J, Oh S, Wang K, Sanders A R, Shi J et al. Copy number variants in schizophrenia: confirmation of five previous findings and new evidence for 3q29 microdeletions and VIPR2 duplications. *The American journal of psychiatry* 2011; 168(3): 302-316.
6. Mulle J G, Dodd A F, McGrath J A, Wolyniec P S, Mitchell A A, Shetty A C et al. Microdeletions of 3q29 confer high risk for schizophrenia. *American journal of human genetics* 2010; 87(2): 229-236.
7. Vacic V, McCarthy S, Malhotra D, Murray F, Chou H H, Peoples A et al. Duplications of the neuropeptide receptor gene VIPR2 confer significant risk for schizophrenia. *Nature* 2011; 471(7339): 499-503.

8. Vrijenhoek T, Buizer-Voskamp J E, van der Stelt I, Strengman E, Genetic R, Outcome in Psychosis C et al. Recurrent CNVs disrupt three candidate genes in schizophrenia patients. *American journal of human genetics* 2008; 83(4): 504-510.
9. Walsh T, McClellan J M, McCarthy S E, Addington A M, Pierce S B, Cooper G M et al. Rare structural variants disrupt multiple genes in neurodevelopmental pathways in schizophrenia. *Science* 2008; 320(5875): 539-543.
10. Glessner J T, Reilly M P, Kim C E, Takahashi N, Albano A, Hou C et al. Strong synaptic transmission impact by copy number variations in schizophrenia. *Proceedings of the National Academy of Sciences of the United States of America* 2010; 107(23): 10584-10589.
11. Fromer M, Pocklington A J, Kavanagh D H, Williams H J, Dwyer S, Gormley P et al. De novo mutations in schizophrenia implicate synaptic networks. *Nature* 2014; 506(7487): 179-184.
12. Girard S L, Gauthier J, Noreau A, Xiong L, Zhou S, Jouan L et al. Increased exonic de novo mutation rate in individuals with schizophrenia. *Nature genetics* 2011; 43(9): 860-863.
13. Kirov G, Pocklington A J, Holmans P, Ivanov D, Ikeda M, Ruderfer D et al. De novo CNV analysis implicates specific abnormalities of postsynaptic signalling complexes in the pathogenesis of schizophrenia. *Molecular psychiatry* 2012; 17(2): 142-153.
14. Xu B, Ionita-Laza I, Roos J L, Boone B, Woodrick S, Sun Y et al. De novo gene mutations highlight patterns of genetic and neural complexity in schizophrenia. *Nature genetics* 2012; 44(12): 1365-1369.
15. Xu B, Roos J L, Levy S, van Rensburg E J, Gogos J A, Karayiorgou M. Strong association of de novo copy number mutations with sporadic schizophrenia. *Nature genetics* 2008; 40(7): 880-885.
16. Schizophrenia Working Group of the Psychiatric Genomics C. Biological insights from 108 schizophrenia-associated genetic loci. *Nature* 2014; 511(7510): 421-427.
17. Lee S H, DeCandia T R, Ripke S, Yang J, Schizophrenia Psychiatric Genome-Wide Association Study C, International Schizophrenia C et al. Estimating the proportion of variation in susceptibility to schizophrenia captured by common SNPs. *Nature genetics* 2012; 44(3): 247-250.
18. Bergen S E, O'Dushlaine C T, Ripke S, Lee P H, Ruderfer D M, Akterin S et al. Genome-wide association study in a Swedish population yields support for greater CNV and MHC involvement in schizophrenia compared with bipolar disorder. *Molecular psychiatry* 2012; 17(9): 880-886.
19. Szatkiewicz J P, O'Dushlaine C, Chen G, Chambert K, Moran J L, Neale B M et al. Copy number variation in schizophrenia in Sweden. *Molecular psychiatry* 2014; 19(7): 762-773.
20. Gulsuner S, Walsh T, Watts A C, Lee M K, Thornton A M, Casadei S et al. Spatial and temporal mapping of de novo mutations in schizophrenia to a fetal prefrontal cortical network. *Cell* 2013; 154(3): 518-529.
21. McCarthy S E, Gillis J, Kramer M, Lihm J, Yoon S, Berstein Y et al. De novo mutations in schizophrenia implicate chromatin remodeling and support a genetic overlap with autism and intellectual disability. *Molecular psychiatry* 2014; 19(6): 652-658.
22. Luo X, Huang L, Jia P, Li M, Su B, Zhao Z et al. Protein-protein interaction and pathway analyses of top schizophrenia genes reveal schizophrenia susceptibility genes converge on common molecular networks and enrichment of nucleosome (chromatin) assembly genes in schizophrenia susceptibility loci. *Schizophrenia bulletin* 2014; 40(1): 39-49.
23. Luo X, Huang L, Han L, Luo Z, Hu F, Tieu R et al. Systematic prioritization and integrative analysis of copy number variations in schizophrenia reveal key schizophrenia susceptibility genes. *Schizophrenia bulletin* 2014; 40(6): 1285-1299.
24. Jia P, Wang L, Fanous A H, Pato C N, Edwards T L, International Schizophrenia C et al. Network-assisted investigation of combined causal signals from genome-wide association studies in schizophrenia. *PLoS computational biology* 2012; 8(7): e1002587.
25. Bullmore E, Sporns O. Complex brain networks: graph theoretical analysis of structural and functional systems. *Nature reviews Neuroscience* 2009; 10(3): 186-198.
26. Gilman S R, Chang J, Xu B, Bawa T S, Gogos J A, Karayiorgou M et al. Diverse types of genetic variation converge on functional gene networks involved in schizophrenia. *Nature neuroscience* 2012; 15(12): 1723-1728.
27. Chang X, Xu T, Li Y, Wang K. Dynamic modular architecture of protein-protein interaction networks beyond the dichotomy of 'date' and 'party' hubs. *Scientific reports* 2013; 3: 1691.
28. Zhou X, Menche J, Barabasi A L, Sharma A. Human symptoms-disease network. *Nature communications* 2014; 5: 4212.
29. Barabasi A L, Gulbahce N, Loscalzo J. Network medicine: a network-based approach to human disease. *Nature reviews Genetics* 2011; 12(1): 56-68.
30. Jia P, Zheng S, Long J, Zheng W, Zhao Z. dmGWAS: dense module searching for genome-wide association studies in protein-protein interaction networks. *Bioinformatics* 2011; 27(1): 95-102.
31. Han S, Yang B Z, Kranzler H R, Liu X, Zhao H, Farrer L A et al. Integrating GWASs and human protein interaction networks identifies a gene subnetwork underlying alcohol dependence. *American journal of human genetics* 2013; 93(6): 1027-1034.
32. International Multiple Sclerosis Genetics C. Network-based multiple sclerosis pathway analysis with GWAS data from 15,000 cases and 30,000 controls. *American journal of human genetics* 2013; 92(6): 854-865.
33. Leiserson M D, Eldridge J V, Ramachandran S, Raphael B J. Network analysis of GWAS data. *Current opinion in genetics & development* 2013; 23(6): 602-610.
34. Jostins L, Ripke S, Weersma R K, Duerr R H, McGovern D P, Hui K Y et al. Host-microbe interactions have shaped the genetic architecture of inflammatory bowel disease. *Nature* 2012; 491(7422): 119-124.
35. Liu J Z, McRae A F, Nyholt D R, Medland S E, Wray N R, Brown K M et al. A versatile gene-based test for genome-wide association studies. *American journal of human genetics* 2010; 87(1): 139-145.
36. Chang X, Wang K. wANNOVAR: annotating genetic variants for personal genomes via the web. *Journal of medical genetics* 2012; 49(7): 433-436.
37. Razick S, Magklaras G, Donaldson I M. iRefIndex: a consolidated protein interaction database with provenance. *BMC bioinformatics* 2008; 9: 405.
38. Huang da W, Sherman B T, Tan Q, Kir J, Liu D, Bryant D et al. DAVID Bioinformatics Resources: expanded annotation database and novel algorithms to better extract biology from large gene lists. *Nucleic acids research* 2007; 35(Web Server issue): W169-175.

39. Ideker T, Ozier O, Schwikowski B, Siegel A F. Discovering regulatory and signalling circuits in molecular interaction networks. *Bioinformatics* 2002; 18 Suppl 1: S233-240.
40. Chuang H Y, Lee E, Liu Y T, Lee D, Ideker T. Network-based classification of breast cancer metastasis. *Molecular systems biology* 2007; 3: 140.
41. Luo X J, Li M, Huang L, Steinberg S, Mattheisen M, Liang G et al. Convergent lines of evidence support CAMKK2 as a schizophrenia susceptibility gene. *Molecular psychiatry* 2014; 19(7): 774-783.
42. Salavati B, Rajji T K, Price R, Sun Y, Graff-Guerrero A, Daskalakis Z J. Imaging-based neurochemistry in schizophrenia: a systematic review and implications for dysfunctional long-term potentiation. *Schizophrenia bulletin* 2015; 41(1): 44-56.
43. Savanthrapadian S, Wolff A R, Logan B J, Eckert M J, Bilkey D K, Abraham W C. Enhanced hippocampal neuronal excitability and LTP persistence associated with reduced behavioral flexibility in the maternal immune activation model of schizophrenia. *Hippocampus* 2013; 23(12): 1395-1409.
44. Funk A J, McCullumsmith R E, Haroutunian V, Meador-Woodruff J H. Abnormal activity of the MAPK- and cAMP-associated signaling pathways in frontal cortical areas in postmortem brain in schizophrenia. *Neuropsychopharmacology: official publication of the American College of Neuropsychopharmacology* 2012; 37(4): 896-905.
45. Pitcher G M, Kalia L V, Ng D, Goodfellow N M, Yee K T, Lambe E K et al. Schizophrenia susceptibility pathway neuregulin 1-ErbB4 suppresses Src upregulation of NMDA receptors. *Nature medicine* 2011; 17(4): 470-478.
46. Fazzari P, Paternain A V, Valiente M, Pla R, Lujan R, Lloyd K et al. Control of cortical GABA circuitry development by Nrg1 and ErbB4 signalling. *Nature* 2010; 464(7293): 1376-1380.
47. Rubinsztein D C. The roles of intracellular protein-degradation pathways in neurodegeneration. *Nature* 2006; 443(7113): 780-786.
48. Hegde A N, Upadhya S C. Role of ubiquitin-proteasome-mediated proteolysis in nervous system disease. *Biochimica et biophysica acta* 2011; 1809(2): 128-140.
49. Vawter M P, Barrett T, Cheadle C, Sokolov B P, Wood W H, 3rd, Donovan D M et al. Application of cDNA microarrays to examine gene expression differences in schizophrenia. *Brain research bulletin* 2001; 55(5): 641-650.
50. Aston C, Jiang L, Sokolov B P. Microarray analysis of postmortem temporal cortex from patients with schizophrenia. *Journal of neuroscience research* 2004; 77(6): 858-866.
51. Altar C A, Jurata L W, Charles V, Lemire A, Liu P, Bukhman Y et al. Deficient hippocampal neuron expression of proteasome, ubiquitin, and mitochondrial genes in multiple schizophrenia cohorts. *Biological psychiatry* 2005; 58(2): 85-96.
52. Bousman C A, Chana G, Glatt S J, Chandler S D, Lucero G R, Tatro E et al. Preliminary evidence of ubiquitin proteasome system dysregulation in schizophrenia and bipolar disorder: convergent pathway analysis findings from two independent samples. *American journal of medical genetics Part B, Neuropsychiatric genetics: the official publication of the International Society of Psychiatric Genetics* 2010; 153B(2): 494-502.
53. Rubio M D, Wood K, Haroutunian V, Meador-Woodruff J H. Dysfunction of the ubiquitin proteasome and ubiquitin-like systems in schizophrenia. *Neuropsychopharmacology: official publication of the American College of Neuropsychopharmacology* 2013; 38(10): 1910-1920.
54. Veltman J A, Brunner H G. De novo mutations in human genetic disease. *Nature reviews Genetics* 2012; 13(8): 565-575.
55. Carayol J, Sacco R, Tores F, Rousseau F, Lewin P, Hager J et al. Converging evidence for an association of ATP2B2 allelic variants with autism in male subjects. *Biological psychiatry* 2011; 70(9): 880-887.
56. Yang W, Liu J, Zheng F, Jia M, Zhao L, Lu T et al. The evidence for association of ATP2B2 polymorphisms with autism in Chinese Han population. *PloS one* 2013; 8(4): e61021.
57. Prandini P, Pasquali A, Malerba G, Marostica A, Zusi C, Xumerle L et al. The association of rs4307059 and rs35678 markers with autism spectrum disorders is replicated in Italian families. *Psychiatric genetics* 2012; 22(4): 177-181.
58. Ikeda M, Tomita Y, Mouri A, Koga M, Okochi T, Yoshimura R et al. Identification of novel candidate genes for treatment response to risperidone and susceptibility for schizophrenia: integrated analysis among pharmacogenomics, mouse expression, and genetic case-control association approaches. *Biological psychiatry* 2010; 67(3): 263-269.
59. Shinkai T, Ohmori O, Hori H, Nakamura J. Allelic association of the neuronal nitric oxide synthase (NOS1) gene with schizophrenia. *Molecular psychiatry* 2002; 7(6): 560-563.
60. Zhang Z, Chen X, Yu P, Zhang Q, Sun X, Gu H et al. Evidence for the Contribution of NOS1 Gene Polymorphism (rs3782206) to Prefrontal Function in Schizophrenia Patients and Healthy Controls. *Neuropsychopharmacology: official publication of the American College of Neuropsychopharmacology* 2014.
61. Reif A, Schecklmann M, Eirich E, Jacob C P, Jarczok T A, Kittel-Schneider S et al. A functional promoter polymorphism of neuronal nitric oxide synthase moderates prefrontal functioning in schizophrenia. *The international journal of neuropsychopharmacology/official scientific journal of the Collegium Internationale Neuropsychopharmacologicum* 2011; 14(7): 887-897.
62. Tillinghast G W, Partee J, Albert P, Kelley J M, Burtow K H, Kelly K. Analysis of genetic stability at the EP300 and CREBBP loci in a panel of cancer cell lines. *Genes, chromosomes & cancer* 2003; 37(2): 121-131.
63. Negri G, Milani D, Colapietro P, Forzano F, Della Monica M, Rusconi D et al. Clinical and molecular characterization of Rubinstein-Taybi syndrome patients carrying distinct novel mutations of the EP300 gene. *Clinical genetics* 2015; 87(2): 148-154.
64. Roelfsema J H, White S J, Ariyurek Y, Bartholdi D, Niedrist D, Papadia F et al. Genetic heterogeneity in Rubinstein-Taybi syndrome: mutations in both the CBP and EP300 genes cause disease. *American journal of human genetics* 2005; 76(4): 572-580.
65. Josselyn S A, Nguyen P V. CREB, synapses and memory disorders: past progress and future challenges. *Current drug targets CNS and neurological disorders* 2005; 4(5): 481-497.
66. Lee J, Kim C H, Simon D K, Aminova L R, Andreyev A Y, Kushnareva Y E et al. Mitochondrial cyclic AMP response element-binding protein (CREB) mediates mitochondrial gene expression and neuronal survival. *The Journal of biological chemistry* 2005; 280(49): 40398-40401.

67. Nestler E J. Common molecular and cellular substrates of addiction and memory. *Neurobiology of learning and memory* 2002; 78(3): 637-647.
68. Bilecki W, Przewlocki R. Effect of opioids on Ca2+/cAMP responsive element binding protein. *Acta neurobiologiae experimentalis* 2000; 60(4): 557-567.
69. Li S, Liu Z C, Yin S J, Chen Y T, Yu H L, Zeng J et al. Human endogenous retrovirus W family envelope gene activates the small conductance Ca2+-activated K+ channel in human neuroblastoma cells through CREB. *Neuroscience* 2013; 247: 164-174.
70. Kumar G, Clark S L, McClay J L, Shabalin A A, Adkins D E, Xie L et al. Refinement of schizophrenia GWAS loci using methylome-wide association data. *Human genetics* 2015; 134(1): 77-87.
71. Ma L, Wu D D, Ma S L, Tan L, Chen X, Tang N L et al. Molecular evolution in the CREB1 signal pathway and a rare haplotype in CREB1 with genetic predisposition to schizophrenia. *Journal of psychiatric research* 2014; 57: 84-89.
72. Pavlov I, Voikar V, Kaksonen M, Lauri S E, Hienola A, Taira T et al. Role of heparin-binding growth-associated molecule (HB-GAM) in hippocampal LTP and spatial learning revealed by studies on overexpressing and knockout mice. *Molecular and cellular neurosciences* 2002; 20(2): 330-342.
73. Weickert C S, Ligons D L, Romanczyk T, Ungaro G, Hyde T M, Herman M M et al. Reductions in neurotrophin receptor mRNAs in the prefrontal cortex of patients with schizophrenia. *Molecular psychiatry* 2005; 10(7): 637-650.
74. Otnaess M K, Djurovic S, Rimol L M, Kulle B, Kahler A K, Jonsson E G et al. Evidence for a possible association of neurotrophin receptor (NTRK-3) gene polymorphisms with hippocampal function and schizophrenia. *Neurobiology of disease* 2009; 34(3): 518-524.
75. Fatemi S H, Folsom T D, Thuras P D. Deficits in GABA(B) receptor system in schizophrenia and mood disorders: a postmortem study. *Schizophrenia research* 2011; 128(1-3): 37-43.
76. Roussos P, Katsel P, Davis K L, Bitsios P, Giakoumaki S G, Jogia J et al. Molecular and genetic evidence for abnormalities in the nodes of Ranvier in schizophrenia. *Archives of general psychiatry* 2012; 69(1): 7-15.
77. Bormuth I, Yan K, Yonemasu T, Gummert M, Zhang M, Wichert S et al. Neuronal basic helix-loop-helix proteins Neurod2/6 regulate cortical commissure formation before midline interactions. *The Journal of neuroscience: the official journal of the Society for Neuroscience* 2013; 33(2): 641-651.
78. Fatemi S H, Folsom T D, Rooney R J, Thuras P D. Expression of GABAA alpha2-, beta1- and epsilon-receptors are altered significantly in the lateral cerebellum of subjects with schizophrenia, major depression and bipolar disorder. *Translational psychiatry* 2013; 3: e303.
79. Karayannis T, Au E, Patel J C, Kruglikov I, Markx S, Delorme R et al. Cntnap4 differentially contributes to GABAergic and dopaminergic synaptic transmission. *Nature* 2014; 511(7508): 236-240.
80. Gelernter J, Sherva R, Koesterer R, Almasy L, Zhao H, Kranzler H R et al. Genome-wide association study of cocaine dependence and related traits: FAM53B identified as a risk gene. *Molecular psychiatry* 2014; 19(6): 717-723.

EXAMPLE V

Test and Treat Method for Ameliorating Symptoms Associated with Schizophrenia and Bi-Polar Disease In order to treat an individual having SCZ or BP or to alleviate a sign or symptom of these diseases, suitable agents targeting the genes disclosed in the tables herein can be administered in combination in order to provide therapeutic benefit to the patient. Such agents should be administered in an effective dose. Alternatively, once a patient has been identified as having a genetic alteration predisposing the patient to SCZ or BP, drugs typically administered for the treatment of such disorders may be given.

First, a biological sample, or genotyping information would obtained from a patient. Genetic information gleaned from nucleic acids present in the sample would then be assessed for the presence or absence of the SCZ or BP associated genetic alterations (ie., SNP/CNV containing nucleic acids associated with onset of one or more SCZ or BP). The presence of these SNPs indicating the presence of SCZ, along with the simultaneous identification of the genes affected, providing the clinician with guidance as to which therapeutic agents are appropriate. The total treatment dose or doses (when two or more targets are to be modulated) can be administered to a subject as a single dose or can be administered using a fractionated treatment protocol, in which multiple/separate doses are administered over a more prolonged period of time, for example, over the period of a day to allow administration of a daily dosage or over a longer period of time to administer a dose over a desired period of time. One skilled in the art would know that the amount of SCZ agent required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having SCZ.

The effective dose of SCZ therapeutic agent(s) will depend on the mode of administration, and the weight of the individual being treated. The dosages described herein are generally those for an average adult but can be adjusted for the treatment of children. The dose will generally range from about 0.001 mg to about 1000 mg.

In an individual suffering from SZC in particular a more severe form of the disease, administration of SCZ therapeutic agents can be particularly useful when administered in combination, for example, with a conventional agent for treating such a disease. The skilled artisan would administer the SCZ therapeutic agent(s), alone or in combination and would monitor the effectiveness of such treatment using routine methods. Other conventional agents for the treatment of SCZ are provided in the table below.

Administration of the pharmaceutical preparation is preferably in an "effective amount" this being sufficient to show benefit to the individual. This amount prevents, alleviates, abates, or otherwise reduces the severity of SCZ or BP symptoms in a patient.

In a preferred embodiment of this invention, a method is provided for the synergistic treatment of SCZ using the pharmaceutical agents disclosed in the present example in combinatorial approaches. Advantageously, the synergistic method of this invention reduces the development of SCZ, or reduces symptoms of SCZ in a mammalian host. Additionally, therapeutic regimens suitable for simultaneous treatment of BP and SCZ disorders are also provided. The information provided herein guides the clinician in new treatment modalities for the management of SCZ.

Methods for the safe and effective administration of most of these agents are known to those skilled in the art. In addition, their administration is described in the standard literature. For example, the administration of many of the agents is described in the "Physicians' Desk Reference" (PDR), e.g., 1996 edition (Medical Economics Company, Montvale, N.J. 07645-1742, USA); the disclosure of which is incorporated herein by reference thereto.

The present invention also encompasses a pharmaceutical composition useful in the treatment of SCZ, comprising the administration of a therapeutically effective amount of the combinations of this invention, with or without pharmaceutically acceptable carriers or diluents. The synergistic pharmaceutical compositions of this invention comprise two or more of the agents listed in the table below and a pharmaceutically acceptable carrier. The compositions of the present invention may further comprise one or more pharmaceutically acceptable additional ingredient(s) such as alum, stabilizers, antimicrobial agents, buffers, coloring agents, flavoring agents, adjuvants, and the like. The anti-SCZ compositions of the present invention may be administered orally or parenterally including the intravenous, intramuscular, intraperitoneal, subcutaneous, rectal and topical routes of administration.

Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired. Intermittent therapy (e.g., one week out of three weeks or three out of four weeks) may also be used.

Certain types of SCZ can be treated effectively with a plurality of the compounds listed above. Such triple and quadruple combinations can provide greater efficacy. When used in such triple and quadruple combinations the dosages can be determined according to known protocols.

The combinations of the instant invention may also be co-administered with other well known therapeutic agents that are selected for their particular usefulness against the condition that is being treated. Combinations of the instant invention may alternatively be used sequentially with known pharmaceutically acceptable agent(s) when a multiple combination formulation is inappropriate.

Also, in general, the compounds listed above do not have to be administered in the same pharmaceutical composition, and may, because of different physical and chemical characteristics, have to be administered by different routes. For example, first compound may be administered orally to generate and maintain good blood levels thereof, while a second compound may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

As described previously, genome wide association studies (GWAS) have identified susceptibility genes associated with SCZ and BP. Drugs known to be useful for the treatment of SCZ are provided in the Table below. These drugs can be combined to synergistically treat SCZ or to simultaneously reduce symptoms or progression of SCZ.

The table below lists agents which target NTRK.

| | | | | |
|---|---|---|---|---|
| ARRY470 | PreClinical | Investigational Drug | Small | Array BioPharma Inc |
| ARRY872 | PreClinical | Investigational Drug | Small | Array BioPharma Inc |
| AZ23 | PreClinical | Investigational Drug | Small | AstraZeneca, Axon Medchem BV |
| AZD6918 | Phase I | Investigational Drug | NA | AstraZeneca |
| CE245677 | Phase I | Investigational Drug | NA | Pfizer Inc |
| DS6051 | Phase I | Investigational Drug | NA | Daiichi Sankyo Company Limited, Daiichi Sankyo Inc |
| KT6587 | PreClinical | Investigational Drug | NA | Kyowa Hakko Kirin Co Ltd, Cephalon Inc |
| LOXO101 | Phase I | Investigational Drug | Small | Array BioPharma Inc, Loxo Oncology Inc |
| PLX7486 | Phase I | Investigational Drug | Small | Plexxikon Inc, Daiichi Sankyo Company Limited |
| RXDX101 | Phase II | Investigational Drug | Small | Nerviano Medical Sciences, University of California San Francisco, Ignyta Inc |
| RXDX102 | PreClinical | Investigational Drug | NA | Nerviano Medical Sciences, Ignyta Inc |

Agents useful in the clinic for the treatment of schizophrenia include, without limitation, Serdolect, ABT126, ABT127, ABT925, Zoleptil, ABT354, Rexapin, Haloperidol lactate, Nuplazid, AM831, ACP104, Quetros, Aristab, Risperidone ACIS, Paxiprid, Loxapine succinate, Aripiprazole, Zolafren, DA/5HT Modulator ADAMED, Kwetaplex, ADX63365, ADX50938, ADX71149, ATx11004, Cimicoxib Affectis, FazaClo, GlyT-1 inhibitor, Joykem, Alkepin, Ilopt, InvegaSustenna, Asenapine maleate AMNEAL, AG0098, APN1125, AVL3288, Apexidone, Clozapex, Ziprasidone Hydrochloride, Haloperidol decanoate, Apo-Clozapine, Apo-Pimozide, Ziprasidone Hydrochloride, Olanzapine ODF LABTEC, Dogmil, Zyprexa, Rispa, Amipride, Seronia, Seroquel, Huntexil, Fasoracetam, Zyprobiox, Risbiodal, Biopiprazole, Aripiprazole, Miradol, Fluphenazine-decanoate and Prochlorperazineedisylate.

While the invention has been described in detail and with reference to specific examples thereof, it will be apparent to one skilled in the art that various changes and modifications can be made therein without departing from the spirit and scope thereof.

What is claimed is:

1. A method of treating schizophrenia (SCZ) or bi-polar (BP) disorder in a subject comprising:
   a) obtaining genotype sequence information from nucleic acids obtained from a subject;
   b) detecting in said information the presence of at least one SCZ or BP associated genetic alteration in NTRK3; and
   c) treating the subject with at least one agent selected from ARRY470, ARRY872, AZ23, AZD6918, CE245677, DS6051, KT6587, LOXO101, PLX7486, RXDX101, and RXDX102.

2. The method of claim 1, wherein the subject is treated with said at least one agent in combination with one or more additional agents selected from Serdolect, ABT126, ABT127, ABT925, Zoleptil, ABT354, Rexapin, Haloperidol lactate, Nuplazid, AM831, ACP104, Quetros, Aristab, Risperidone ACIS, Paxiprid, Loxapine succinate, Aripiprazole ,Zolafren, DA/5HT Modulator ADAMED, Kwetaplex, ADX63365, ADX50938, ADX71149, ATx11004, Cimicoxib Affectis, FazaClo, GlyT-1 inhibitor, Joykem, Alkepin, Ilopt, Invega Sustenna, Asenapine maleate AMNEAL, AG0098, APN1125, AVL3288, Apexidone, Clozapex, Ziprasidone Hydrochloride, Haloperidol decanoate, Apo-Clozapine, Apo-Pimozide, Ziprasidone Hydrochloride, Olanzapine ODF LABTEC, Dogmil, Zyprexa, Rispa, Amipride, Seronia, Seroquel, Huntexil, Zyprobiox, Fasoracetam, Risbiodal, Biopiprazole, Aripiprazole, Miradol, Fluphenazine decanoate, and Prochlorperazine edisylate.

3. The method of claim 1, further comprising detecting a genetic alteration in at least one gene selected from neuromedin B, TSNARE1, MAD1L1, CACNA1D, NT5DC2, ITH1, NEK4 NIMA, GNL3, PB1, GLT8D1, FTSJ2, NUDT1, SNX8, SEC11A, SCAND2, ZSCAN2, ALPK3, PDE8A, GRIN2A, GRIN2B, DLG2, DLG1, DLG4, ATP2B2, NOS1, ERBB4, ANSK1B, CHUK, CNTN2, CNTNAP2, CUL3, CREB1, CREB5, EP300, GABBR2, GNA13, NCOR2, NTRK3, PAK2, PTK2, PTK2B, PTN, PTPRF, STK4, SEMA4C, PTPRG, MAPK8IP1, TIAM1, IRS1, and YWHAZ and TCF4.

* * * * *